(12) United States Patent
Kobayashi

(10) Patent No.: US 8,779,137 B2
(45) Date of Patent: Jul. 15, 2014

(54) COMPOUND AND ORGANIC ELECTROLUMINESCENT ELEMENT USING THE SAME

(75) Inventor: Satoshi Kobayashi, Tsukuba (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 101 days.

(21) Appl. No.: 13/519,220

(22) PCT Filed: Dec. 22, 2010

(86) PCT No.: PCT/JP2010/073121
§ 371 (c)(1),
(2), (4) Date: Jun. 26, 2012

(87) PCT Pub. No.: WO2011/081065
PCT Pub. Date: Jul. 7, 2011

(65) Prior Publication Data
US 2012/0286654 A1    Nov. 15, 2012

(30) Foreign Application Priority Data
Dec. 28, 2009  (JP) .................................. 2009-297187

(51) Int. Cl.
C07D 471/04 (2006.01)
H01L 51/50 (2006.01)
C09K 11/06 (2006.01)

(52) U.S. Cl.
USPC .................. 546/36; 313/504; 252/301.26

(58) Field of Classification Search
USPC .................. 546/36; 313/504; 252/301.26
See application file for complete search history.

(56) References Cited

U.S. PATENT DOCUMENTS

| 2007/0126345 | A1 | 6/2007 | Hudack et al. |
| 2009/0096360 | A1 | 4/2009 | Tanaka et al. |
| 2010/0201259 | A1 | 8/2010 | Kobayashi |

FOREIGN PATENT DOCUMENTS

| JP | 2007-512249 A | 5/2007 |
| JP | 2009-114114 A | 5/2009 |
| JP | 2009-263665 A | 11/2009 |
| WO | 2007/077810 A1 | 7/2007 |

OTHER PUBLICATIONS

W. E. Hahn, et al., "Studies on the Relationship Between Color and Structure of Organic Compounds. Part III. Derivatives of Quinolonofluorene", Roczniki Chemii, 1975, pp. 1309-1327, vol. 49, Nos. 7-8.
International Search Report of PCT/JP2010/073121 dated Mar. 1, 2011.

*Primary Examiner* — Charanjit Aulakh
(74) *Attorney, Agent, or Firm* — Sughrue Mion, PLLC

(57) ABSTRACT

The present invention provides a novel compound having an excellent property to inject a hole into a device such as an organic EL device. More specifically, the present invention provides a compound comprising a residue obtained by removing at least one hydrogen atom from a structure represented by the following formula (1):

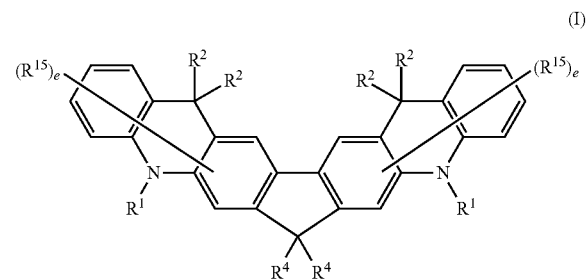

(I)

wherein
each $R^1$ represents a hydrogen atom, an alkyl group, or the like, each of such groups optionally having a substituent; the $R^1$s may be the same or different;
each $R^2$ represents a hydrogen atom, an alkyl group, or the like, each of such groups optionally having a substituent; the $R^2$s may be the same or different;
each $R^4$ represents a hydrogen atom, an alkyl group, or the like, each of such groups optionally having a substituent; the $R^4$s may be the same or different;
each $R^{15}$ represents an alkyl group or the like, each of such groups optionally having a substituent;
where there are a plurality of $R^{15}$, they may be the same or different;
each e represents an integer of from 0 to 6; and
the e's may be the same or different.

16 Claims, No Drawings

COMPOUND AND ORGANIC ELECTROLUMINESCENT ELEMENT USING THE SAME

CROSS REFERENCE TO RELATED APPLICATIONS

This application is a National Stage of International Application No. PCT/JP2010/073121 filed Dec. 22, 2010, claiming priority based on Japanese Patent Application No. 2009-297187 filed Dec. 28, 2009, the contents of all of which are incorporated herein by reference in their entirety.

TECHNICAL FIELD

The present invention relates to a compound and a method of producing the same. The invention also relates to a composition, a film, and a light-emitting device such as an organic electroluminescent device (hereinafter referred to as an "organic EL device") that comprise the compound and to a display apparatus and the like including such a light-emitting device.

BACKGROUND ART

In recent years, the development of color displays using organic EL devices is actively progressing, and various light-emitting materials and charge transport materials useful for organic EL devices are being studied. It is known that the use of a compound having an excellent hole injection property as the above-described materials in organic EL devices can reduce their driving voltage.

As an example of the compound having a hole injection property, a polymer compound obtained by polymerization of 2,7-bis(4-methyl-4'-bromo-diphenylamino)-9,9-dioctylfluorene has been reported (Patent Literature 1).

PRIOR ART LITERATURE

Patent Literature

Patent Literature 1: Japanese laid-open publication No. 2007-512249

SUMMARY OF THE INVENTION

Problem to be Solved by the Invention

However, the hole injection property of the above-described polymer compound is insufficient.

Accordingly, it is an object of the present invention to provide a compound having an excellent hole injection property.

Means for Solving Problem

The present inventor has made extensive studies to achieve the above object and succeeded to develop a compound and the like having an excellent hole injection property, and the present invention is thereby completed.

Specifically, the present invention is as follows.

[1] A compound comprising a residue obtained by removing at least one hydrogen atom from a structure represented by the following formula (1):

[Chemical formula 1]

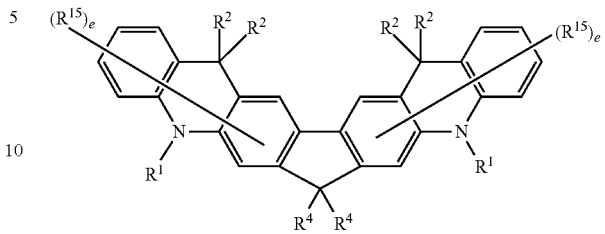

(1)

wherein
each $R^1$ represents a hydrogen atom, an alkyl group, an aryl group, an arylalkyl group, an acyl group, or a monovalent heterocyclic group, each of these groups optionally having a substituent;
the $R^1$s may be the same or different;
each $R^2$ represents a hydrogen atom, an alkyl group, an alkoxy group, an aryl group, an aryloxy group, an arylalkyl group, an arylalkoxy group, an alkenyl group, an arylalkenyl group, an acyl group, an acyloxy group, a monovalent heterocyclic group, or a heterocyclyloxy group, each of these groups optionally having a substituent;
the $R^2$s may be the same or different;
two $R^2$s bonded to the same carbon atom may be connected to form a ring;
each $R^4$ represents a hydrogen atom, an alkyl group, an aryl group, an arylalkyl group, or a monovalent heterocyclic group, each of these groups optionally having a substituent;
the $R^4$s may be the same or different;
the two $R^4$s may be connected to form a ring;
each $R^{15}$ represents an alkyl group, an alkoxy group, an aryl group, an aryloxy group, an arylalkyl group, an arylalkoxy group, an alkenyl group, an arylalkenyl group, an alkynyl group, an arylalkynyl group, an amino group, a silyl group, a halogen atom, an acyl group, an acyloxy group, a carbamoyl group, a monovalent heterocyclic group, a heterocyclyloxy group, a carboxyl group, a nitro group, or a cyano group, each of these groups optionally having a substituent;
where there are a plurality of $R^{15}$, they may be the same or different;
each e represents an integer of from 0 to 6; and
the plurality of e's may be the same or different.

[2] The compound of the above-described [1] that is a polymer compound comprising a repeating unit represented by the following formula (2):

[Chemical formula 2]

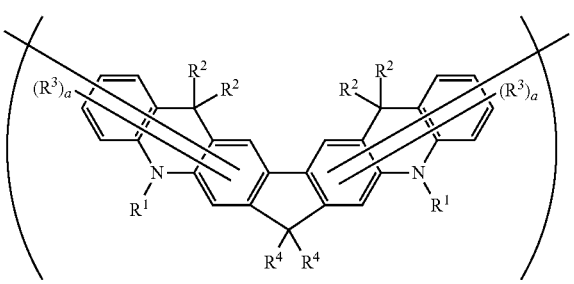

(2)

wherein
each $R^1$ represents a hydrogen atom, an alkyl group, an aryl group, an arylalkyl group, an acyl group, or a monovalent heterocyclic group, each of these groups optionally having a substituent;
the $R^1$s may be the same or different;
each $R^2$ represents a hydrogen atom, an alkyl group, an alkoxy group, an aryl group, an aryloxy group, an arylalkyl group, an arylalkoxy group, an alkenyl group, an arylalkenyl group, an acyl group, an acyloxy group, a monovalent heterocyclic group, or a heterocyclyloxy group, each of these groups optionally having a substituent;
the $R^2$s may be the same or different;
two $R^2$s bonded to the same carbon atom may be connected to form a ring;
each $R^3$ represents an alkyl group, an alkoxy group, an aryl group, an aryloxy group, an arylalkyl group, an arylalkoxy group, an alkenyl group, an arylalkenyl group, an alkynyl group, an arylalkynyl group, an amino group, a silyl group, a halogen atom, an acyl group, an acyloxy group, a carbamoyl group, a monovalent heterocyclic group, a heterocyclyloxy group, a carboxyl group, a nitro group, or a cyano group, each of these groups optionally having a substituent;
where there are a plurality of $R^3$, they may be the same or different;
each $R^4$ represents a hydrogen atom, an alkyl group, an aryl group, an arylalkyl group, or a monovalent heterocyclic group, each of these groups optionally having a substituent;
the $R^4$s may be the same or different;
the two $R^4$s may be connected to form a ring;
each a represents an integer of from 0 to 5; and
the a's may be the same or different.

[3] The compound of the above-described [2], wherein said repeating unit represented by formula (2) is a repeating unit represented by the following formula (3):

[Chemical formula 3]

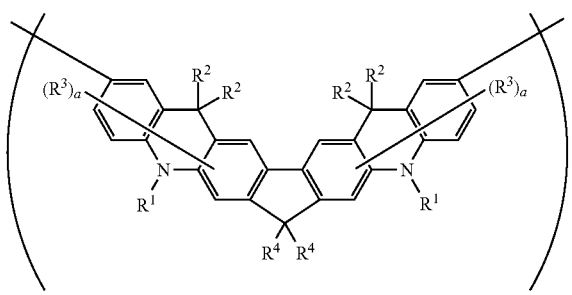

(3)

wherein $R^1$, $R^2$, $R^3$, $R^4$, and a are the same as defined for formula (2).

[4] The compound of the above-described [2] or [3] further comprising a repeating unit represented by the following formula (4):

[Chemical formula 4]

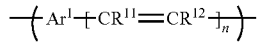

(4)

wherein
$Ar^1$ represents an arylene group or a divalent heterocyclic group, each of these groups optionally having a substituent;

$R^{11}$ and $R^{12}$ each independently represent a hydrogen atom, an alkyl group, an aryl group, a monovalent heterocyclic group, or a cyano group, each of these groups optionally having a substituent; and
n represents 0 or 1.

[5] The compound of the above-described [4], wherein the aforementioned repeating unit represented by formula (4) is a repeating unit represented by the following formula (5):

[Chemical formula 5]

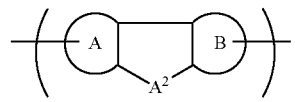

(5)

wherein
a ring A and a ring B each independently represent an aromatic hydrocarbon ring or an aromatic heterocyclic ring, each of these rings optionally having a substituent; and
$A^2$ represents a linking group.

[6] The compound of the above-described [5], wherein the aforementioned repeating unit represented by formula (5) is a repeating unit represented by the following formula (6):

[Chemical formula 6]

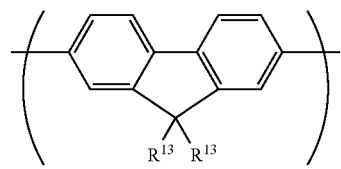

(6)

wherein
each $R^{13}$ represents a hydrogen atom, an alkyl group, an aryl group, an arylalkyl group, or a monovalent heterocyclic group, each of these groups optionally having a substituent;
the $R^{13}$s may be the same or different; and
the two $R^{13}$s may be connected to form a ring.

[7] A method of producing a compound comprising a repeating unit represented by the following formula (3):

[Chemical formula 7]

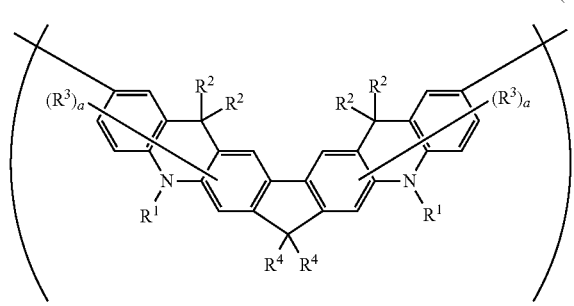

(3)

wherein each $R^1$ represents a hydrogen atom, an alkyl group, an aryl group, an arylalkyl group, an acyl group, or a monovalent heterocyclic group, each of these groups optionally having a substituent;

the $R^1$'s may be the same or different;

each $R^2$ represents a hydrogen atom, an alkyl group, an alkoxy group, an aryl group, an aryloxy group, an arylalkyl group, an arylalkoxy group, an alkenyl group, an arylalkenyl group, an acyl group, an acyloxy group, a monovalent heterocyclic group, or a heterocyclyloxy group, each of these groups optionally having a substituent;

the $R^2$s may be the same or different;

two $R^2$s bonded to the same carbon atom may be connected to form a ring;

each $R^3$ represents an alkyl group, an alkoxy group, an aryl group, an aryloxy group, an arylalkyl group, an arylalkoxy group, an alkenyl group, an arylalkenyl group, an alkynyl group, an arylalkynyl group, an amino group, a silyl group, a halogen atom, an acyl group, an acyloxy group, a carbamoyl group, a monovalent heterocyclic group, a heterocyclyloxy group, a carboxyl group, a nitro group, or a cyano group, each of these groups optionally having a substituent;

where there are plurality of $R^3$, they may be the same or different;

each $R^4$ represents a hydrogen atom, an alkyl group, an aryl group, an arylalkyl group, or a monovalent heterocyclic group, each of these groups optionally having a substituent;

the $R^4$s may be the same or different;

the two $R^4$s may be connected to form a ring;

each a represents an integer of from 0 to 5; and the a's may be the same or different;

the method comprising polymerizing a compound represented by the following formula (7):

[Chemical formula 8]

(7)

wherein $R^1$, $R^2$, $R^3$, $R^4$, and a are the same as in formula (3);

each $X^1$ represents a group capable of participating in polymerization; and the $X^1$s may be the same or different;

to obtain the compound comprising the repeating unit represented by formula (3).

[8] A compound represented by the following formula (7):

[Chemical formula 9]

(7)

wherein each $R^1$ represents a hydrogen atom, an alkyl group, an aryl group, an arylalkyl group, an acyl group, or a monovalent heterocyclic group, each of these groups optionally having a substituent;

the $R^1$s may be the same or different;

each $R^2$ represents a hydrogen atom, an alkyl group, an alkoxy group, an aryl group, an aryloxy group, an arylalkyl group, an arylalkoxy group, an alkenyl group, an arylalkenyl group, an acyl group, an acyloxy group, a monovalent heterocyclic group, or a heterocyclyloxy group, each of these groups optionally having a substituent;

the $R^2$s may be the same or different;

two $R^2$s bonded to the same carbon atom may be connected to form a ring;

each $R^3$ represents an alkyl group, an alkoxy group, an aryl group, an aryloxy group, an arylalkyl group, an arylalkoxy group, an alkenyl group, an arylalkenyl group, an alkynyl group, an arylalkynyl group, an amino group, a silyl group, a halogen atom, an acyl group, an acyloxy group, a carbamoyl group, a monovalent heterocyclic group, a heterocyclyloxy group, a carboxyl group, a nitro group, or a cyano group, each of these groups optionally having a substituent;

where there are a plurality of $R^3$, they may be the same or different;

each $R^4$ represents a hydrogen atom, an alkyl group, an aryl group, an arylalkyl group, or a monovalent heterocyclic group, each of these groups optionally having a substituent;

the $R^4$s may be the same or different;

the two $R^4$s may be connected to form a ring;

each $X^1$ represents a group capable of participating in polymerization;

the $X^1$s may be the same or different;

each a represents an integer of from 0 to 5; and the a's may be the same or different.

[9] A method of producing a compound represented by the following formula (7-1):

[Chemical formula 10]

(7-1)

wherein each $R^1$ represents a hydrogen atom, an alkyl group, an aryl group, an arylalkyl group, an acyl group, or a monovalent heterocyclic group, each of these groups optionally having a substituent;

the $R^1$s may be the same or different;

each $R^2$ represents a hydrogen atom, an alkyl group, an alkoxy group, an aryl group, an aryloxy group, an arylalkyl group, an arylalkoxy group, an alkenyl group, an arylalkenyl group, an acyl group, an acyloxy group, a monovalent heterocyclic group, or a heterocyclyloxy group, each of these groups optionally having a substituent;

the $R^2$s may be the same or different;

two $R^2$s bonded to the same carbon atom may be connected to form a ring;

each $R^3$ represents an alkyl group, an alkoxy group, an aryl group, an aryloxy group, an arylalkyl group, an arylalkoxy group, an alkenyl group, an arylalkenyl group, an alkynyl group, an arylalkynyl group, an amino group, a silyl group, a halogen atom, an acyl group, an acyloxy group, a carbamoyl group, a monovalent heterocyclic group, a heterocyclyloxy group, a carboxyl group, a nitro group, or a cyano group, each of these groups optionally having a substituent;

where there are a plurality of $R^3$, they may be the same or different;

each $R^4$ represents a hydrogen atom, an alkyl group, an aryl group, an arylalkyl group, or a monovalent heterocyclic group, each of these groups optionally having a substituent;

the $R^4$s may be the same or different;

the two $R^4$s may be connected to form a ring;

each a represents an integer of from 0 to 5;

the a's may be the same or different;

each $X^2$ represents a halogen atom; and the $X^2$s may be the same or different;

the method comprising reacting a compound represented by the following formula (8):

[Chemical formula 11]

(8)

wherein $R^1$, $R^2$, $R^3$, $R^4$, and a are the same as in formula (7-1);

with a halogenation agent to obtain the compound represented by formula (7-1).

[10] A compound represented by the following formula (8):

[Chemical formula 12]

(8)

wherein each $R^1$ represents a hydrogen atom, an alkyl group, an aryl group, an arylalkyl group, an acyl group, or a monovalent heterocyclic group, each of these groups optionally having a substituent;

the $R^1$s may be the same or different;

each $R^2$ represents a hydrogen atom, an alkyl group, an alkoxy group, an aryl group, an aryloxy group, an arylalkyl group, an arylalkoxy group, an alkenyl group, an arylalkenyl group, an acyl group, an acyloxy group, a monovalent heterocyclic group, or a heterocyclyloxy group, each of these groups optionally having a substituent;

the $R^2$s may be the same or different;

two $R^2$s bonded to the same carbon atom may be connected to form a ring;

each $R^3$ represents an alkyl group, an alkoxy group, an aryl group, an aryloxy group, an arylalkyl group, an arylalkoxy group, an alkenyl group, an arylalkenyl group, an alkynyl group, an arylalkynyl group, an amino group, a silyl group, a halogen atom, an acyl group, an acyloxy group, a carbamoyl group, a monovalent heterocyclic group, a heterocyclyloxy group, a carboxyl group, a nitro group, or a cyano group, each of these groups optionally having a substituent;

where there are a plurality of $R^3$, they may be the same or different;

each $R^4$ represents a hydrogen atom, an alkyl group, an aryl group, an arylalkyl group, or a monovalent heterocyclic group, each of these groups optionally having a substituent;

the $R^4$s may be the same or different;

the two $R^4$s may be connected to form a ring;

each a represents an integer of from 0 to 5; and the a's plurality of a may be the same or different.

[11] A method of producing a compound represented by the following formula (8):

[Chemical formula 13]

(8)

wherein
each $R^1$ represents a hydrogen atom, an alkyl group, an aryl group, an arylalkyl group, an acyl group, or a monovalent heterocyclic group, each of these groups optionally having a substituent;
the $R^1$s may be the same or different;
each $R^2$ represents a hydrogen atom, an alkyl group, an alkoxy group, an aryl group, an aryloxy group, an arylalkyl group, an arylalkoxy group, an alkenyl group, an arylalkenyl group, an acyl group, an acyloxy group, a monovalent heterocyclic group, or a heterocyclyloxy group, each of these groups optionally having a substituent;
the $R^2$s may be the same or different;
two $R^2$s bonded to the same carbon atom may be connected to form a ring;
each $R^3$ represents an alkyl group, an alkoxy group, an aryl group, an aryloxy group, an arylalkyl group, an arylalkoxy group, an alkenyl group, an arylalkenyl group, an alkynyl group, an arylalkynyl group, an amino group, a silyl group, a halogen atom, an acyl group, an acyloxy group, a carbamoyl group, a monovalent heterocyclic group, a heterocyclyloxy group, a carboxyl group, a nitro group, or a cyano group, each of these groups optionally having a substituent;
where there are a plurality of $R^3$, they may be the same or different;
each $R^4$ represents a hydrogen atom, an alkyl group, an aryl group, an arylalkyl group, or a monovalent heterocyclic group, each of these groups optionally having a substituent;
the $R^4$s may be the same or different;
the two $R^4$s may be connected to form a ring;
each a represents an integer of from 0 to 5; and
the a's may be the same or different;
the method comprising reacting a compound represented by the following formula (9):

[Chemical formula 14]

(9)

wherein
each $R^1$ represents a hydrogen atom, an alkyl group, an aryl group, an arylalkyl group, an acyl group, or a monovalent heterocyclic group, each of these groups optionally having a substituent;
the $R^1$s may be the same or different;
each $R^2$ represents a hydrogen atom, an alkyl group, an alkoxy group, an aryl group, an aryloxy group, an arylalkyl group, an arylalkoxy group, an alkenyl group, an arylalkenyl group, an acyl group, an acyloxy group, a monovalent heterocyclic group, or a heterocyclyloxy group, each of these groups optionally having a substituent;
the $R^2$s may be the same or different;
two $R^2$s bonded to the same carbon atom may be connected to form a ring;
each $R^3$ represents an alkyl group, an alkoxy group, an aryl group, an aryloxy group, an arylalkyl group, an arylalkoxy group, an alkenyl group, an arylalkenyl group, an alkynyl group, an arylalkynyl group, an amino group, a silyl group, a halogen atom, an acyl group, an acyloxy group, a carbamoyl group, a monovalent heterocyclic group, a heterocyclyloxy group, a carboxyl group, a nitro group, or a cyano group, each of these groups optionally having a substituent;
where there are a plurality of $R^3$, they may be the same or different;
each $R^4$ represents a hydrogen atom, an alkyl group, an aryl group, an arylalkyl group, or a monovalent heterocyclic group, each of these groups optionally having a substituent;
the $R^4$s may be the same or different;
the two $R^4$s may be connected to form a ring;
each a represents an integer of from 0 to 5; and
the a's may be the same or different;
in the presence of an acid to obtain the compound represented by formula (8).

[12] A compound represented by the following formula (9):

[Chemical formula 15]

(9)

wherein
each $R^1$ represents a hydrogen atom, an alkyl group, an aryl group, an arylalkyl group, an acyl group, or a monovalent heterocyclic group, each of these groups optionally having a substituent;
the $R^1$s may be the same or different;
each $R^2$ represents a hydrogen atom, an alkyl group, an alkoxy group, an aryl group, an aryloxy group, an arylalkyl group, an arylalkoxy group, an alkenyl group, an arylalkenyl group, an acyl group, an acyloxy group, a monovalent heterocyclic group, or a heterocyclyloxy group, each of these groups optionally having a substituent;
the $R^2$s may be the same or different;
two $R^2$s bonded to the same carbon atom may be connected to form a ring;
each $R^3$ represents an alkyl group, an alkoxy group, an aryl group, an aryloxy group, an arylalkyl group, an arylalkoxy group, an alkenyl group, an arylalkenyl group, an alkynyl group, an arylalkynyl group, an amino group, a silyl group, a halogen atom, an acyl group, an acyloxy group, a carbamoyl group, a monovalent heterocyclic group, a heterocyclyloxy group, a carboxyl group, a nitro group, or a cyano group, each of these groups optionally having a substituent;
where there are a plurality of $R^3$, they may be the same or different;
each $R^4$ represents a hydrogen atom, an alkyl group, an aryl group, an arylalkyl group, or a monovalent heterocyclic group, each of these groups optionally having a substituent;
the $R^4$s may be the same or different;
the two $R^4$ may be connected to form a ring;
each a represents an integer of from 0 to 5; and
the a's may be the same or different.

[13] A method of producing a compound represented by the following formula (9):

[Chemical formula 16]

(9)

[Structure: fluorene core with two diarylamine substituents bearing $-C(R^2)_2OH$ groups, $(R^3)_a$ aryl substituents, $R^1$ on N, and $R^4$ substituents on the fluorene sp3 carbon]

wherein
each $R^1$ represents a hydrogen atom, an alkyl group, an aryl group, an arylalkyl group, an acyl group, or a monovalent heterocyclic group, each of these groups optionally having a substituent;
the $R^1$s may be the same or different;
each $R^3$ represents an alkyl group, an alkoxy group, an aryl group, an aryloxy group, an arylalkyl group, an arylalkoxy group, an alkenyl group, an arylalkenyl group, an alkynyl group, an arylalkynyl group, an amino group, a silyl group, a halogen atom, an acyl group, an acyloxy group, a carbamoyl group, a monovalent heterocyclic group, a heterocyclyloxy group, a carboxyl group, a nitro group, or a cyano group, each of these groups optionally having a substituent;
where there are a plurality of $R^3$, they may be the same or different;
each $R^4$ represents a hydrogen atom, an alkyl group, an aryl group, an arylalkyl group, or a monovalent heterocyclic group, each of these groups optionally having a substituent;
the $R^4$s may be the same or different;
the two $R^4$s may be connected to form a ring;
each a represents an integer of from 0 to 5; and
the a's may be the same or different;
the method comprising reacting a compound represented by the following formula (10):

[Chemical formula 17]

(10)

[Structure: fluorene core with two diarylamine substituents bearing $-CO_2R^{16}$ groups]

wherein
$R^1$, $R^3$, $R^4$, and a are the same as in formula (9);
each $R^{16}$ represents an alkyl group, an aryl group, an arylalkyl group, or a monovalent heterocyclic group, each of these groups optionally having a substituent; and
the $R^{16}$s may be the same or different;

with a reducing agent or a compound represented by the following formula (11):

[Chemical formula 18]

$$R^{17}\text{-M} \quad (11)$$

wherein
$R^{17}$ represents an alkyl group, an alkoxy group, an aryl group, an aryloxy group, an arylalkyl group, an arylalkoxy group, an alkenyl group, an arylalkenyl group, an acyl group, an acyloxy group, a monovalent heterocyclic group, or a heterocyclyloxy group; and
M represents a lithium atom or a monohalogenated magnesium;
to obtain the compound represented by formula (9).

[14] A compound represented by the following formula (10):

[Chemical formula 19]

(10)

[Structure: fluorene core with two diarylamine substituents bearing $-CO_2R^{16}$ groups]

wherein
each $R^1$ represents a hydrogen atom, an alkyl group, an aryl group, an arylalkyl group, an acyl group, or a monovalent heterocyclic group, each of these groups optionally having a substituent;
the $R^1$s may be the same or different;
each $R^3$ represents an alkyl group, an alkoxy group, an aryl group, an aryloxy group, an arylalkyl group, an arylalkoxy group, an alkenyl group, an arylalkenyl group, an alkynyl group, an arylalkynyl group, an amino group, a silyl group, a halogen atom, an acyl group, an acyloxy group, a carbamoyl group, a monovalent heterocyclic group, a heterocyclyloxy group, a carboxyl group, a nitro group, or a cyano group, each of these groups optionally having a substituent;
where there are a plurality of $R^3$, they may be the same or different;
each $R^4$ represents a hydrogen atom, an alkyl group, an aryl group, an arylalkyl group, or a monovalent heterocyclic group, each of these groups optionally having a substituent;
the $R^4$s may be the same or different;
the two $R^4$s may be connected to form a ring;
each $R^{16}$ represents an alkyl group, an aryl group, an arylalkyl group, or a monovalent heterocyclic group, each of these groups optionally having a substituent;
the $R^{16}$s may be the same or different;
each a represents an integer of from 0 to 5; and
the a's may be the same or different.

[15] A method of producing a compound represented by the following formula (10):

[Chemical formula 20]

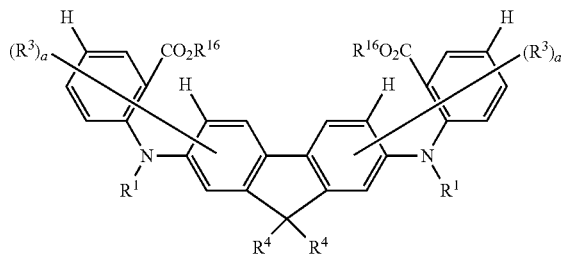

(10)

wherein
each $R^1$ represents a hydrogen atom, an alkyl group, an aryl group, an arylalkyl group, an acyl group, or a monovalent heterocyclic group, each of these groups optionally having a substituent;
the $R^1$s may be the same or different;
each $R^3$ represents an alkyl group, an alkoxy group, an aryl group, an aryloxy group, an arylalkyl group, an arylalkoxy group, an alkenyl group, an arylalkenyl group, an alkynyl group, an arylalkynyl group, an amino group, a silyl group, a halogen atom, an acyl group, an acyloxy group, a carbamoyl group, a monovalent heterocyclic group, a heterocyclyloxy group, a carboxyl group, a nitro group, or a cyano group, each of these groups optionally having a substituent;
where there are a plurality of $R^3$, they may be the same or different;
each $R^4$ represents a hydrogen atom, an alkyl group, an aryl group, an arylalkyl group, or a monovalent heterocyclic group, each of these groups optionally having a substituent;
the $R^4$s may be the same or different;
the two $R^4$s may be connected to form a ring;
each $R^{16}$ represents an alkyl group, an aryl group, an arylalkyl group, or a monovalent heterocyclic group, each of these groups optionally having a substituent;
the $R^{16}$s may be the same or different;
each a represents an integer of from 0 to 5; and
the a's may be the same or different;
the method comprising reacting a compound represented by the following formula (12):

[Chemical formula 21]

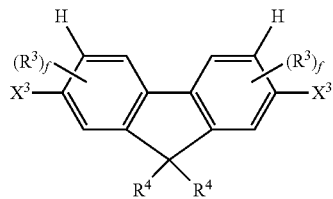

(12)

wherein
each $R^3$ represents an alkyl group, an alkoxy group, an aryl group, an aryloxy group, an arylalkyl group, an arylalkoxy group, an alkenyl group, an arylalkenyl group, an alkynyl group, an arylalkynyl group, an amino group, a silyl group, a halogen atom, an acyl group, an acyloxy group, a carbamoyl group, a monovalent heterocyclic group, a heterocyclyloxy group, a carboxyl group, a nitro group, or a cyano group, each of these groups optionally having a substituent;
where there are a plurality of $R^3$, they may be the same or different;
each $R^4$ represents a hydrogen atom, an alkyl group, an aryl group, an arylalkyl group, or a monovalent heterocyclic group, each of these groups optionally having a substituent;
the $R^4$s may be the same or different;
the two $R^4$s may be connected to form a ring;
each $X^3$ represents a chlorine atom, a bromine atom, or an iodine atom;
the $X^3$s may be the same or different;
each f represents an integer of from 0 to 2; and
the f's may be the same or different;
with a compound represented by the following formula (13):

[Chemical formula 22]

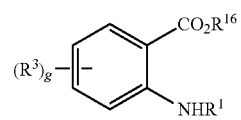

(13)

wherein
$R^3$ is the same as in formula (12);
$R^1$ represents a hydrogen atom, an alkyl group, an aryl group, an arylalkyl group, an acyl group, or a monovalent heterocyclic group, each of these groups optionally having a substituent;
$R^{16}$ represents an alkyl group, an aryl group, an arylalkyl group, or a monovalent heterocyclic group, each of these groups optionally having a substituent; and
g represents an integer of from 0 to 4;
in the presence of a transition metal catalyst and a base to obtain the compound represented by formula (10).
[16] A composition comprising:
(a) the compound of any of the above-described [1] to [6]; and
(b) at least one material selected from the group consisting of a hole transport material, an electron transport material, and a light-emitting material.
[17] A liquid composition comprising the compound of the above-described [1] to [6].
[18] A film obtained by using the compound of the above-described [1] to [6].
[19] A device obtained by using:
(a) electrodes comprising an anode and a cathode; and
(b) an organic layer comprising the compound of the above-described [1], which is disposed between the electrodes.
[20] A display apparatus including the device of the above-described [19].

Effects of the Invention

The compound of the present invention has an excellent hole injection property. Therefore, the compound of the present invention is useful for a material for light-emitting device such as an organic EL device and for a material for an electronic device such as a transistor. The compound of the present invention is also useful, for example, for a composition and a liquid composition which can be used as the above-described material, and for a film (e.g., a light-emitting film, a conductive film, or a semiconductor film), and for a display apparatus including a device such as a light-emitting device. The present invention also provides a compound that can be used for the synthesis of the above compounds.

EMBODIMENT FOR CARRYING OUT THE INVENTION

Next, the present invention will be described.

In the present description, Me in structural formulae represents a methyl group, and Ph represents a phenyl group.

<Compound>

The compound of the present invention comprises a residue obtained by removing at least one hydrogen atom from a structure represented by the following formula (1). When the compound of the present invention is a polymer compound, the residue may be located in its main chain, at a terminal end of the main chain, or in a side chain.

[Chemical formula 23]

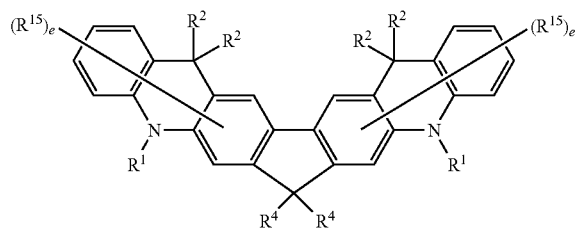

(1)

wherein each $R^1$ represents a hydrogen atom, an alkyl group, an aryl group, an arylalkyl group, an acyl group, or a monovalent heterocyclic group, each of these groups optionally having a substituent;

the $R^1$s may be the same or different;

each $R^2$ represents a hydrogen atom, an alkyl group, an alkoxy group, an aryl group, an aryloxy group, an arylalkyl group, an arylalkoxy group, an alkenyl group, an arylalkenyl group, an acyl group, an acyloxy group, a monovalent heterocyclic group, or a heterocyclyloxy group, each of these groups optionally having a substituent;

the $R^2$s may be the same or different;

two $R^2$ bonded to the same carbon atom may be connected to form a ring;

each $R^4$ represents a hydrogen atom, an alkyl group, an aryl group, an arylalkyl group or a monovalent heterocyclic group, each of these groups optionally having a substituent;

the $R^4$s may be the same or different;

the two $R^4$s may be connected to form a ring;

each $R^{15}$ represents an alkyl group, an alkoxy group, an aryl group, an aryloxy group, an arylalkyl group, an arylalkoxy group, an alkenyl group, an arylalkenyl group, an alkynyl group, an arylalkynyl group, an amino group, a silyl group, a halogen atom, an acyl group, an acyloxy group, a carbamoyl group, a monovalent heterocyclic group, a heterocyclyloxy group, a carboxyl group, a nitro group, or a cyano group, each of these groups optionally having a substituent;

where there are a plurality of $R^{15}$, they may be the same or different;

each e represents an integer of from 0 to 6; and the e's may be the same or different.

The alkyl group represented by $R^1$ may be linear, branched or cyclic. The number of carbon atoms in the alkyl group is generally 1 to 30, and the alkyl group optionally has a substituent. In this context, examples of such substituents may include an alkyl group, an alkoxy group, an aryl group, an aryloxy group, an arylalkyl group, an arylalkoxy group, an acyl group, an acyloxy group, a monovalent heterocyclic group, a heterocyclyloxy group, and a halogen atom, and the same applies hereinafter. Examples of the alkyl group may include a methyl group, an ethyl group, a n-propyl group, an isopropyl group, a n-butyl group, an isobutyl group, a sec-butyl group, a tert-butyl group, a n-pentyl group, an isoamyl group, a n-hexyl group, a cyclohexyl group, a n-heptyl group, a n-octyl group, and a trifluoromethyl group.

The aryl group represented by $R^1$ is a remaining atomic group obtained by removing one hydrogen atom from an aromatic hydrocarbon compound and may be a group having a condensed ring or a group having two or more rings. The aryl group optionally has a substituent, but the number of carbon atoms in the substituent is not included in the number of carbon atoms in the aryl group. The number of carbon atoms in the aryl group is generally 6 to 60 and preferably 6 to 30. Examples of the aryl group may include a phenyl group, $C_1$ to $C_{12}$ alkoxy phenyl groups ($C_1$ to $C_{12}$ means that the number of carbon atoms in an organic group immediately following $C_1$ to $C_{12}$ (in this case, the number of carbon atoms in the alkoxy group in the alkoxy phenyl group) is 1 to 12. The same applies hereinafter), $C_1$ to $C_{12}$ alkyl phenyl groups, a pentafluorophenyl group, a 1-naphthyl group, a 2-naphthyl group, a 1-anthracenyl group, a 2-anthracenyl group, a 9-anthracenyl group, a biphenyl group, and a terphenyl group. From the viewpoints of solubility in an organic solvent, device characteristics, and ease of synthesis, a $C_1$ to $C_{12}$ alkoxy phenyl group, and a $C_1$ to $C_{12}$ alkyl phenyl group are preferred, and a $C_1$ to $C_{12}$ alkyl phenyl groups is particularly preferred.

The arylalkyl group represented by $R^1$ optionally has a substituent, but the number of carbon atoms in the substituent is not included in the number of carbon atoms in the arylalkyl group. The number of carbon atoms in the arylalkyl group is generally 7 to 60, and examples of the arylalkyl group may include a phenyl-$C_1$ to $C_{12}$ alkyl group, a $C_1$ to $C_{12}$ alkoxy phenyl-$C_1$ to $C_{12}$ alkyl group, a $C_1$ to $C_{12}$ alkyl phenyl-$C_1$ to $C_{12}$ alkyl group, a 1-naphthyl-$C_1$ to $C_{12}$ alkyl group, and a 2-naphthyl-$C_1$ to $C_{12}$ alkyl group.

The number of carbon atoms in the acyl group represented by $R^1$ is generally 2 to 30, and the acyl group optionally has a substituent. However, the number of carbon atoms in the substituent is not included in the number of carbon atoms in the acyl group. Examples of the acyl group may include an acetyl group, a propionyl group, a butyryl group, an isobutyryl group, a pivaloyl group, a benzoyl group, a trifluoroacetyl group, and a pentafluorobenzoyl group.

The monovalent heterocyclic group represented by $R^1$ is a remaining atomic group obtained by removing one hydrogen atom from a heterocyclic compound (i.e., an organic compound having a cyclic structure in which the devices constituting the ring include not only carbon atoms but also a heteroatom such as an oxygen atom, a sulfur atom, a nitrogen atom, a phosphorus atom, or a boron atom). The number of carbon atoms in the monovalent heterocyclic group is generally 2 to 30 and preferably 2 to 15. In the monovalent heterocyclic group, its heterocycle optionally has a substituent, but the number of carbon atoms in the substituent on the heterocycle is not included in the number of carbon atoms in the monovalent heterocyclic group.

Examples of the monovalent heterocyclic group may include a thienyl group, a $C_1$ to $C_{12}$ alkyl thienyl group, a pyrrolyl group, a furyl group, a pyridyl group, a $C_1$ to $C_{12}$ alkyl pyridyl group, a piperidyl group, a quinolyl group, and an isoquinolyl group. An monovalent aromatic heterocyclic group is preferred, and a thienyl group, a $C_1$ to $C_{12}$ alkyl thienyl group, a pyridyl group, and a $C_1$ to $C_{12}$ alkyl pyridyl group are more preferred.

Examples of the alkyl group, the aryl group, the arylalkyl group, the acyl group, and the monovalent heterocyclic group represented by $R^2$ are the same as those described and exemplified for $R^1$.

The alkoxy group represented by $R^2$ may be linear, branched or cyclic. The number of carbon atoms in the alkoxy group is generally 1 to 30, and the alkoxy group optionally has a substituent. The number of carbon atoms in the substituent is not included in the number of carbon atoms in the alkoxy group. Examples of the alkoxy group may include a methoxy group, an ethoxy group, a n-propyloxy group, an iso-propyloxy group, a n-butoxy group, an isobutoxy group, a sec-butoxy group, a tert-butoxy group, a n-pentyloxy group, an isoamyloxy group, a n-hexyloxy group, a cyclohexyloxy group, a n-heptyloxy group, a n-octyloxy group, and a trifluoromethoxy group.

The number of carbon atoms in the aryloxy group represented by $R^2$ is generally 6 to 60, and the aryloxy group optionally has a substituent. The number of carbon atoms in the substituent is not included in the number of carbon atoms in the aryloxy group. Examples of the aryloxy group may include a phenoxy group, a $C_1$ to $C_{12}$ alkoxy phenoxy group, a $C_1$ to $C_{12}$ alkyl phenoxy group, a pentafluorophenyloxy group, a 1-naphthyloxy group, a 2-naphthyloxy group, a 1-anthracenyloxy group, a 2-anthracenyloxy group, a 9-anthracenyloxy group, a biphenyloxy group, and a terphenyloxy group.

The number of carbon atoms in the arylalkoxy group represented by $R^2$ is generally 7 to 60, and the arylalkoxy group optionally has a substituent. The number of carbon atoms in the substituent is not included in the number of carbon atoms in the arylalkoxy group. Examples of the arylalkoxy group may include a phenyl-$C_1$ to $C_{12}$ alkoxy group such as a phenylmethoxy group, a phenylethoxy group, a phenylbutoxy group, a phenylpentyloxy group, a phenylhexyloxy group, a phenylheptyloxy group, or a phenyloctyloxy group; a $C_1$ to $C_{12}$ alkoxy phenyl-$C_1$ to $C_{12}$ alkoxy group; a $C_1$ to $C_{12}$ alkyl phenyl-$C_1$ to $C_{12}$ alkoxy group; a 1-naphthyl-$C_1$ to $C_{12}$ alkoxy group; and a 2-naphthyl-$C_1$ to $C_{12}$ alkoxy group.

The number of carbon atoms in the alkenyl group represented by $R^2$ is 2 to 30, and the alkenyl group optionally has a substituent. The number of carbon atoms in the substituent is not included in the number of carbon atoms in the alkenyl group. Examples of the alkenyl group may include a vinyl group, a 1-propylenyl group, a 2-propylenyl group, a butenyl group, a pentenyl group, a hexenyl group, a heptenyl group, an octenyl group, and a cyclohexenyl group.

The number of carbon atoms in the arylalkenyl group represented by $R^2$ is generally 8 to 60, and the arylalkenyl group optionally has a substituent. The number of carbon atoms in the substituent is not included in the number of carbon atoms in the arylalkenyl group. Examples of the arylalkenyl group may include a phenyl-$C_2$ to $C_{12}$ alkenyl group, a $C_1$ to $C_{12}$ alkoxy phenyl-$C_2$ to $C_{12}$ alkenyl group, a $C_1$ to $C_{12}$ alkyl phenyl-$C_2$ to $C_{12}$ alkenyl group, a 1-naphthyl-$C_2$ to $C_{12}$ alkenyl group, and a 2-naphthyl-$C_2$ to $C_{12}$ alkenyl group.

The number of carbon atoms in the acyloxy group represented by $R^2$ is generally 2 to 30, and the acyloxy group optionally has a substituent. The number of carbon atoms in the substituent is not included in the number of carbon atoms in the acyloxy group. Examples of the acyloxy group may include an acetoxy group, a propionyloxy group, a butyryloxy group, an isobutyryloxy group, a pivaloyloxy group, a benzoyloxy group, a trifluoroacetyloxy group, and a pentafluorobenzoyloxy group.

The heterocyclyloxy group represented by $R^2$ is a group represented by a formula: $Q^1$-O— (wherein $Q^1$ represents a monovalent heterocyclic group), and the number of carbon atoms in the heterocyclyloxy group is generally 2 to 30. Examples of the monovalent heterocyclic group represented by $Q^1$ are the same as those described and exemplified for the monovalent heterocyclic group represented by $R^1$. The heterocyclyloxy group optionally has a substituent, but the number of carbon atoms in the substituent is not included in the number of carbon atoms in the heterocyclyloxy group. Examples of the heterocyclyloxy group may include a thienyloxy group, a $C_1$ to $C_{12}$ alkyl thienyloxy group, a pyrrolyloxy group, a furyloxy group, a pyridyloxy group, a $C_1$ to $C_{12}$ alkyl pyridyloxy group, an imidazolyloxy group, a pyrazolyloxy group, a triazolyloxy group, an oxazolyloxy group, a thiazoleoxy group, and a thiadiazoleoxy group.

The alkyl group, the alkoxy group, the aryl group, the acyloxy group, the arylalkyl group, the arylalkoxy group, the alkenyl group, the arylalkenyl group, the acyl group, the acyloxy group, the monovalent heterocyclic group, and the heterocyclyloxy group represented by $R^{15}$ are the same as those described and exemplified for the $R^1$ and $R^2$.

The number of carbon atoms in the alkynyl group represented by $R^{15}$ is 2 to 30, and the alkynyl group optionally has a substituent. The number of carbon atoms in the substituent is not included in the number of carbon atoms in the alkynyl group. Examples of the alkynyl group may include an ethynyl group, a 1-propynyl group, a 2-propynyl group, a butynyl group, a pentynyl group, a hexynyl group, a heptynyl group, an octynyl group, and a cyclohexylethynyl group.

The number of carbon atoms in the arylalkynyl group represented by $R^{15}$ is generally 8 to 60, and the arylalkynyl group optionally has a substituent. The number of carbon atoms in the substituent is not included in the number of carbon atoms in the arylalkynyl group. Examples of the arylalkynyl group may include a phenyl-$C_2$ to $C_{12}$ alkynyl group, a $C_1$ to $C_{12}$ alkoxy phenyl-$C_2$ to $C_{12}$ alkynyl group, a $C_1$ to $C_{12}$ alkyl phenyl-$C_2$ to $C_{12}$ alkynyl group, a 1-naphthyl-$C_2$ to $C_{12}$ alkynyl group, and a 2-naphthyl-$C_2$ to $C_{12}$ alkynyl group.

The amino group represented by $R^{15}$ may be an unsubstituted amino group or an amino group substituted with one or two groups selected from the group consisting of an alkyl group, an aryl group, an arylalkyl group, and a monovalent heterocyclic group. The alkyl group, the aryl group, the arylalkyl group, and the monovalent heterocyclic group optionally have a substituent. The number of carbon atoms in the amino group, excluding the number of carbon atoms in the substituent, is generally 1 to 60. Examples of the amino group may include a methylamino group, a dimethylamino group, an ethylamino group, a diethylamino group, a n-propylamino group, a di(n-propyl)amino group, an isopropylamino group, a di(isopropyl)amino group, a di(n-butyl)amino group, a di(isobutyl)amino group, a di(sec-butyl)amino group, a di(tert-butyl)amino group, a dicyclohexylamino group, a pyrrolidyl group, a piperidyl group, a phenylamino group, a diphenylamino group, a $C_1$ to $C_{12}$ alkoxy phenylamino group, a di($C_1$ to $C_{12}$ alkoxy phenyl)amino group, and a di($C_1$ to $C_{12}$ alkyl phenyl)amino group.

The silyl group represented by $R^{15}$ may be an unsubstituted silyl group or a silyl group substituted with 1 to 3 groups selected from the group consisting of an alkyl group, an aryl group, an arylalkyl group, and a monovalent heterocyclic group. The number of carbon atoms in the silyl group is generally 1 to 60. The alkyl group, the aryl group, the arylalkyl group, and the monovalent heterocyclic group optionally have a substituent. Examples of the silyl group may include a trimethylsilyl group, a triethylsilyl group, a tripropylsilyl group, a tri-isopropylsilyl group, a dimethyl-isopropylsilyl group, a tert-butyldimethylsilyl group, a triphenylsilyl group, a tribenzylsilyl group, a diphenylmethylsilyl group, a tert-butyldiphenylsilyl group, and a dimethylphenylsilyl group. Preferably, the monovalent heterocyclic group is a monovalent aromatic heterocyclic group.

Examples of the halogen atom represented by $R^{15}$ may include a fluorine atom, a chlorine atom, a bromine atom, and an iodine atom.

The number of carbon atoms in the carbamoyl group represented by $R^{15}$ is generally 1 to 30, and the carbamoyl group optionally has a substituent. The number of carbon atoms in the substituent is not included in the number of carbon atoms in the carbamoyl group. Examples of the carbamoyl group may include a formamido group, an acetamido group, a propionamido group, a butyramido group, a benzamido group, a trifluoroacetamido group, a pentafluorobenzamido group, a diformamido group, a diacetamido group, a dipropionamido group, a dibutyramido group, a dibenzamido group, a ditrifluoroacetamido group, and a dipentafluorobenzamido group.

The carboxyl group represented by $R^{15}$ may be an unsubstituted carboxyl group or a carboxyl group substituted with an alkyl group, an aryl group, an arylalkyl group, or a monovalent heterocyclic group. The number of carbon atoms in the carboxyl group is generally 2 to 30. Examples of the carboxyl group may include a methoxycarbonyl group, an ethoxycarbonyl group, a n-propoxycarbonyl group, an iso-propoxycarbonyl group, a n-butoxycarbonyl group, an iso-butoxycarbonyl group, a sec-butoxycarbonyl group, a tert-butoxycarbonyl group, a n-pentyloxycarbonyl group, a n-hexyloxycarbonyl group, a cyclohexyloxycarbonyl group, a n-heptyloxycarbonyl group, a n-octyloxycarbonyl group, and a trifluoromethoxycarbonyl group.

The alkyl group, the aryl group, the arylalkyl group, and the monovalent heterocyclic group represented by $R^4$ are the same as those described and exemplified for $R^1$. The two $R^4$s may be connected to form a ring but preferably do not form a ring.

e represents an integer of from 0 to 6. Preferably, two e are not simultaneously 6. More preferably, the two e are each 0 or 1.

Preferably, the above-described compound comprising a residue obtained by removing at least one hydrogen atom from the structure represented by formula (1) is a polymer compound (hereinafter referred to as a "polymer compound of the present invention"). Preferably, from the viewpoints of ease of synthesis and ease of controlling the copolymerization ratio of the polymer compound, the polymer compound is a polymer compound comprising a repeating unit represented by the following formula (2).

wherein
each $R^1$ represents a hydrogen atom, an alkyl group, an aryl group, an arylalkyl group, an acyl group, or a monovalent heterocyclic group, each of these groups optionally having a substituent;
the $R^1$s may be the same or different;
each $R^2$ represents a hydrogen atom, an alkyl group, an alkoxy group, an aryl group, an aryloxy group, an arylalkyl group, an arylalkoxy group, an alkenyl group, an arylalkenyl group, an acyl group, an acyloxy group, a monovalent heterocyclic group, or a heterocyclyloxy group, each of these groups optionally having a substituent;
the $R^2$s may be the same or different;
two $R^2$ bonded to the same carbon atom may be connected to form a ring;
$R^3$ each represent an alkyl group, an alkoxy group, an aryl group, an aryloxy group, an arylalkyl group, an arylalkoxy group, an alkenyl group, an arylalkenyl group, an alkynyl group, an arylalkynyl group, an amino group, a silyl group, a halogen atom, an acyl group, an acyloxy group, a carbamoyl group, a monovalent heterocyclic group, a heterocyclyloxy group, a carboxyl group, a nitro group, or a cyano group, each of these groups optionally having a substituent;
where there are a plurality of $R^3$, they may be the same or different;
each $R^4$ represents a hydrogen atom, an alkyl group, an aryl group, an arylalkyl group, or a monovalent heterocyclic group, each of these groups optionally having a substituent;
the $R^4$s may be the same or different;
the two $R^4$s may be connected to form a ring;
each a represents an integer of from 0 to 5; and
the a's may be the same or different.

In the above-described formula (2), the alkyl group, the alkoxy group, the aryl group, the aryloxy group, the arylalkyl group, the arylalkoxy group, the alkenyl group, the arylalkenyl group, the alkynyl group, the arylalkynyl group, the amino group, the silyl group, the halogen atom, the acyl group, the acyloxy group, the carbamoyl group, the monovalent heterocyclic group, the heterocyclyloxy group, the carboxyl group, the nitro group, and the cyano group represented by $R^3$ and the substituents in which these groups optionally have are the same as the atoms and groups described for $R^{15}$ above. Each a represents an integer of from 0 to 5 and is preferably 0.

Examples of the above-described repeating unit represented by formula (2) may include the following repeating units.

[Chemical formula 24]

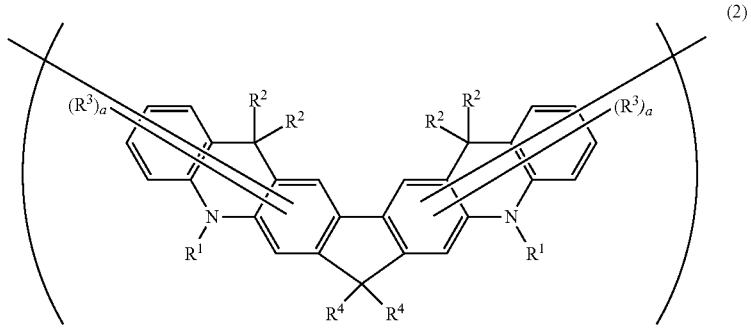

(2)

[Chemical formula 25]
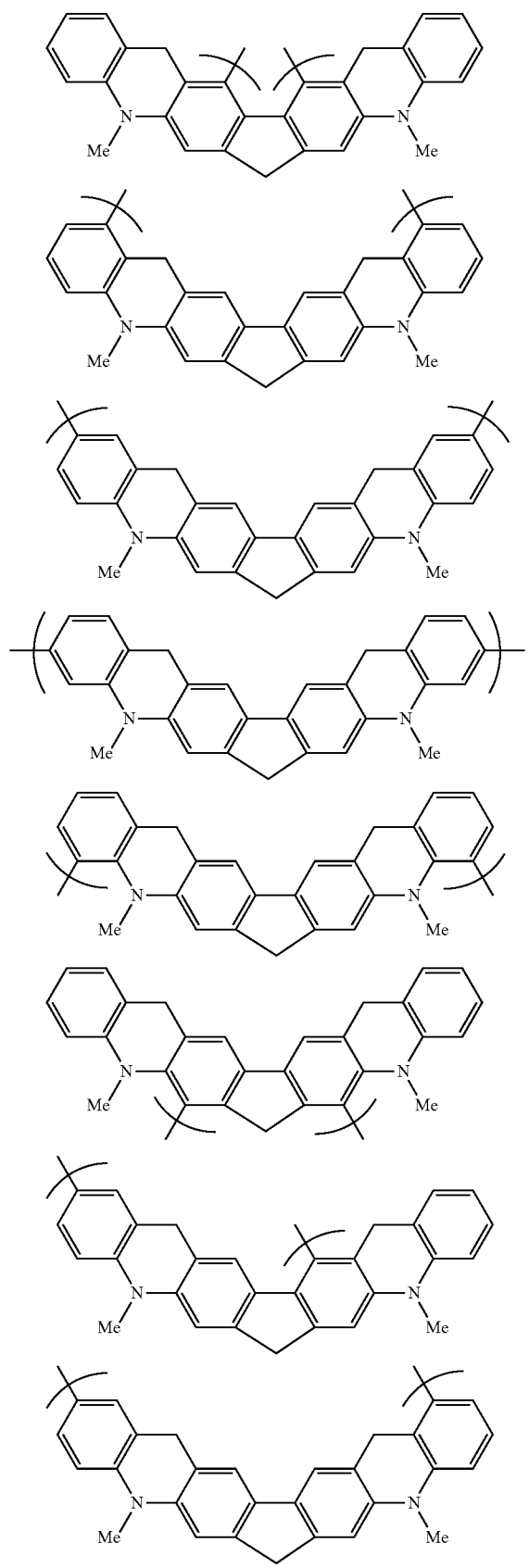
[Chemical formula 26]
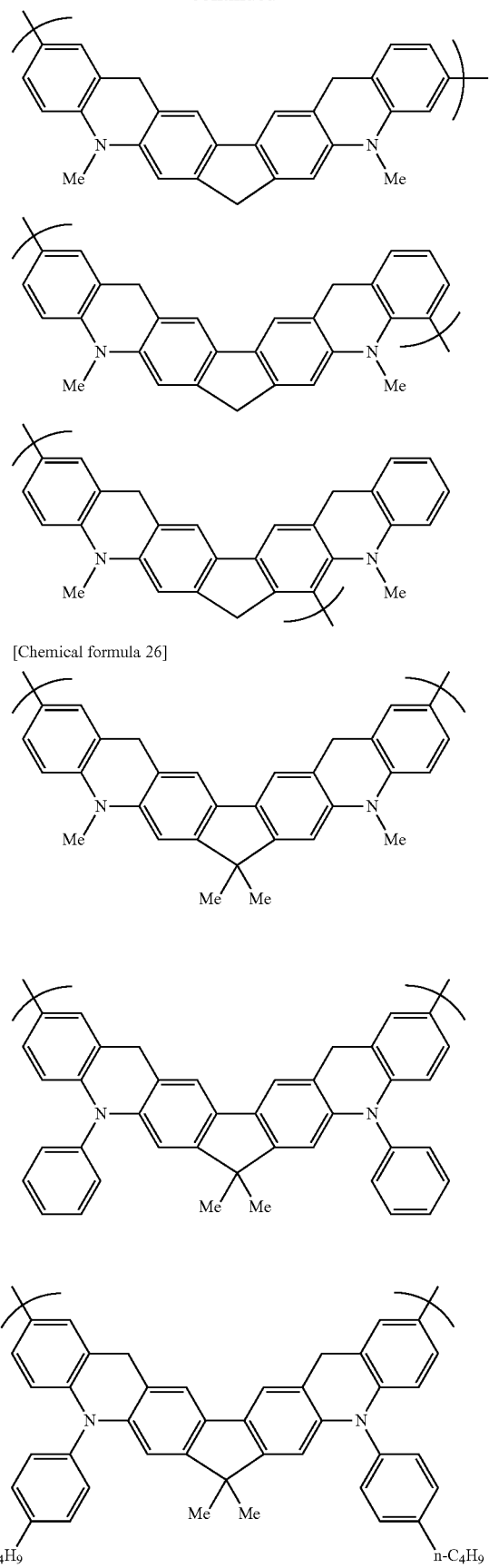

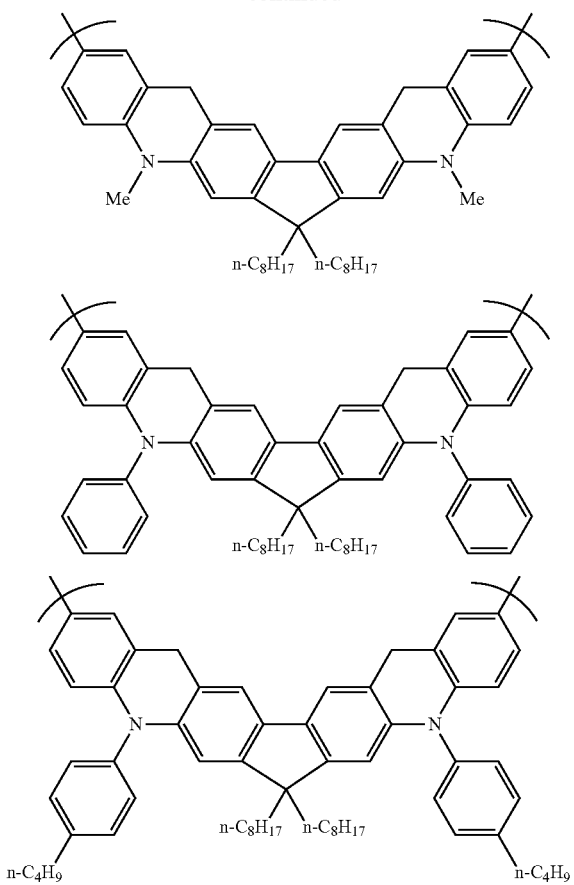
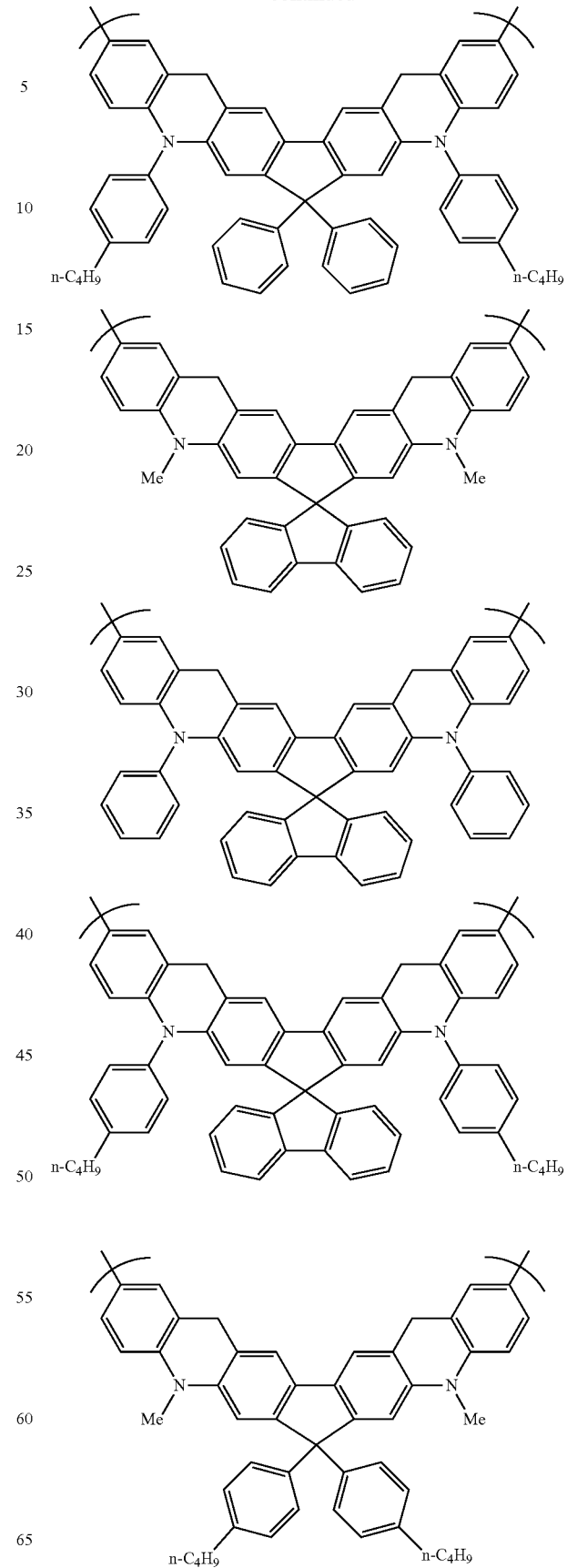

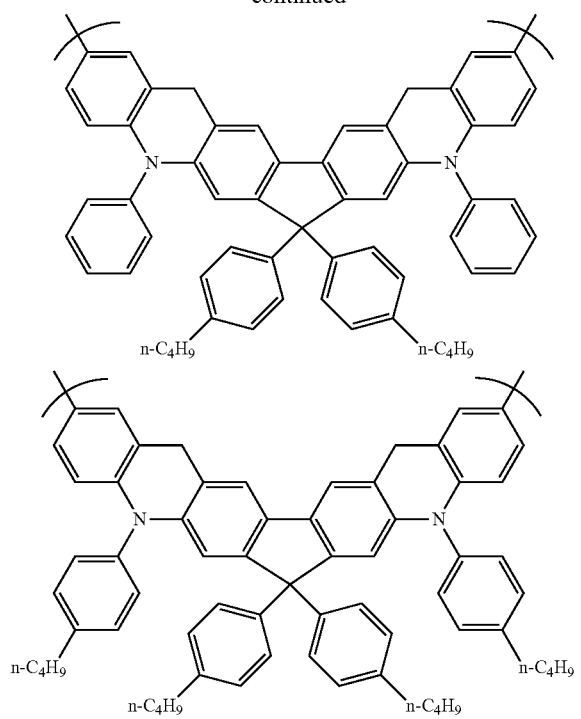
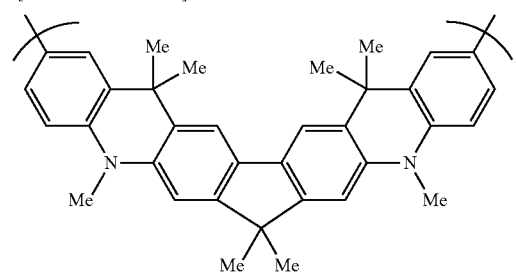
[Chemical formula 27]
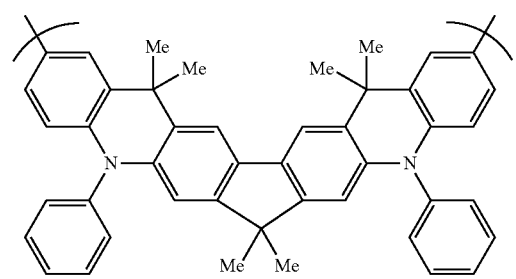
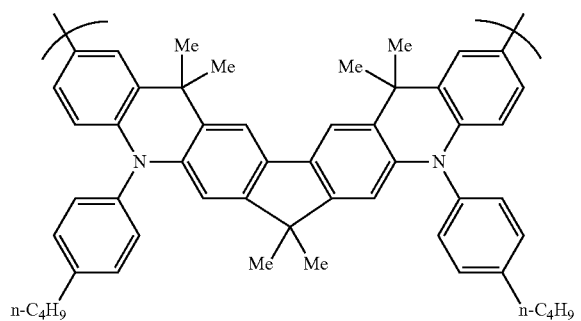
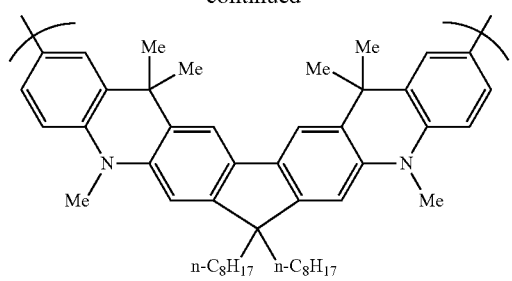
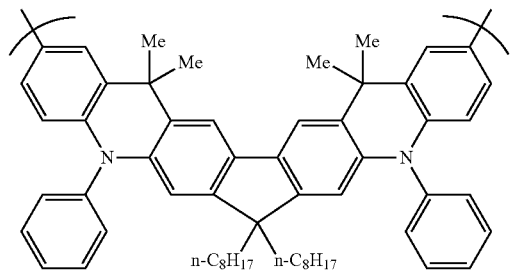
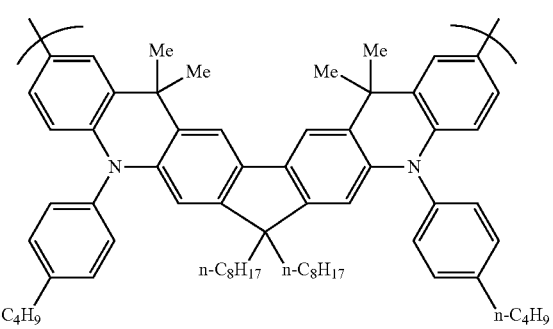
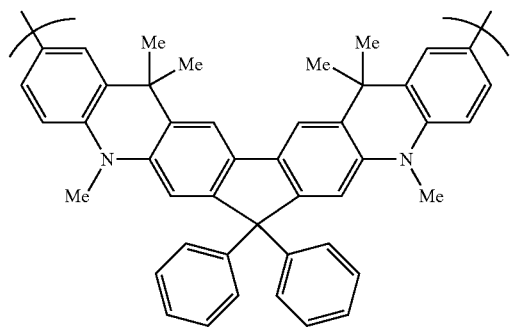
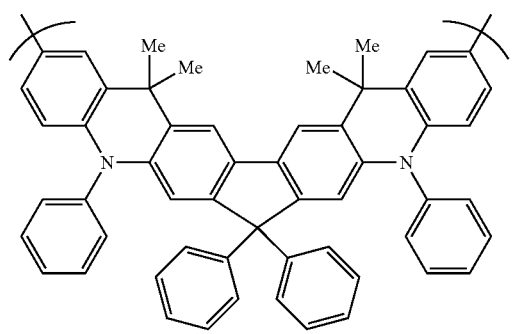

27
-continued
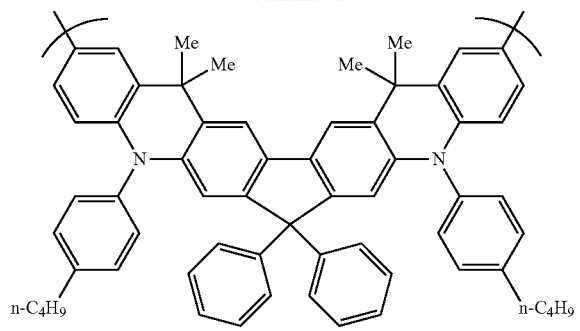
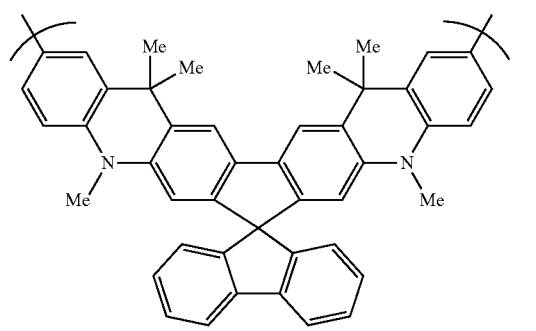
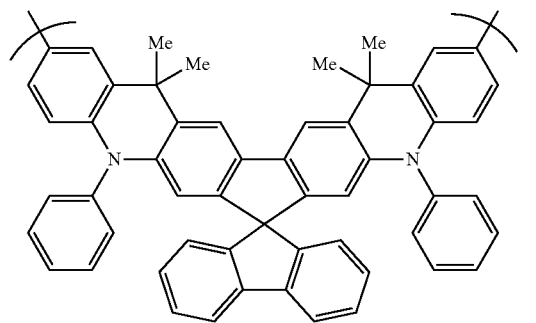
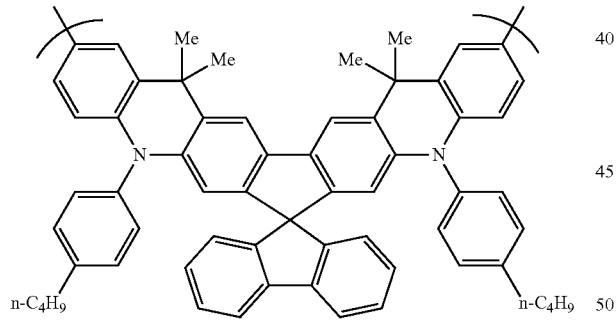
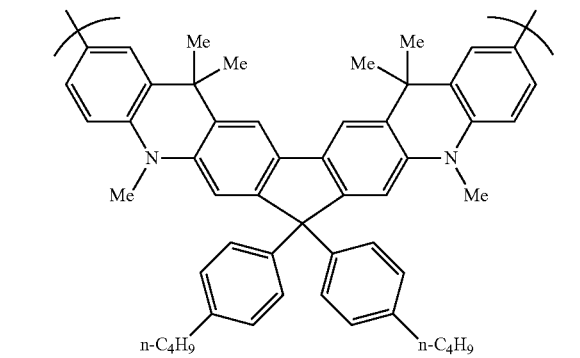
28
-continued
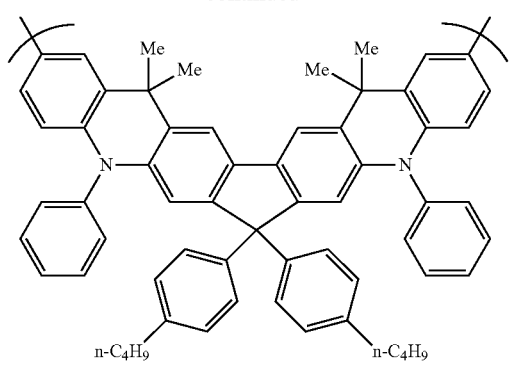
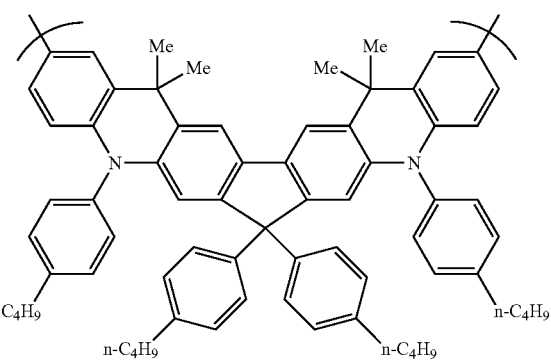
[Chemical formula 28]
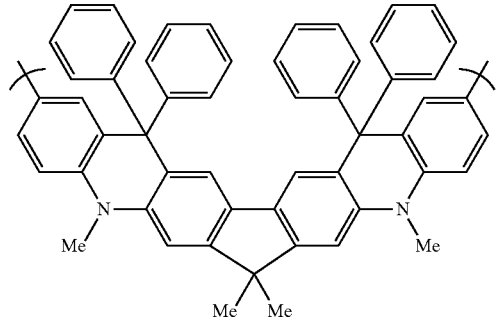
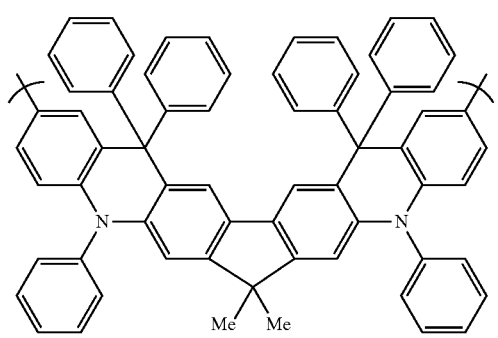

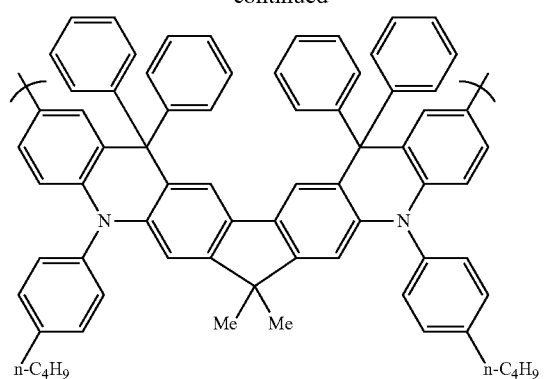
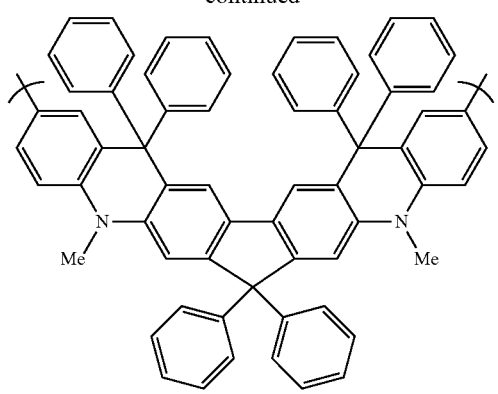
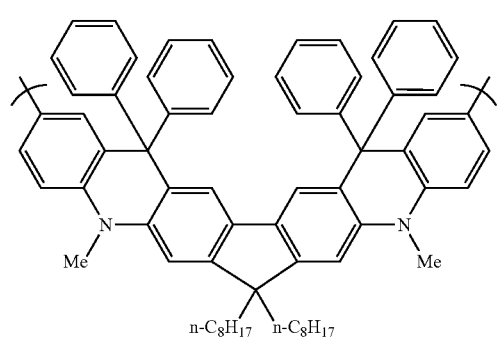
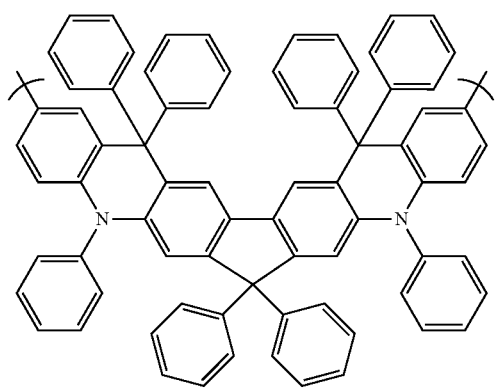
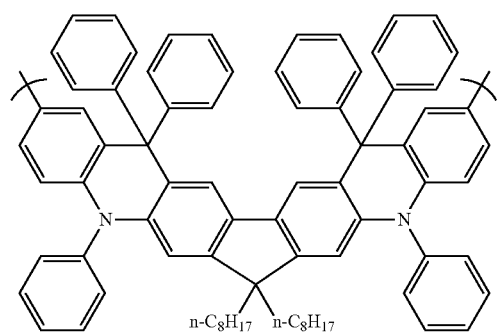
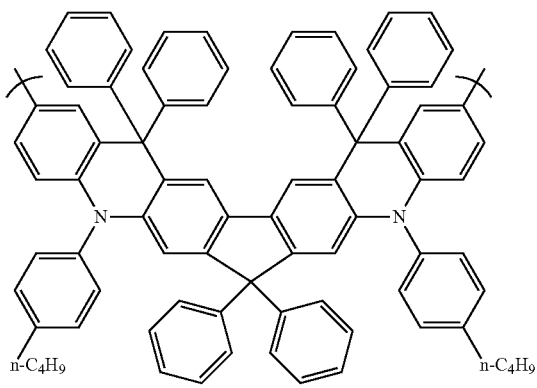
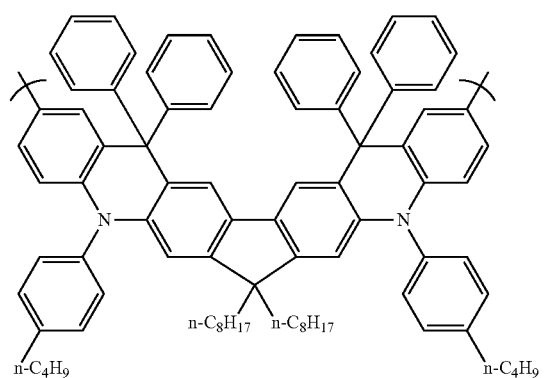
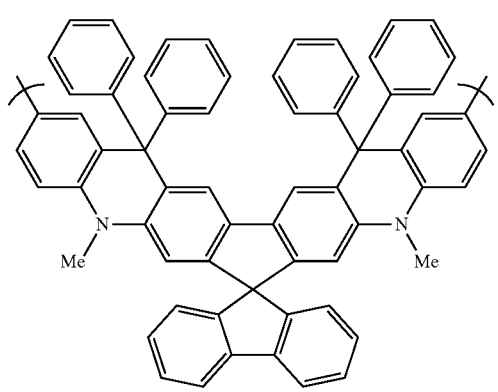

31
-continued
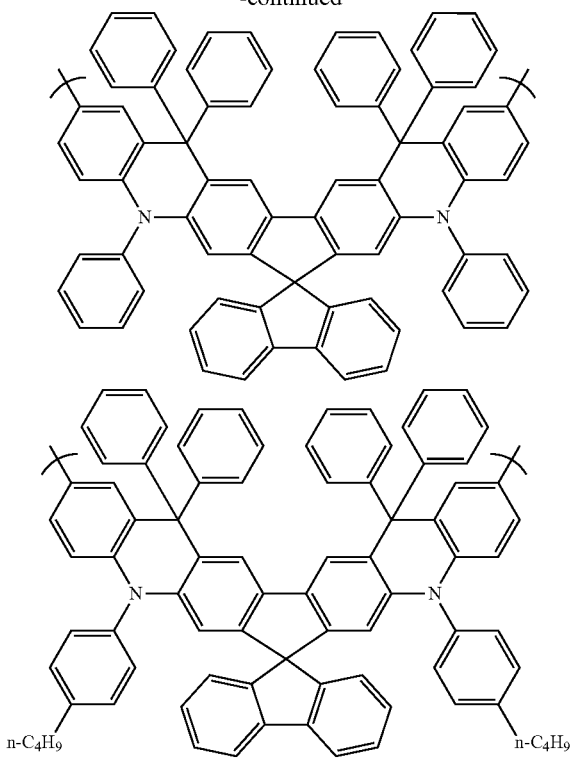
32
-continued
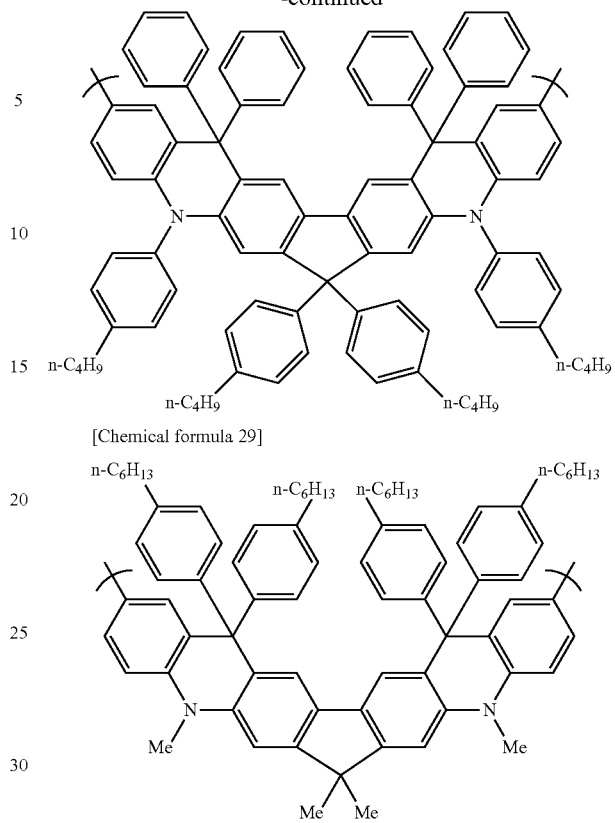
[Chemical formula 29]
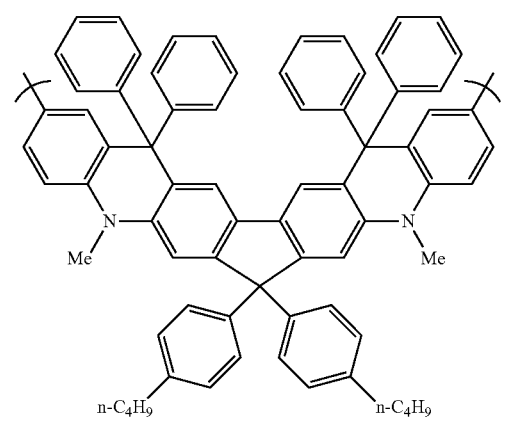
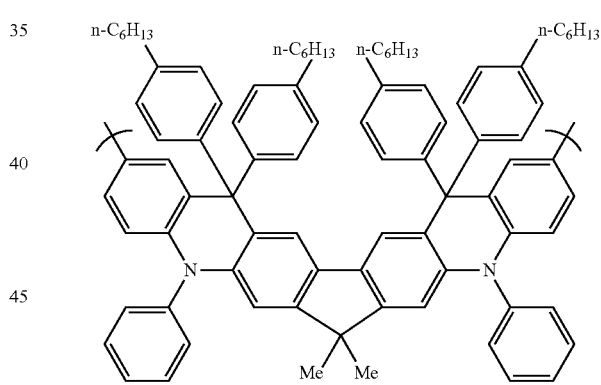
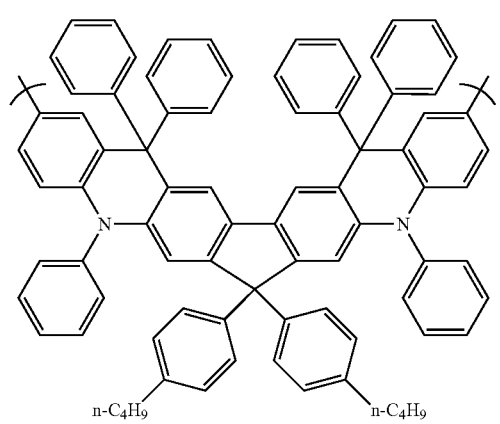
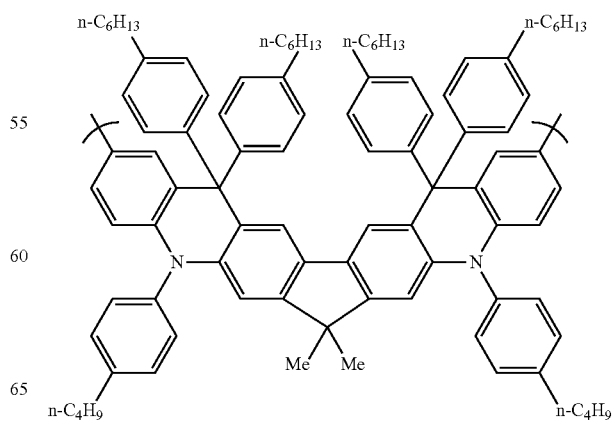

-continued
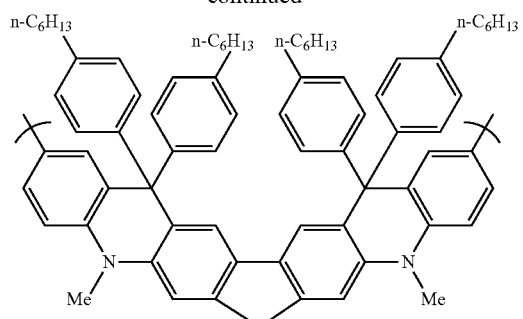
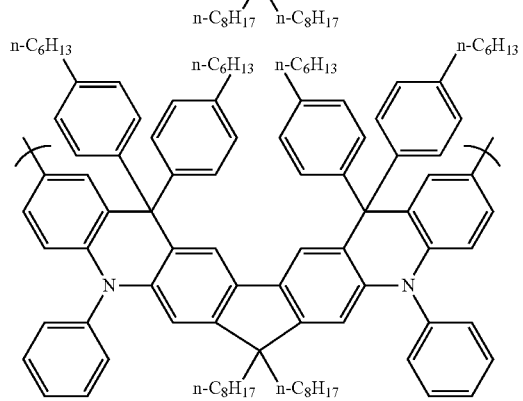
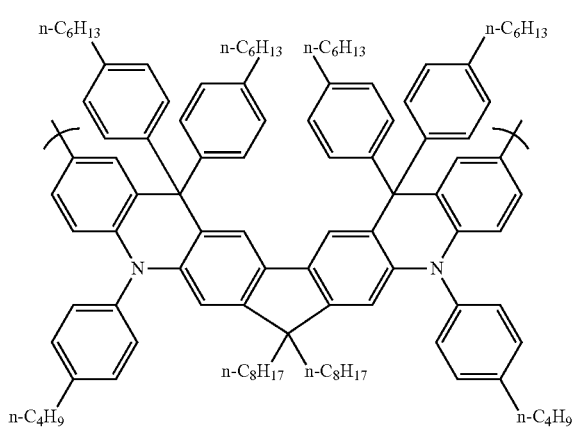
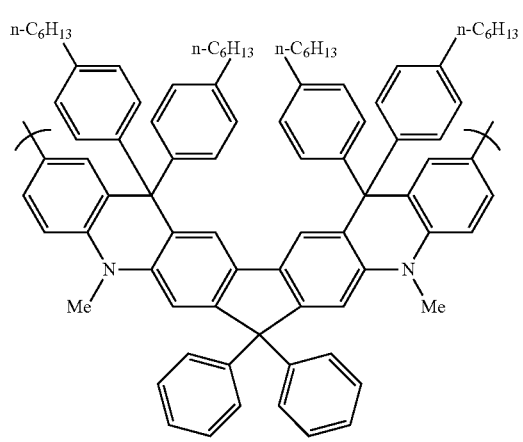
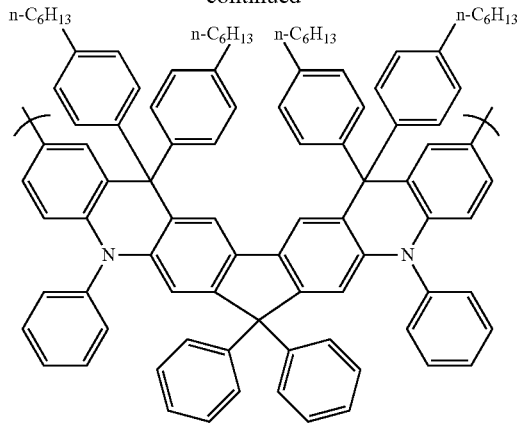
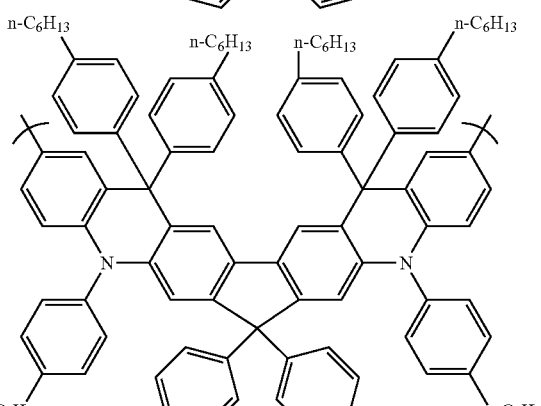
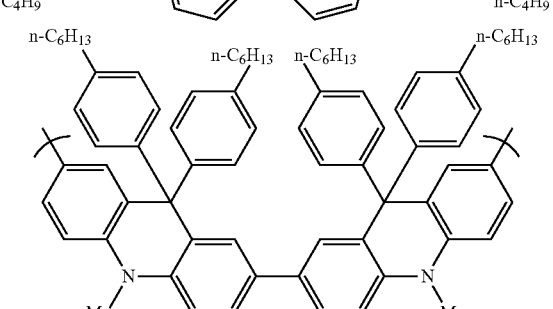
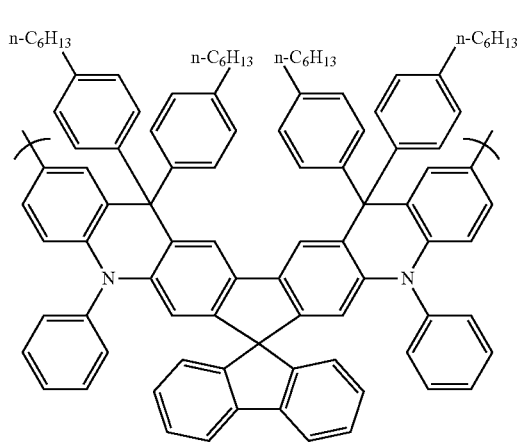

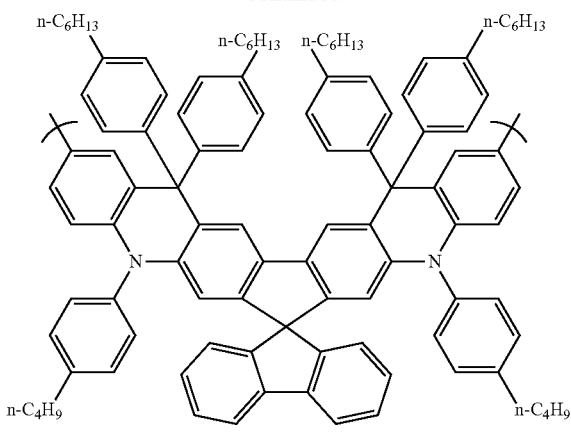

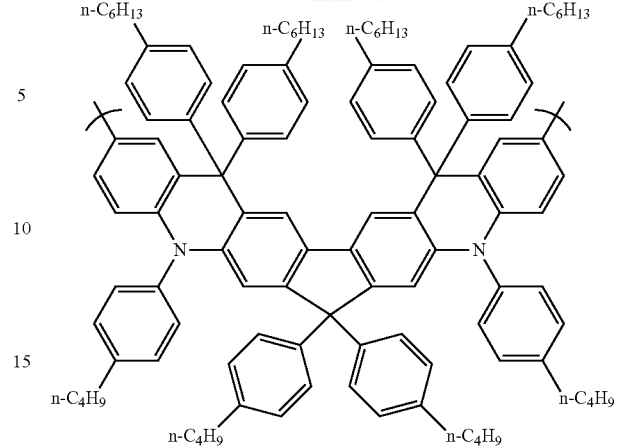

Of the above-described polymer compounds comprising the repeating units represented by formula (2), a polymer compound comprising a repeating unit represented by the following formula (3) is preferred.

[Chemical formula 30]

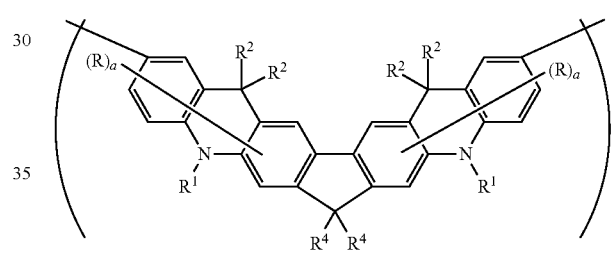

(3)

wherein the definitions of $R^1$, $R^2$, $R^3$, $R^4$ and a are the same as the definitions for the above-described formula (2).)

Preferably, from the viewpoint of the brightness half-life of a light-emitting device using the polymer compound of the present invention, the polymer compound further comprises a repeating unit represented by the following formula (4).

[Chemical formula 31]

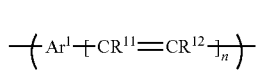

(4)

wherein
Ar$^1$ represents an arylene group or a divalent heterocyclic group, each of these groups optionally having a substituent;
$R^{11}$ and $R^{12}$ each independently represent a hydrogen atom, an alkyl group, an aryl group, a monovalent heterocyclic group, or a cyano group, each of these groups optionally having a substituent; and
n represents 0 or 1.

In the above-described formula (4), the arylene group represented by Ar$^1$ is generally an arylene group having 6 to 60 carbon atoms, and examples of such an arylene group may include a phenylene group (formulae 1 to 3 below), a naphthalenediyl group (formulae 4 to 13 below), an anthracenylene group (formulae 14 to 19 below), a biphenylene group

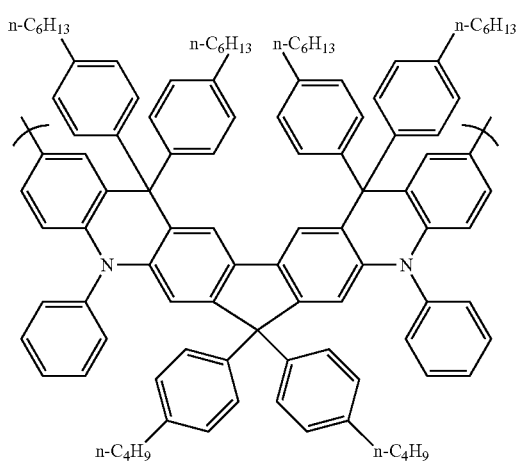

(formulae 20 to 25 below), a terphenylene group (formulae 26 to 28 below), and a condensed ring compound group (formulae 29 to 56 below). In these formulae, each R represents a hydrogen atom, an alkyl group, an alkoxy group, an aryl group, an aryloxy group, an arylalkyl group, an arylalkoxy group, an alkenyl group, an arylalkenyl group, an alkynyl group, an arylalkynyl group, an amino group, a silyl group, a halogen atom, an acyl group, an acyloxy group, a carbamoyl group, a monovalent heterocyclic group, a heterocyclyloxy group, a carboxyl group, a nitro group, or a cyano group. R' represents an alkyl group, an aryl group, or a monovalent heterocyclic group. The numbers of carbon atoms in R and R' are not included in the number of carbon atoms in the arylene group. The definitions of the groups and atoms represented by R and R' are the same as those described and exemplified for the groups and atoms represented by $R^3$.

[Chemical formula 32]

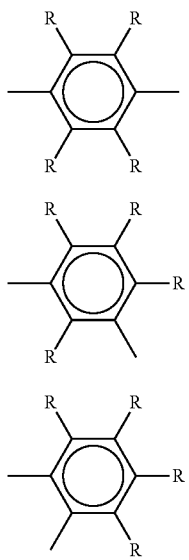

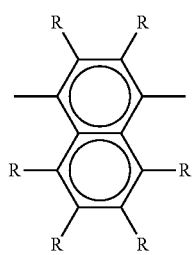

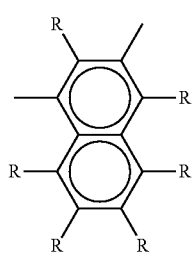

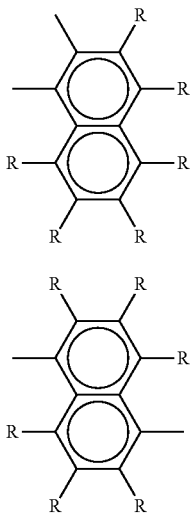

[Chemical formula 33]

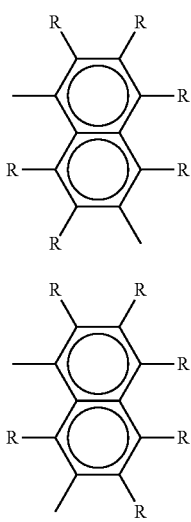

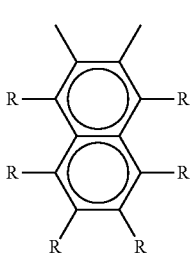

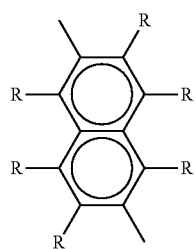
12
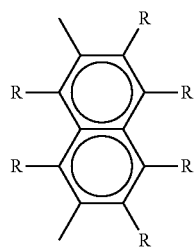
13
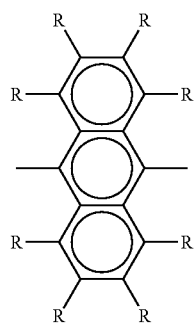
14
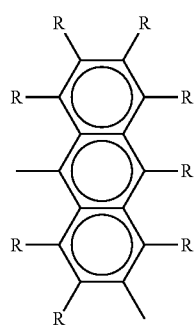
15
[Chemical formula 34]
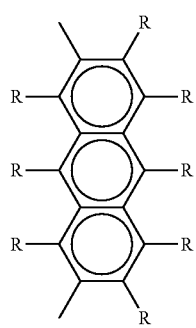
16
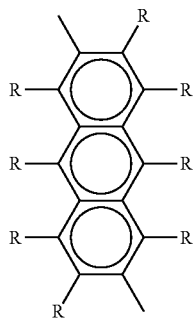
17
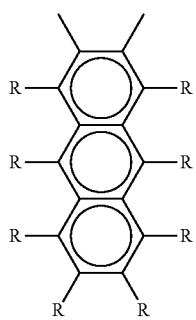
18
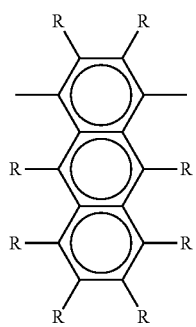
19
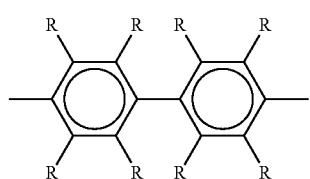
20
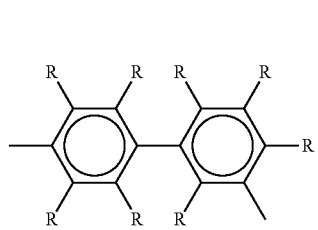
21
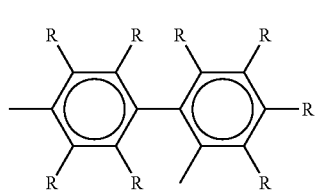
22

-continued
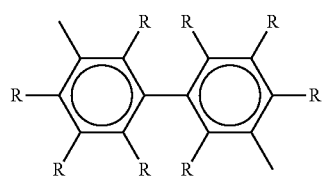
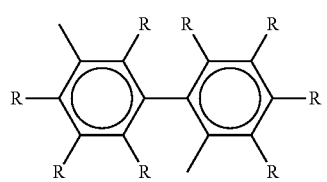
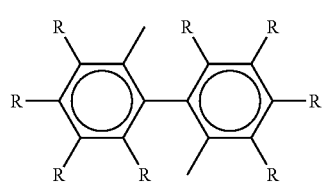
[Chemical formula 35]
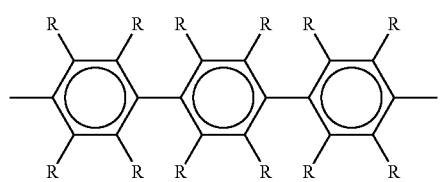
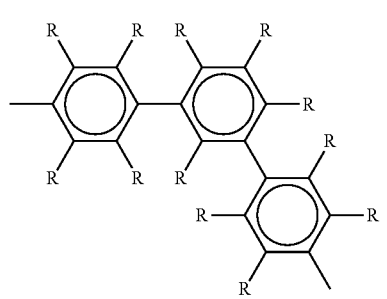
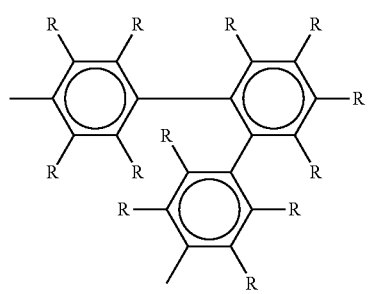
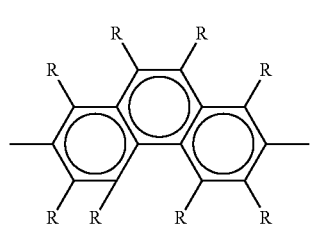
[Chemical formula 36]
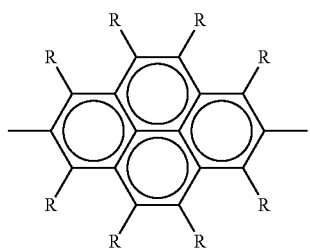
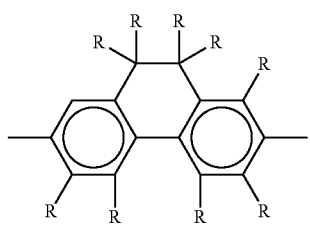
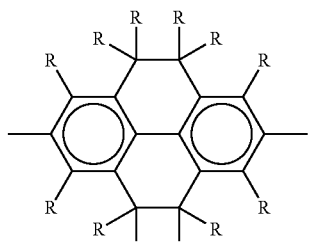
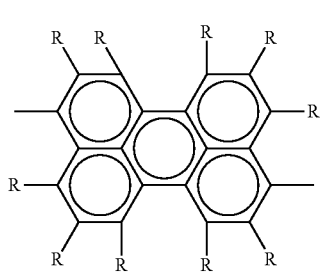
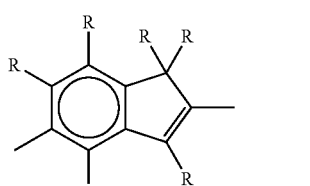
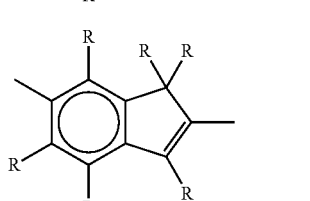
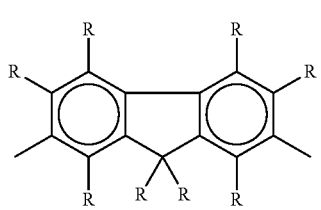

-continued
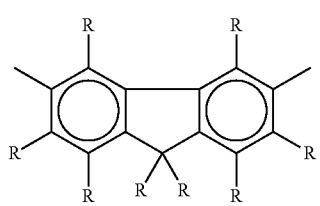
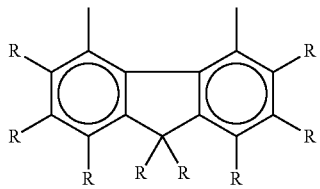
[Chemical formula 37]
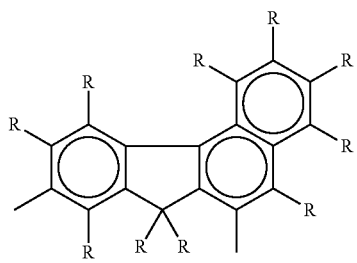
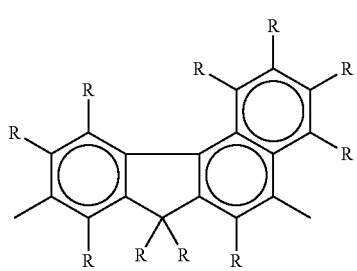
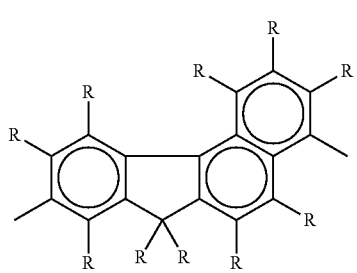
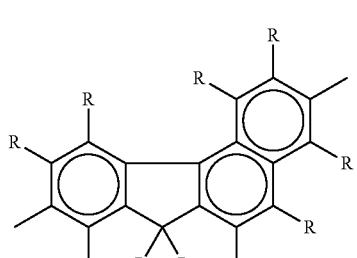
-continued
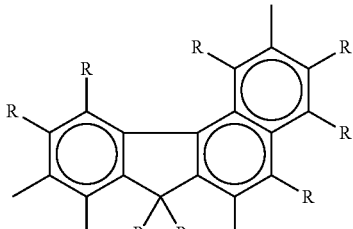
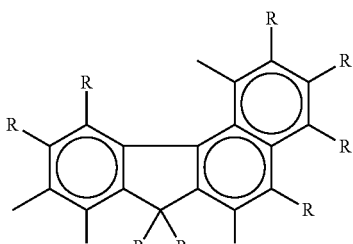
[Chemical formula 38]
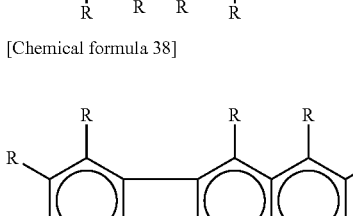
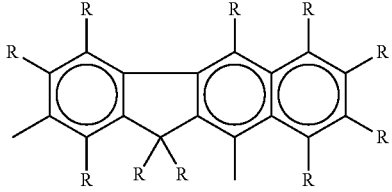
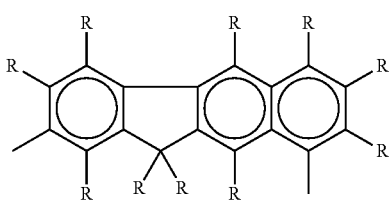
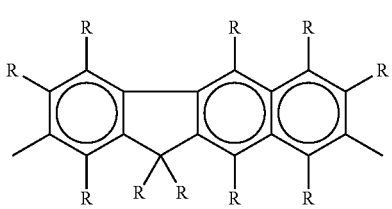
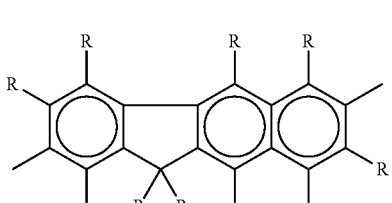
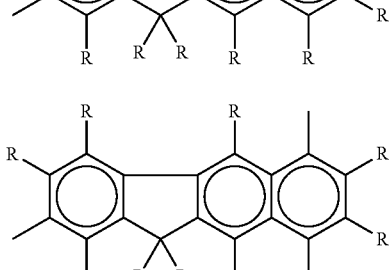

[Chemical formula 39]

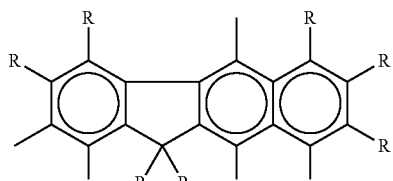

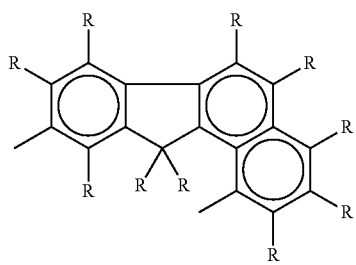

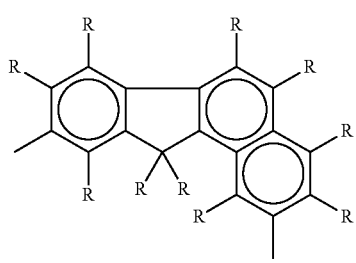

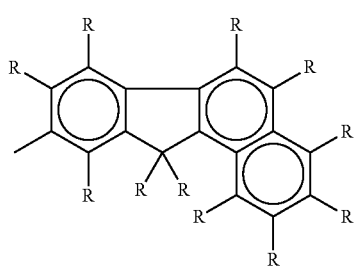

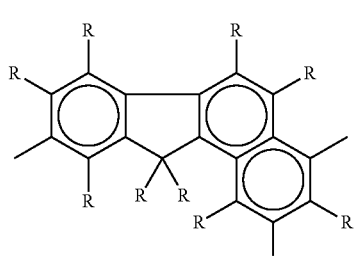

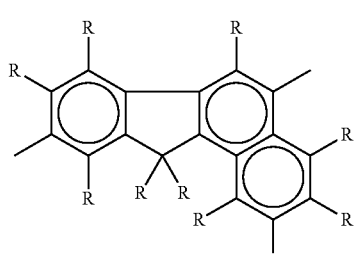

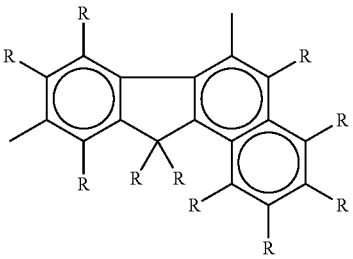

In the above-described formula (4), the divalent heterocyclic group represented by $Ar^1$ means a remaining atomic group obtained by removing two hydrogen atoms from a heterocyclic compound. The divalent heterocyclic group is preferably a divalent aromatic heterocyclic group. The number of carbon atoms in the divalent heterocyclic group is generally 2 to 60, and examples of such a divalent heterocyclic group may include groups represented by the following formulae. The number of carbon atoms in each R is not included in the number of carbon atoms in the divalent heterocyclic group.

Divalent heterocyclic groups including nitrogen as a heteroatom, such as pyridinediyl groups (formulae 57 to 62 below), diazaphenylene groups (formulae 63 to 66 below), quinolinediyl groups (formulae 67 to 81 below), quinoxalinediyl groups (formulae 82 to 86 below), a phenoxazinediyl group (formula 87 below), a phenothiazinediyl group (formula 88 below), acridinediyl groups (formulae 89 to 90 below), bipyridyldiyl groups (formulae 91 to 93 below), and phenanthrolinediyl groups (formulae 94 to 96 below);

groups including a heteroatom such as a silicon atom, a nitrogen atom, a sulfur atom or a selenium atom, and having a cross-linked biphenyl structure (formulae 97 to 126 below);

5-membered heterocyclic groups including a heteroatom such as a silicon atom, a nitrogen atom, a sulfur atom, or a selenium atom (formulae 127 to 132 below);

5-membered condensed heterocyclic groups including a heteroatom such as a silicon atom, a nitrogen atom, a sulfur atom, or a selenium atom (formulae 133 to 142 below), for example, a benzothiadiazole-4,7-diyl group and a benzoxadiazole-4,7-diyl group;

groups including 5-membered heterocyclic groups each including a heteroatom such as a silicon atom, a nitrogen atom, a sulfur atom or a selenium atom, the 5-membered heterocyclic groups being linked at the a positions to the heteroatoms to form a dimer or an oligomer (formulae 143 and 144 below);

groups each including phenyl groups and a 5-membered heterocyclic group including a heteroatom such as a silicon atom, a nitrogen atom, a sulfur atom, or a selenium atom, the phenyl groups being linked to the 5-membered heterocyclic group at the α positions to a heteroatom (formulae 145 to 151 below); and tricyclic groups in which a condensed heterocyclic group including a heteroatom such as a nitrogen atom, an oxygen atom or a sulfur atom is linked to benzene rings or monocyclic heterocyclic groups (formulae 152 to 157 below).

[Chemical formula 40]
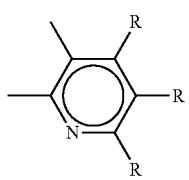 57
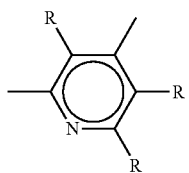 58
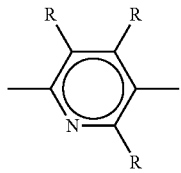 59
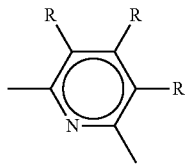 60
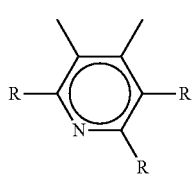 61
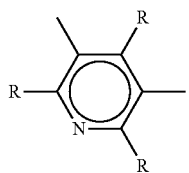 62
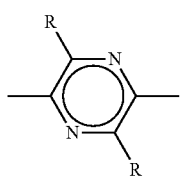 63
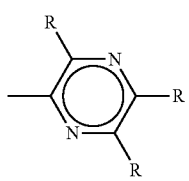 64
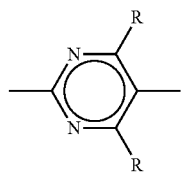 65
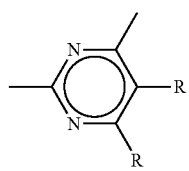 66
[Chemical formula 41]
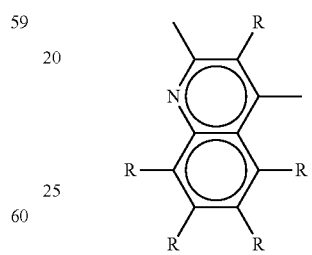 67
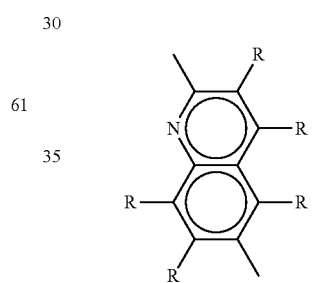 68
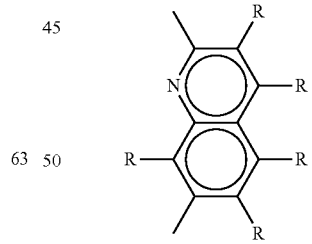 69
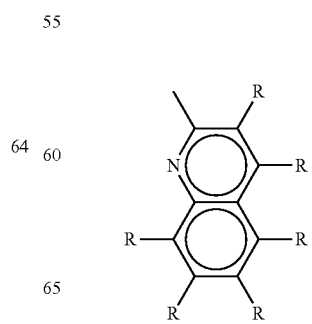 70

[Chemical formula 42]
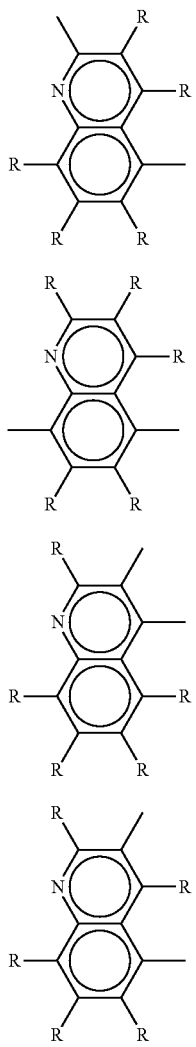
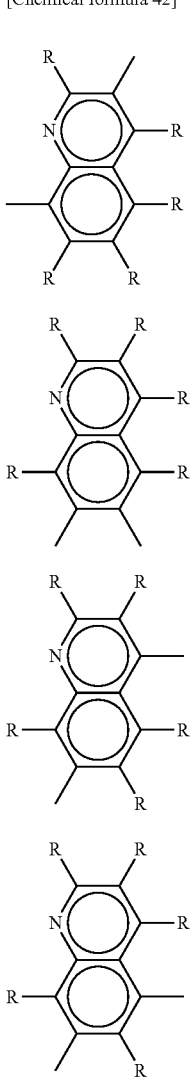
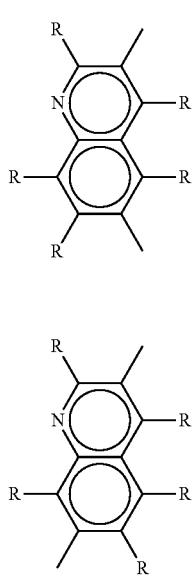
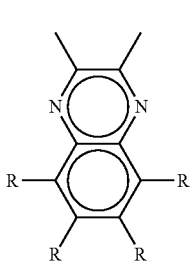

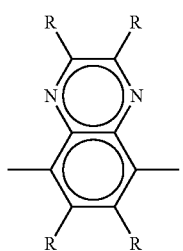
83
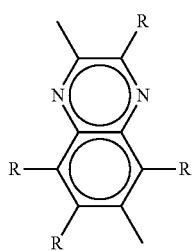
84
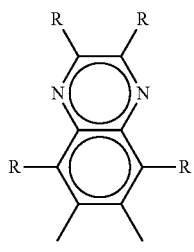
85
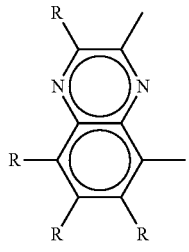
86
[Chemical formula 43]
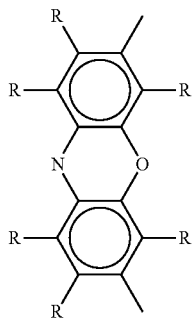
87
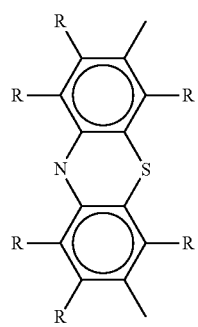
88
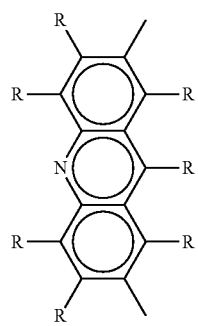
89
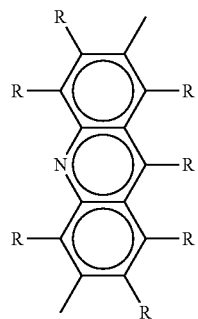
90
[Chemical formula 44]
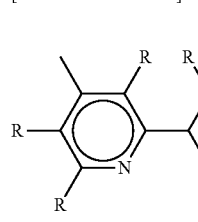
91
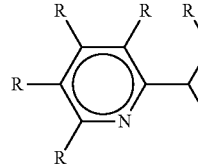
92
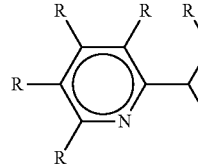
93

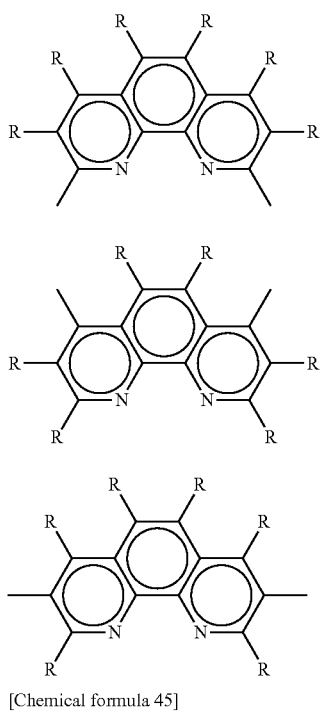
[Chemical formula 45]
[Chemical formula 46]
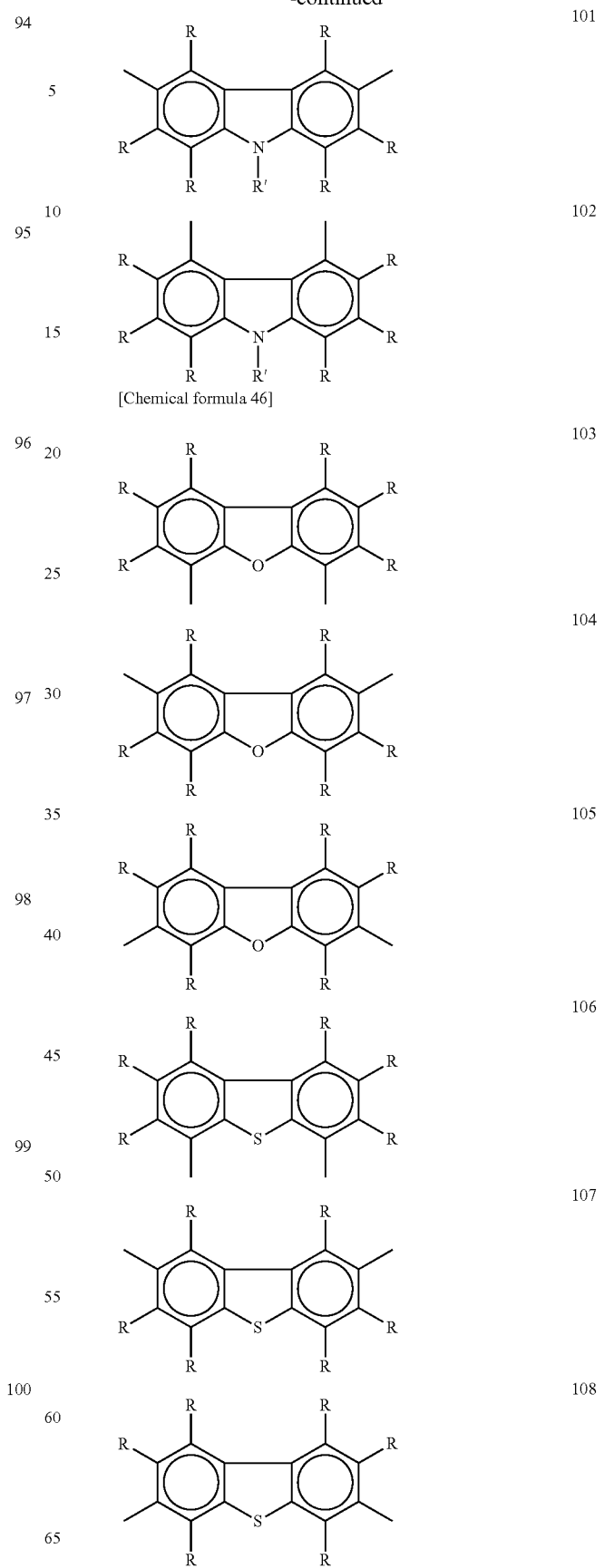

-continued
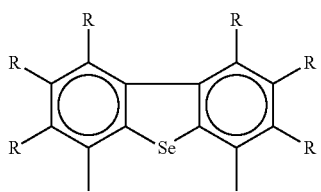
109
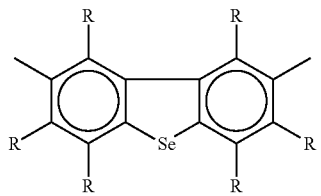
110
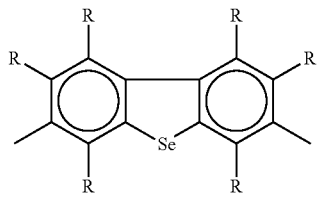
111
[Chemical formula 47]
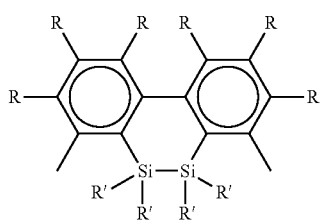
112
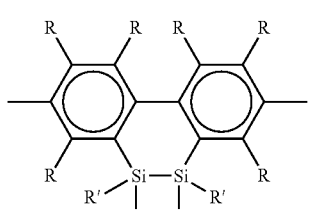
113
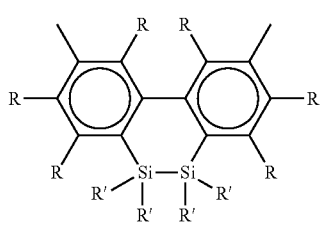
114
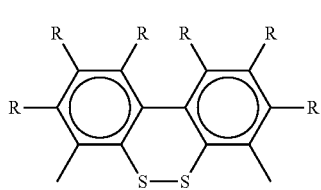
115
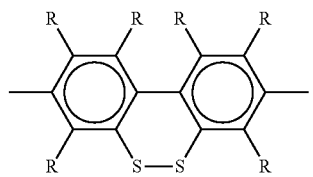
116
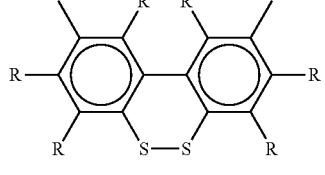
117
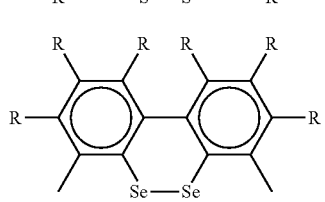
118
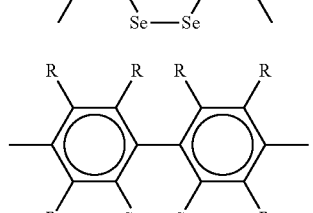
119
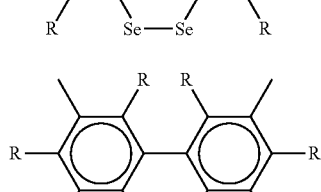
120
[Chemical formula 48]
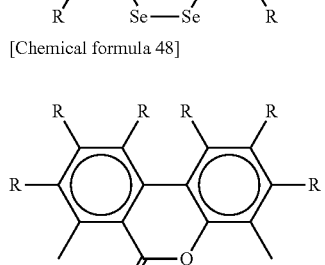
121
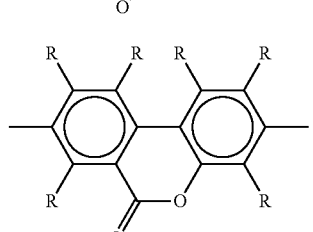
122
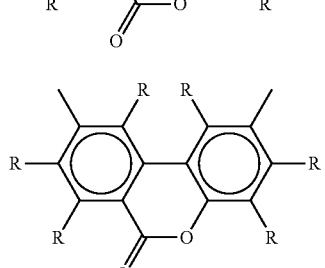
123

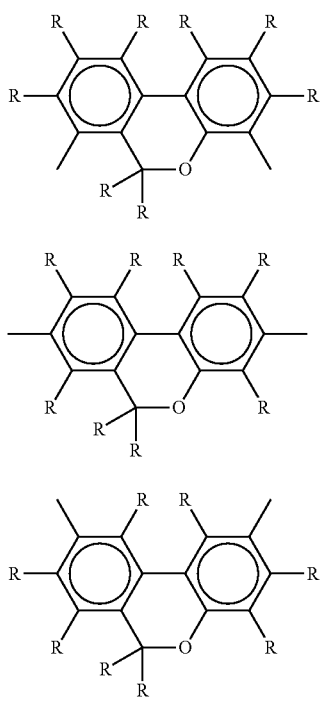
[Chemical formula 49]
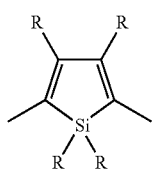
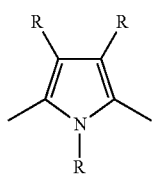
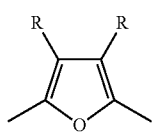
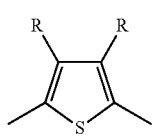
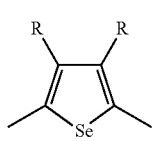
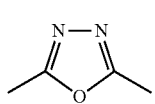
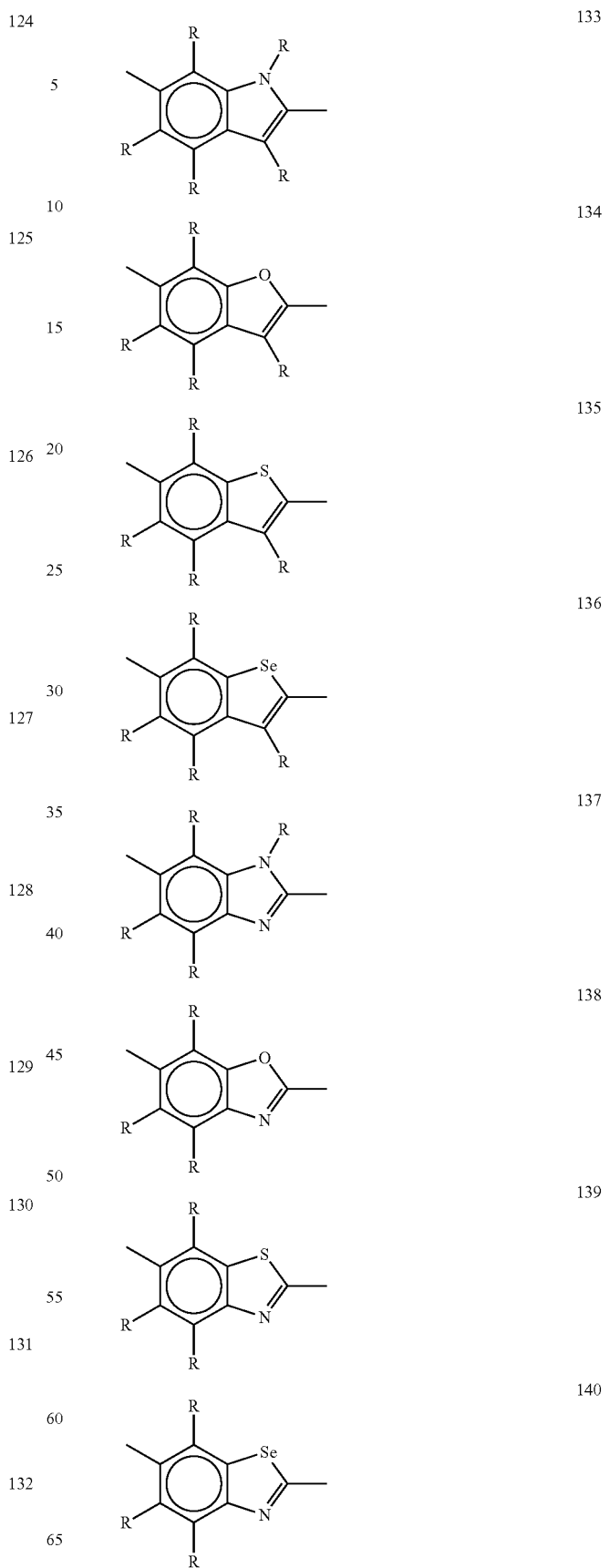

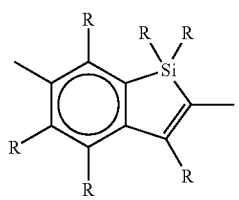
141
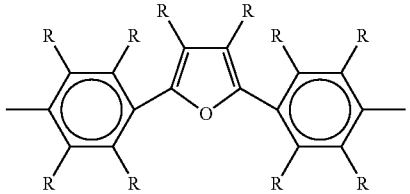
148
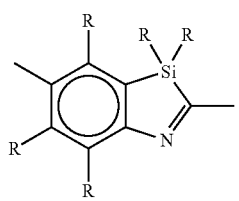
142
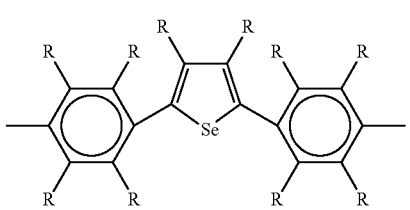
149
[Chemical formula 50]
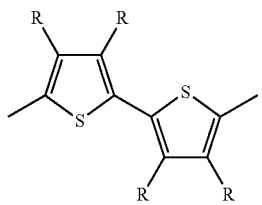
143
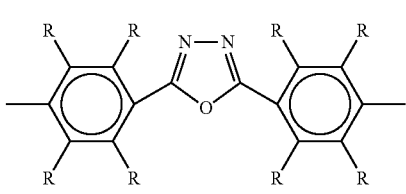
150
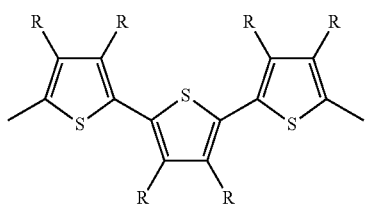
144
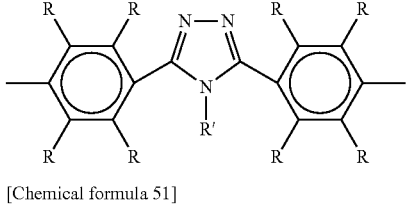
151
[Chemical formula 51]
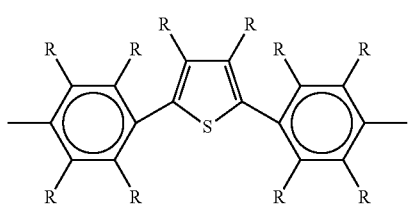
145
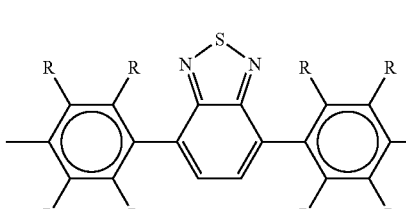
152
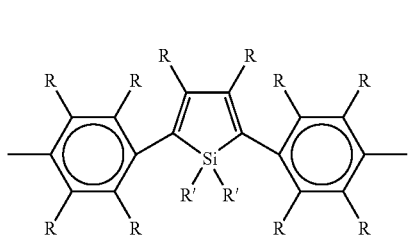
146
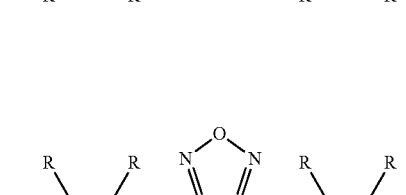
153
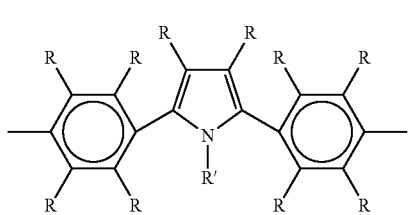
147
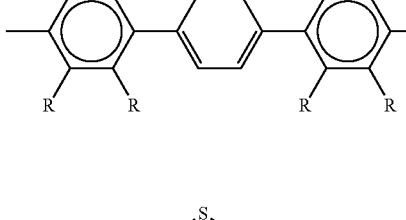
154
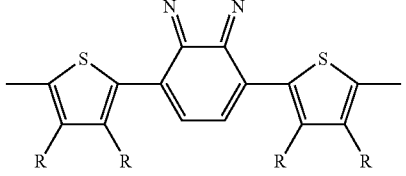

-continued

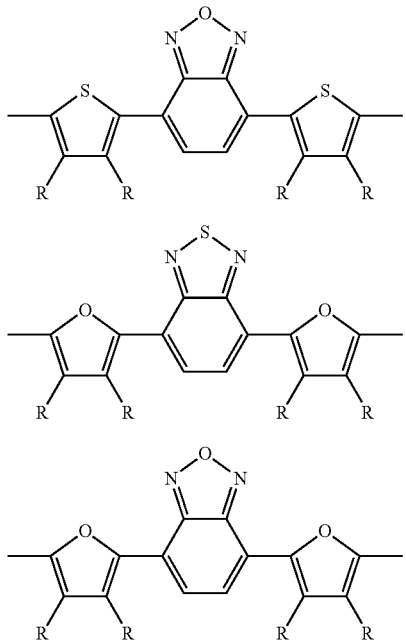

155

156

157

In the above-described formula (4), the alkyl group, the aryl group, and the monovalent heterocyclic group represented by $R^{11}$ and $R^{12}$ are the same as those described and exemplified for $R^1$.

Preferably, the above-described repeating unit represented by formula (4) is a repeating unit with n=0. More preferably, from the viewpoint of the stability of the polymer compound, the repeating unit represented by formula (4) is a repeating unit in which n=0 and $Ar^1$ is an arylene group or a divalent aromatic heterocyclic group. Particularly preferably, the repeating unit is a repeating unit represented by the following formula (5).

[Chemical formula 52]

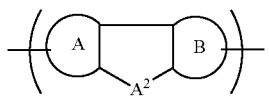

(5)

wherein
a ring A and a ring B each independently represent an aromatic hydrocarbon ring or an aromatic heterocyclic ring, each of these rings optionally having a substituent; and
$A^2$ represents a linking group.

The ring A and ring B are each preferably an aromatic hydrocarbon ring. Examples of the aromatic hydrocarbon ring may include a benzene ring, a naphthalene ring, and an anthracene ring, and a benzene ring is preferred.

The linking group represented by $A^2$ is preferably —$C(R^{13})_2$—. $R^{13}$ will be described later.

Preferably, the above-described repeating unit represented by formula (5) is a repeating unit represented by the following formula (6).

[Chemical formula 53]

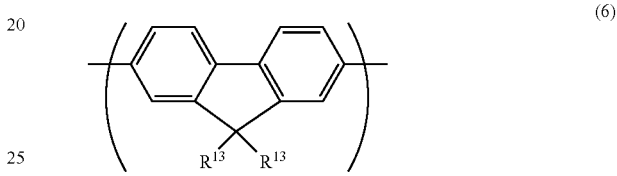

(6)

wherein
each $R^{13}$ represents a hydrogen atom, an alkyl group, an aryl group, an arylalkyl group, or a monovalent heterocyclic group, each of these groups optionally having a substituent;
the $R^{13}$s may be the same or different; and
the two $R^{13}$ may be connected to form a ring.

In the above-described formula (6), the alkyl group, the aryl group, the arylalkyl group, and the monovalent heterocyclic group represented by $R^{13}$ are the same as those described and exemplified for $R^1$. Preferably, the two $R^{13}$ do not form a ring.

From the viewpoint of the characteristics of a device used as a light-emitting device, the repeating unit represented by formula (6) is preferably a repeating unit in which each $R^{13}$ is an alkyl group, an aryl group, or an arylalkyl group. From the viewpoint of the solubility of the polymer compound in a solvent, a repeating unit in which each $R^{13}$ is an alkyl group having 4 or more carbon atoms is preferred.

Examples of the above-described repeating unit represented by formula (6) may include repeating units represented by the following formulae.

[Chemical formula 54]

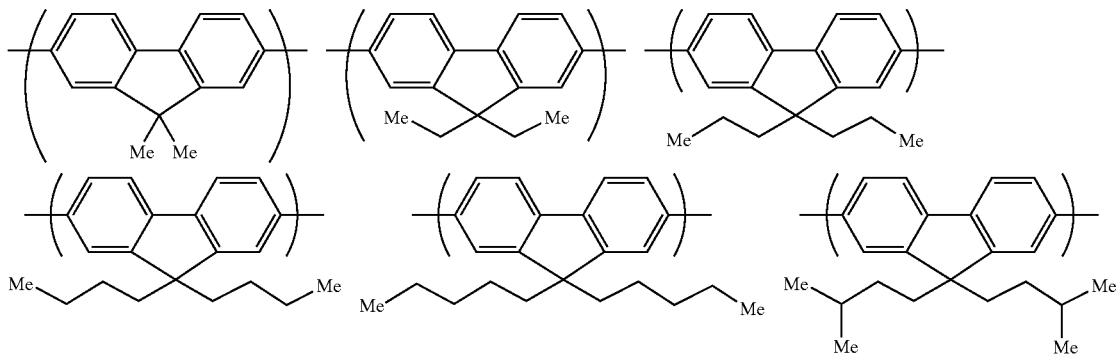

63 64
-continued
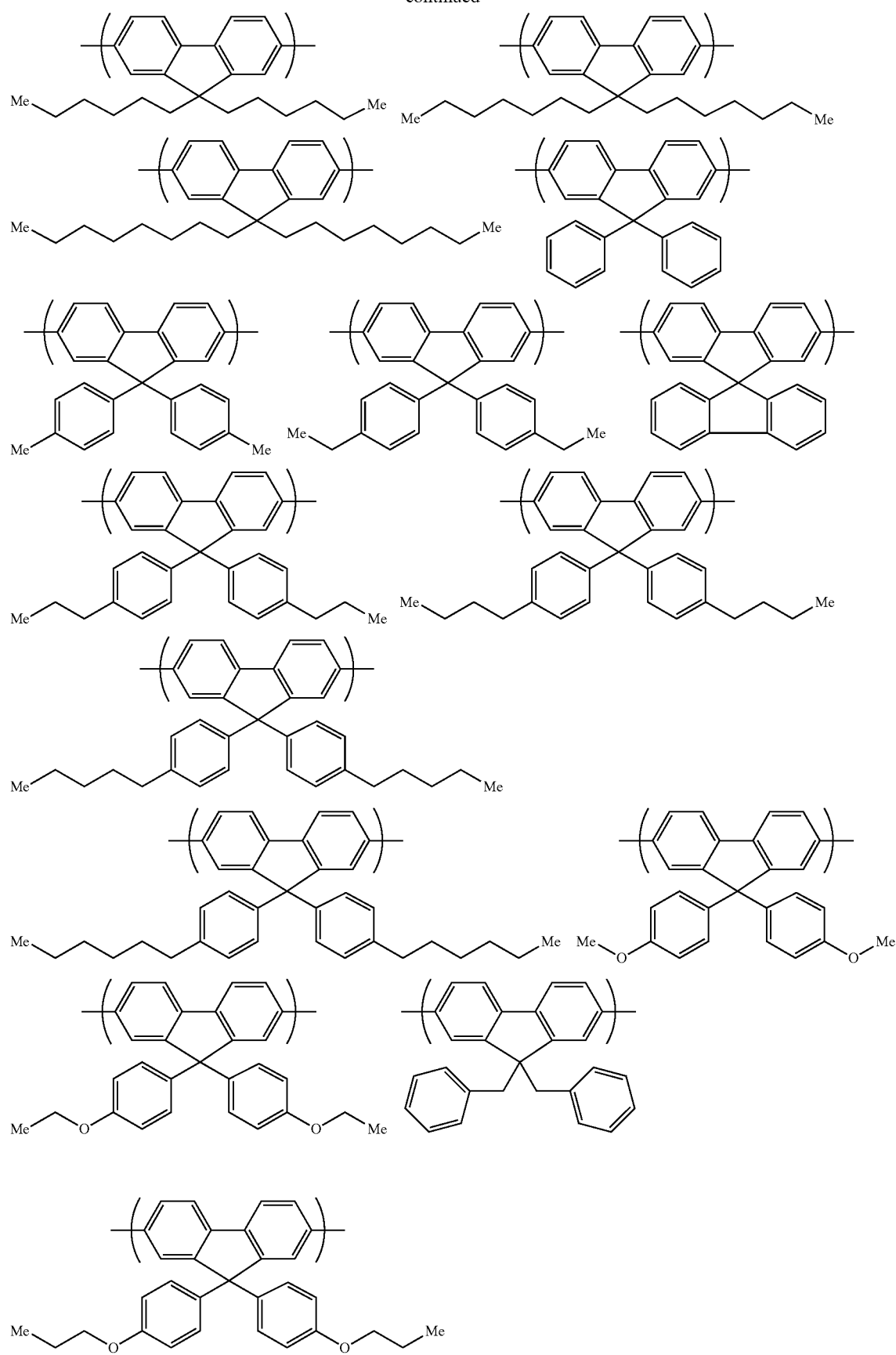

-continued
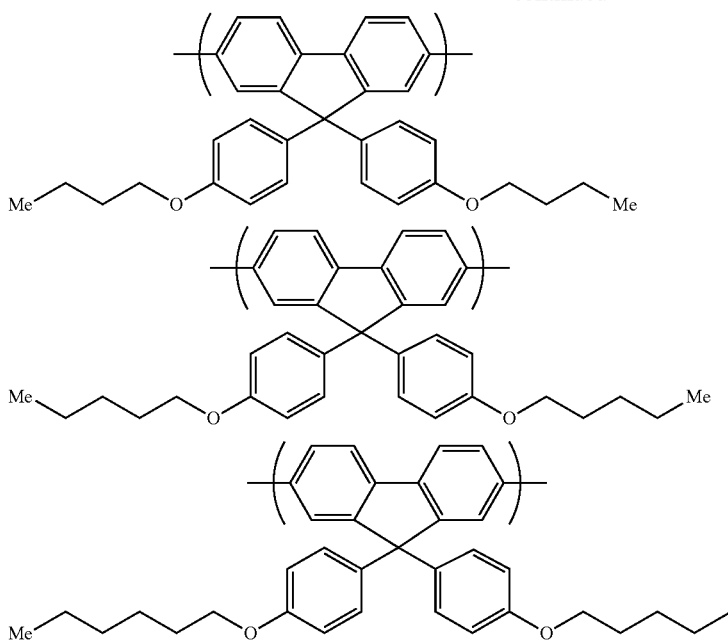
[Chemical formula 55]
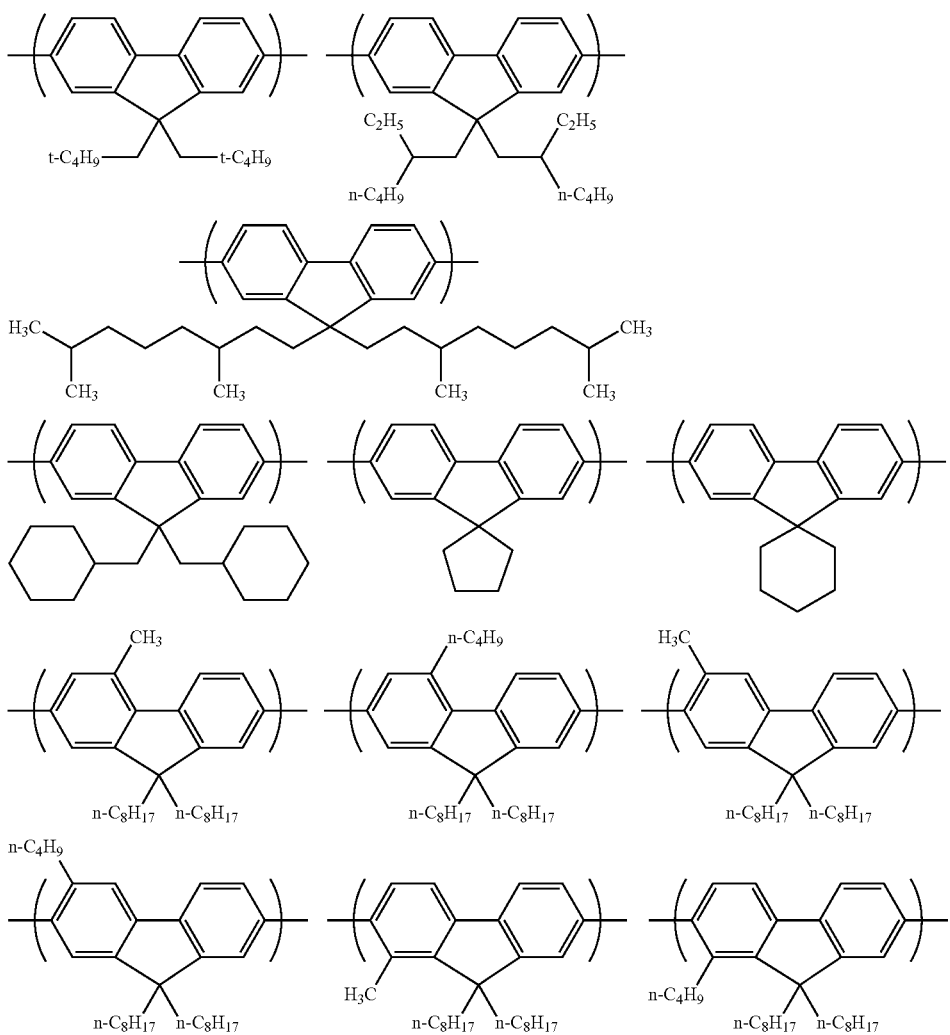

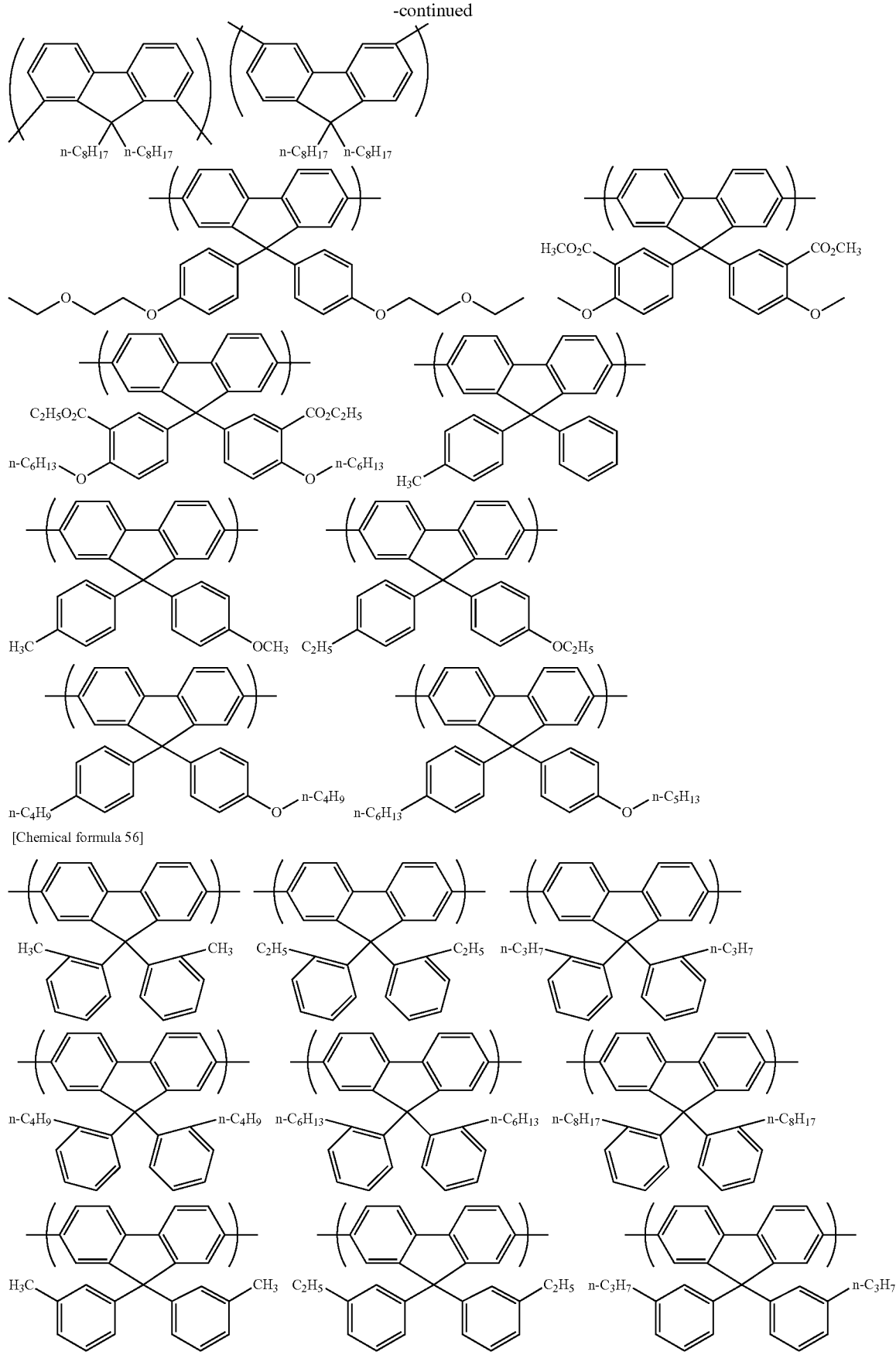
[Chemical formula 56]

-continued
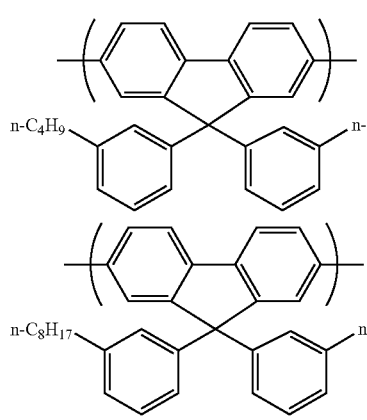
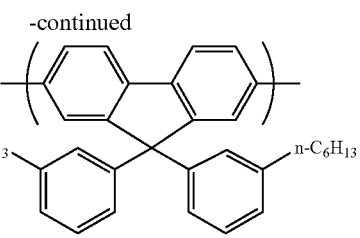
[Chemical formula 57]
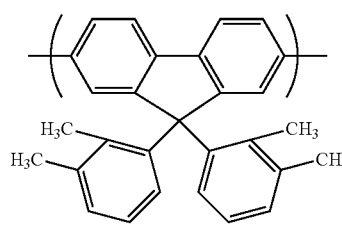
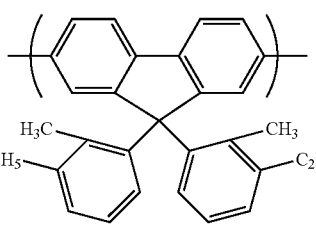
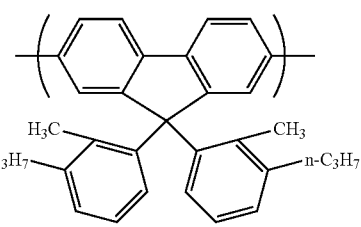
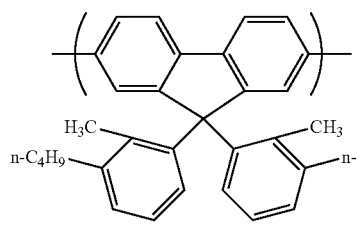
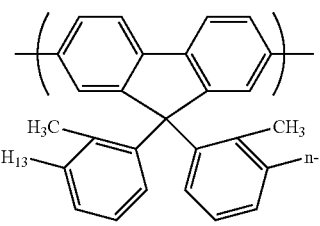
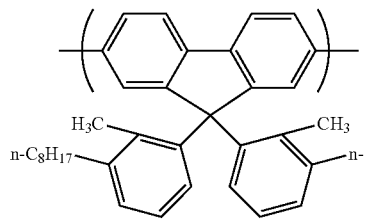
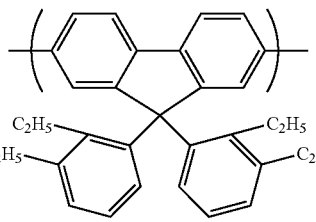
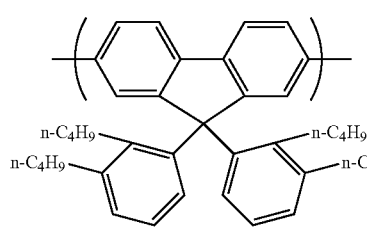
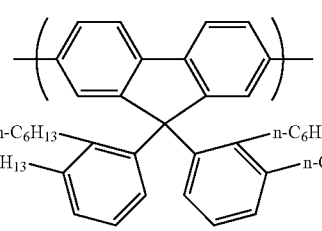
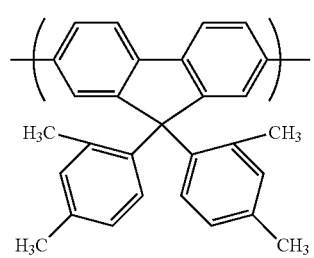
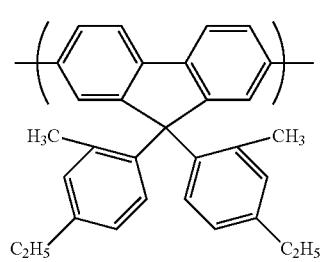
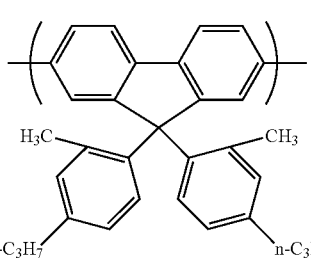
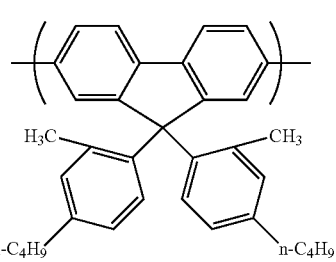

-continued
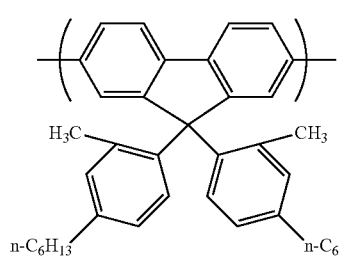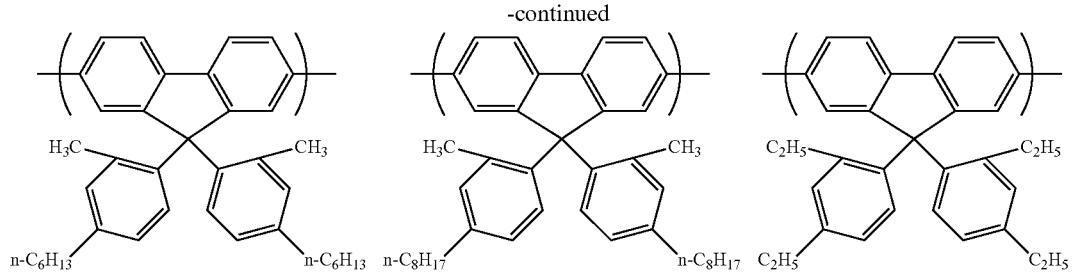
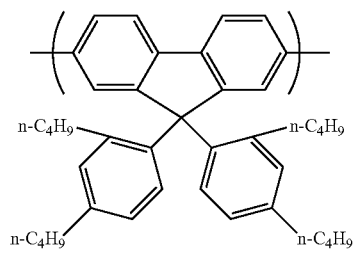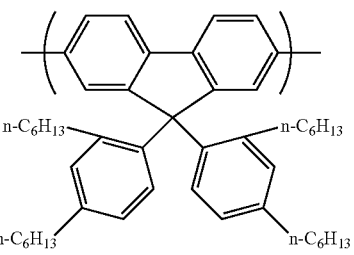
[Chemical formula 58]
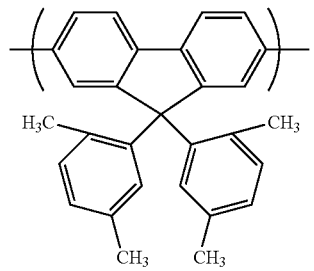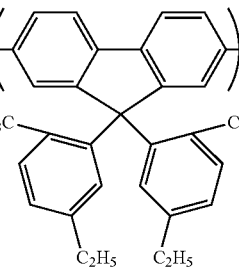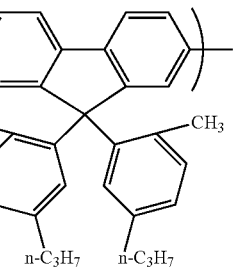
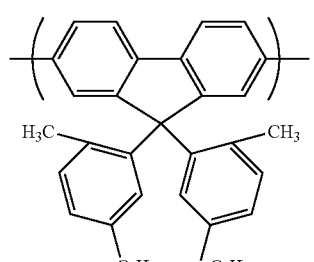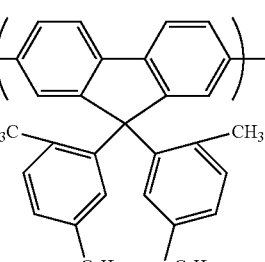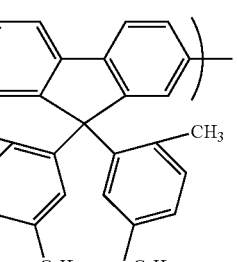
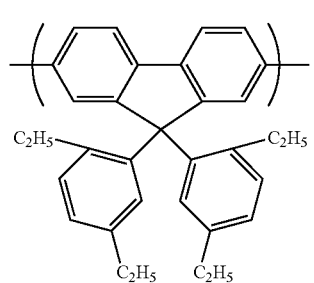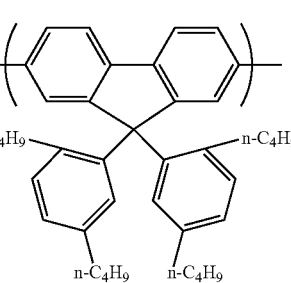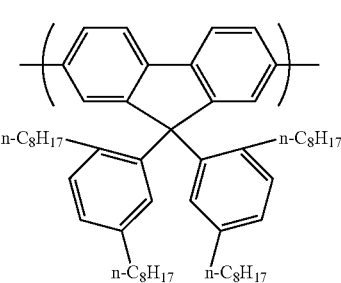
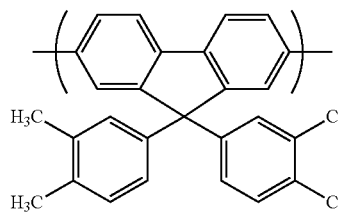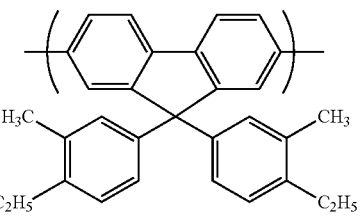

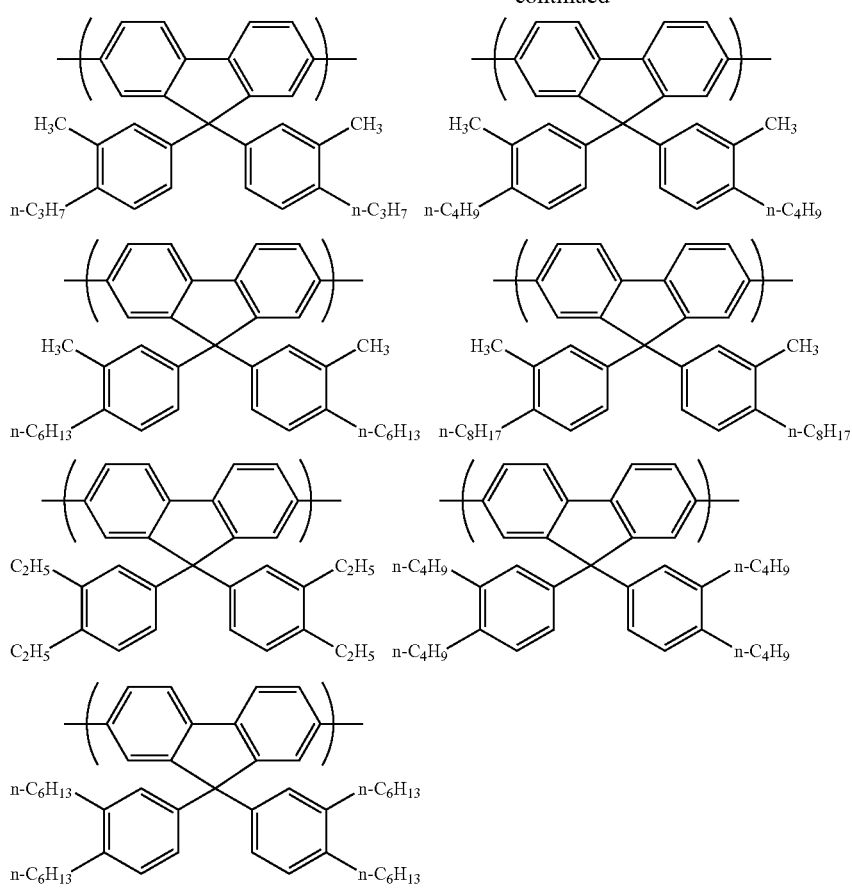
[Chemical formula 59]
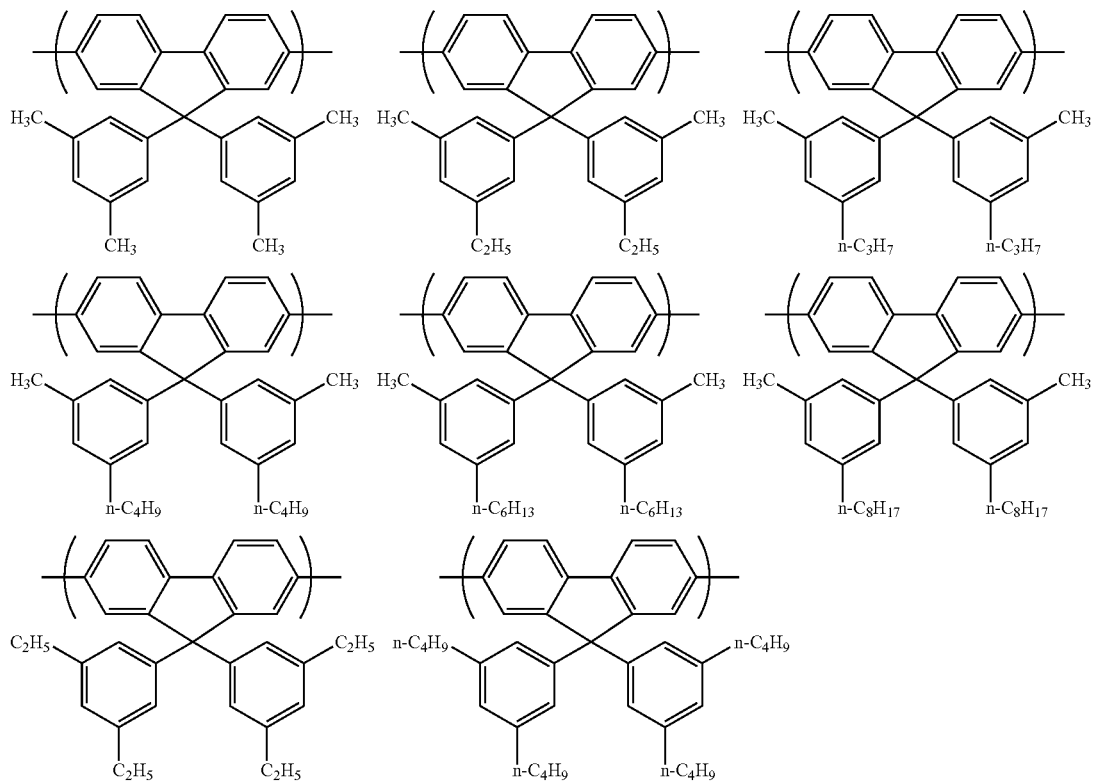

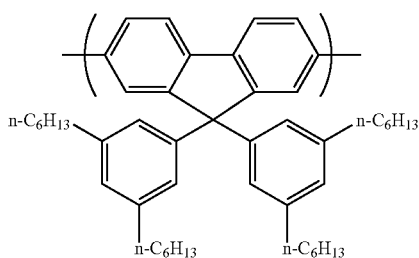

The polymer compound of the present invention may comprise only one type of the repeating units represented by formula (4), (5), or (6) or may comprise two or more types thereof.

From the viewpoint of the color purity of the polymer compound of the present invention when it is used as a blue material, each of the substituents in the residue obtained by removing at least one hydrogen atom from the above-described structure represented by formula (1) and in the above-described repeating unit represented by formula (4) is preferably an alkyl group, an aryl group, or an arylalkyl group.

Preferably, from the viewpoint of charge injection-transport property when the polymer compound of the present invention is formed into a film and from the viewpoint of characteristics of a device used as a light-emitting device, the polymer compound is a conjugated macromolecule. The conjugated macromolecule means a polymer compound in which non-localized n electron pairs are present along the skeleton of the main chain of the polymer compound. Such conjugated polymers also include polymer compounds in which unpaired electrons or lone electron-pairs participate in resonance instead double bonds.

In the polymer compound of the present invention, repeating units may be linked through a non-conjugated unit, and each repeating unit may include the non-conjugated unit, so long as a certain characteristic is not impaired. Examples of the non-conjugated unit may include one of the following groups and combinations of two or more thereof.

[Chemical formula 60]

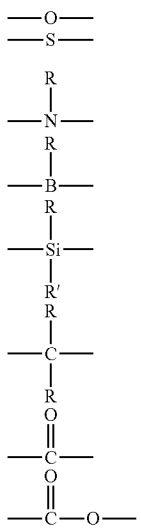

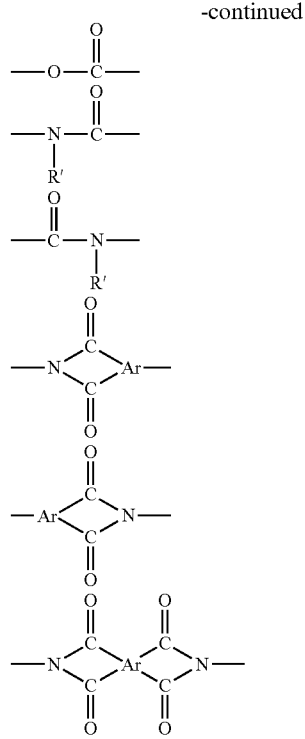

wherein R and R are the same as described above, and Ar represents an aromatic hydrocarbon group or an aromatic heterocyclic group.

The polymer compound of the present invention may be a random copolymer, a block copolymer, a graft copolymer, or a polymer compound having a structure intermediate between them, for example, a random copolymer having properties of a block copolymer, or may be a polymer having a branch in their main chain and at least three terminal ends, or dendrimer.

When the polymer compound of the present invention is used for the production of a light-emitting device and an additional layer is stacked on a film comprising the polymer compound by a coating method, it is preferable that the polymer compound comprises a cross-linkable group. When the polymer compound comprises such a cross-linkable group, the compound can be cross-linked by treatment with heat or light. Therefore, the layer comprising the cross-linked polymer compound can be prevented from dissolving in a solvent when the additional layer is applied, so that the additional layer is easily stacked. Examples of the cross-linkable group may include groups represented by the following formulae (Z-1) to (Z-12).

[Chemical formula 61]

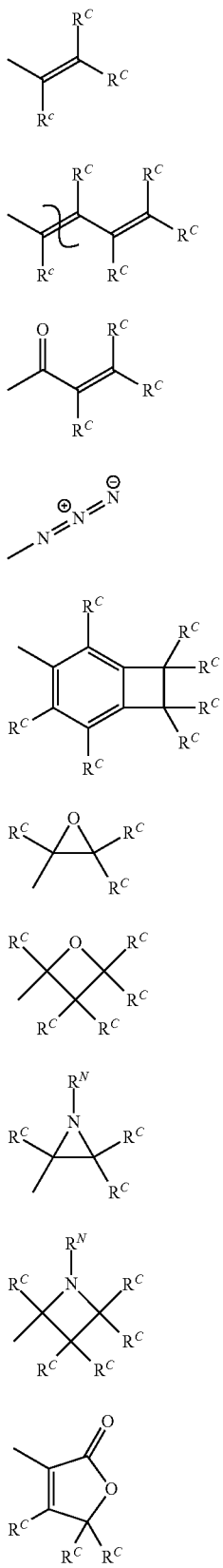

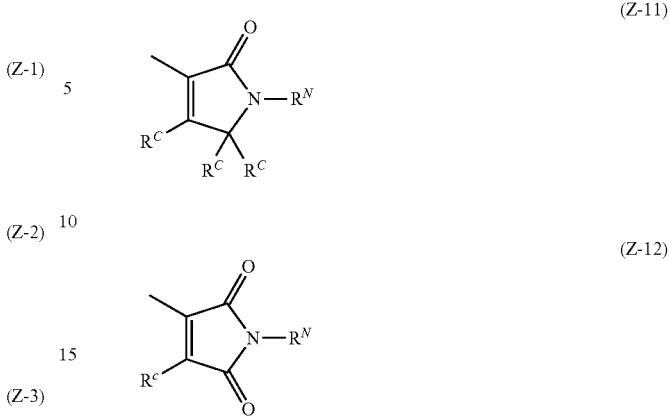

-continued

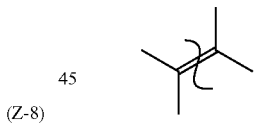

In formulae (Z-1) to (Z-12), each $R^C$ represents a hydrogen atom, an alkyl group, an alkoxy group, an alkylthio group, an aryl group, an aryloxy group, an arylthio group, an arylalkyl group, an arylalkoxy group, an arylalkylthio group, an amino group, a silyl group, a halogen atom, an acyl group, an acyloxy group, an imine residue, a carbamoyl group, an acid imido group, a monovalent heterocyclic group, a carboxyl group, a cyano group, or a nitro group;

each $R^N$ represents an alkyl group, an aryl group, an arylalkyl group, an acyl group, or a monovalent heterocyclic group;

the groups represented by $R^C$ and $R^N$ optionally have a substituent; and the $R^C$s may be the same or different.

In the above-described formula (Z-2), the double bond with a wavy line represented by the following formula:

[Chemical formula 62]

means that the group may be any of E form or Z form.

When the polymer compound of the present invention comprises a repeating unit comprising a cross-linkable group, the repeating unit may comprise one type of cross-linkable group or may comprise two or more types of cross-linkable groups. The cross-linkable group is preferably any of the above-described groups represented by formulae (Z-1), (Z-2), and (Z-5), and it is more preferable that each $R^C$ be a hydrogen atom.

The copolymerization ratio of the repeating unit comprising such a cross-linkable group is generally 0.1 to 50 percent by mole based on the total amount of repeating units, preferably 1 to 30 percent by mole, and more preferably 3 to 20 percent by mole.

When the polymer compound of the present invention comprises a repeating unit comprising a cross-linkable group, examples of the repeating unit may include the following repeating units.

[Chemical formula 63]
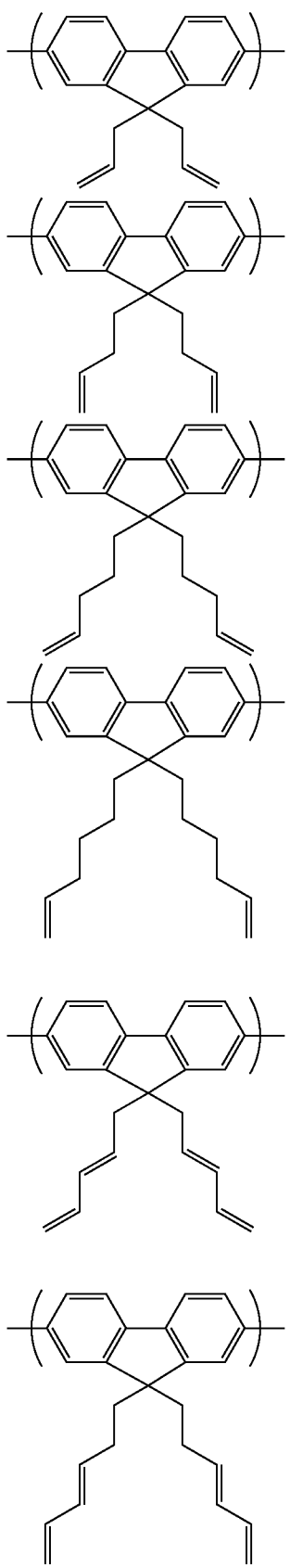
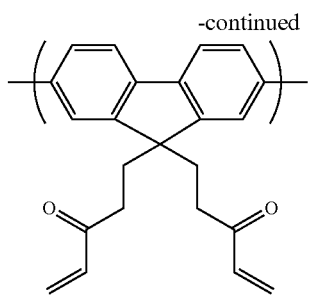
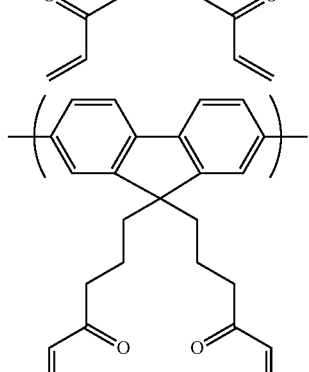
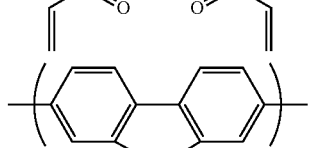
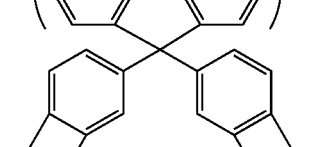
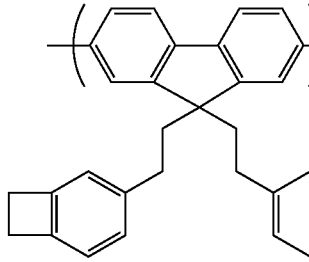
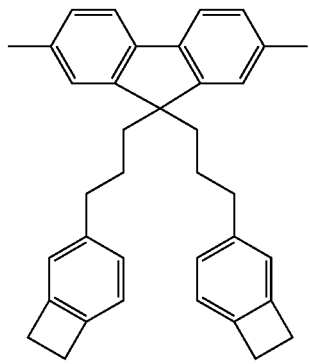

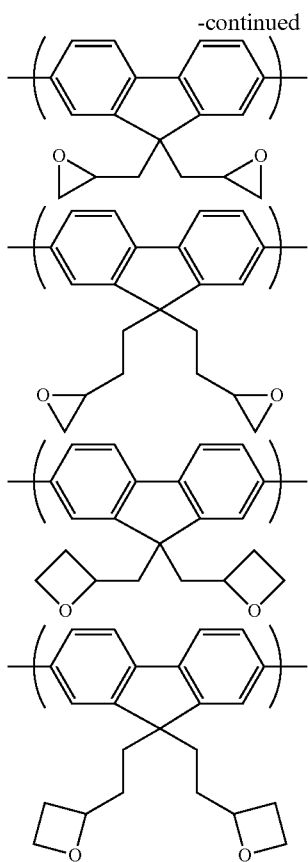

When the polymer compound of the present invention comprises the above-described repeating unit represented by formula (2), the amount of the repeating unit is preferably 0.1 to 50 percent by mole based on the total amount of repeating units and more preferably 0.5 to 30 percent by mole, from the viewpoint of the characteristics of a light-emitting device in which the polymer compound is used for the light-emitting layer of the device.

When the polymer compound of the present invention comprises the above-described repeating unit represented by formula (4), the ratio of the amount of this repeating unit to the total amount of repeating units is preferably 1 to 99.9 percent by mole and more preferably 50 to 99.5 percent by mole, from the viewpoint of the characteristics of a light-emitting device in which the polymer compound is used for the light-emitting layer of the device.

When the polymer compound of the present invention comprises the repeating unit represented by formula (6), the ratio of the amount of this repeating unit to the total amount of repeating units is preferably 1 to 99.9 percent by mole and more preferably 50 to 99.5 percent by mole, from the viewpoint of the characteristics of a light-emitting device in which the polymer compound is used for the light-emitting layer of the device and from the viewpoint of adjustment of the color of emitted light.

The number-average molecular weight of the polymer compound of the present invention in terms of polystyrene is preferably $2 \times 10^3$ to $1 \times 10^8$ and more preferably $1 \times 10^4$ to $1 \times 10^6$, from the viewpoint of the brightness half-life of a light-emitting device produced using the compound.

From the viewpoint of the color purity of the polymer compound of the present invention when it is used as a blue light-emitting material, the polymer compound is preferably a polymer compound comprising the repeating unit represented by formula (2) and the repeating unit represented by formula (4) and also preferably a polymer compound comprising the repeating unit represented by formula (2) and the repeating unit represented by formula (4) with n=0 and $Ar^1$ being an arylene group having 6 to 15 carbon atoms. Among them, the total amount of the repeating unit represented by formula (2) and the repeating unit represented by formula (4) is preferably 95 percent by mole or more based on the total amount of all the repeating units in the polymer compound, more preferably 99 percent by mole or more, and particularly preferably 99.9 percent by mole or more.

When the compound of the present invention is a low molecular compound, examples of such a compound may include the following compounds.

[Chemical formula 64]

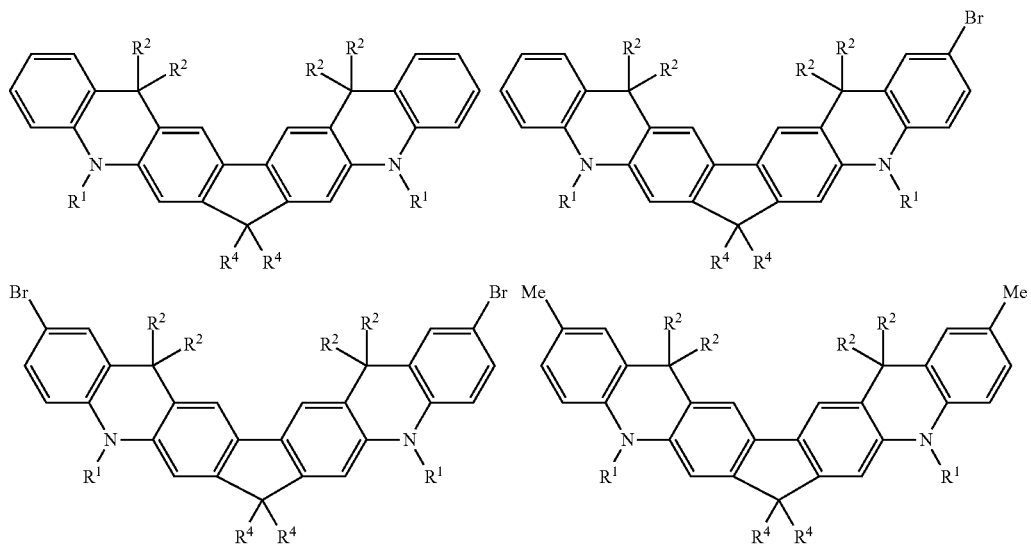

-continued
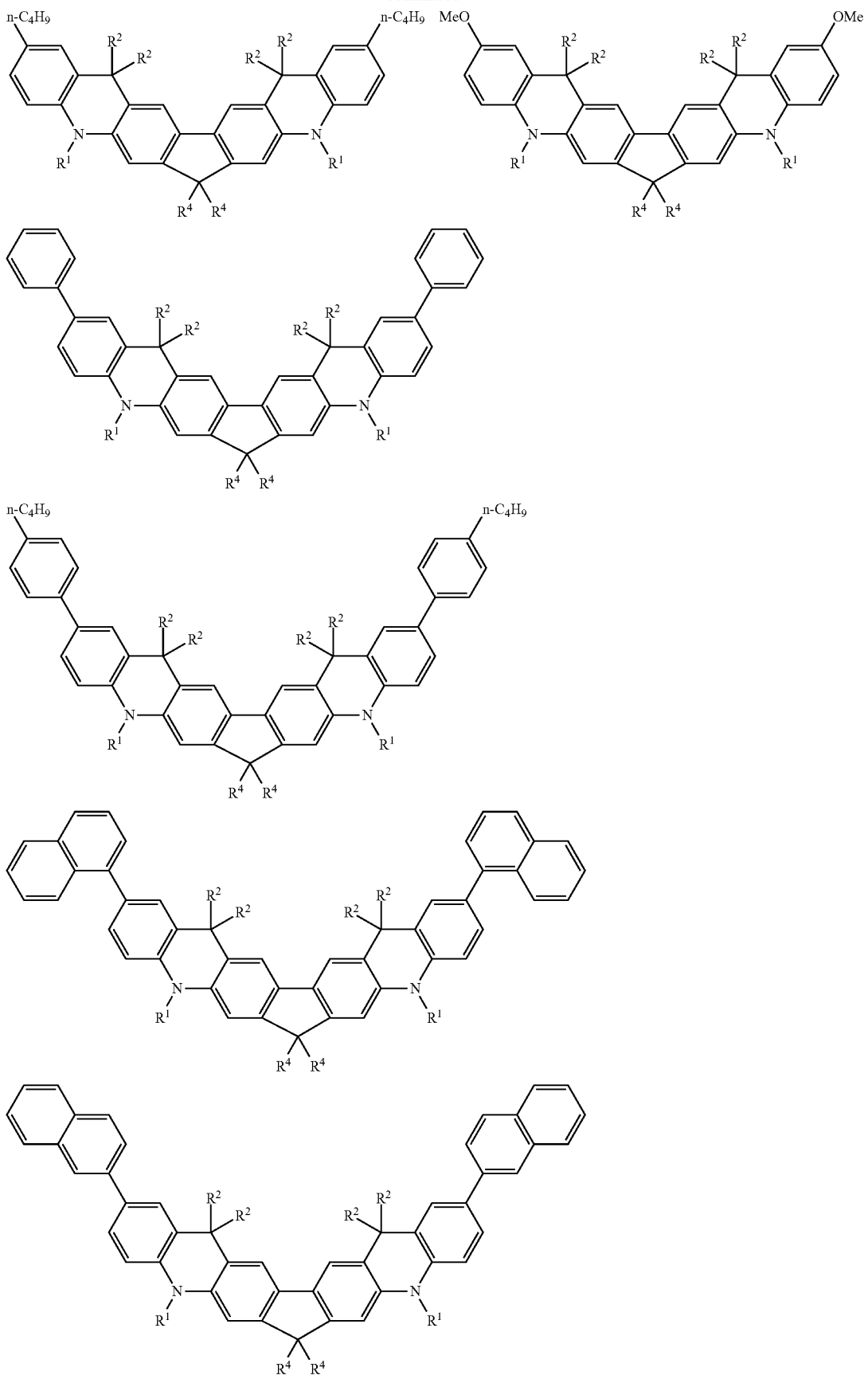

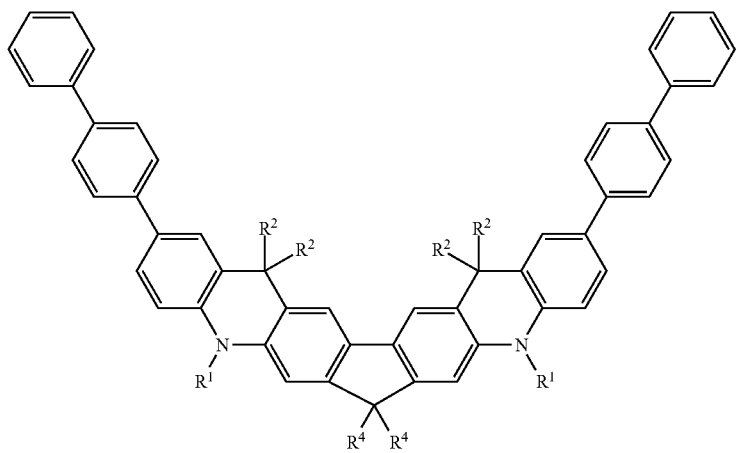
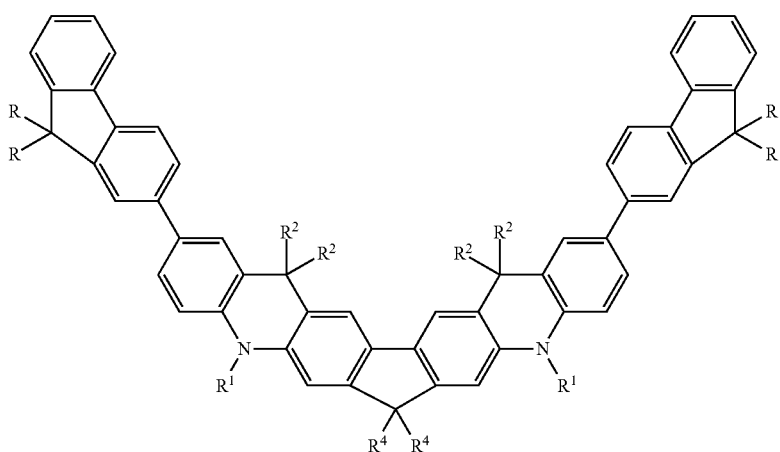
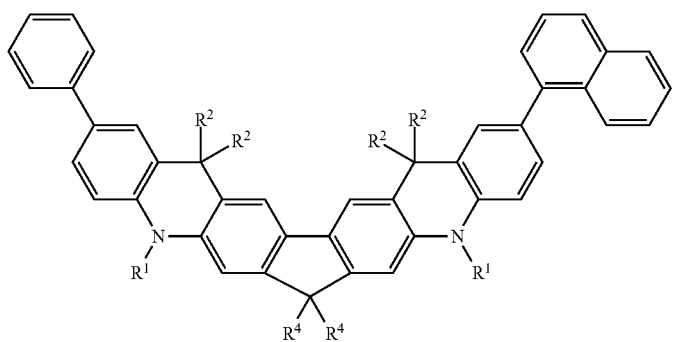
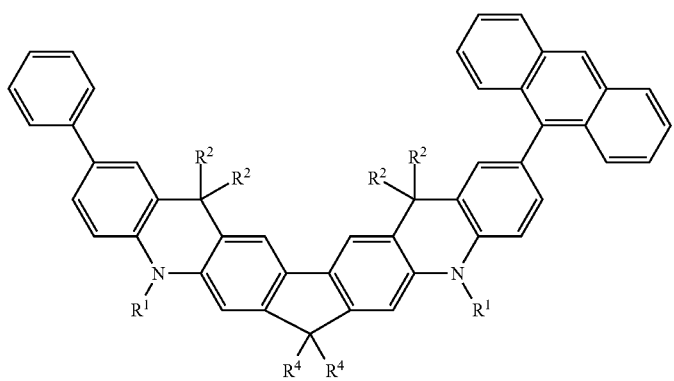

When the compound of the present invention is a polymer compound, examples of such a compound may include compounds listed in the following Table a. Compounds listed in Table b are preferred, and compounds listed in Table c are more preferred. Compounds listed in Table d are particularly preferred.

Each of the compounds listed in Table a is a polymer compound that is composed of the repeating unit represented by formula (2), the repeating unit represented by formula (4), and an additional repeating unit, and comprises the respective repeating units in amounts in percent by mole shown in the table (the total amount of all the repeating units is 100 percent by mole). The "additional repeating unit" means one atomic group that links a plurality of repeating units represented by formulae (2) and/or (4). However, the terminal groups of the polymer compound are not included in the repeating units. One type of repeating unit represented by formula (2) or a combination of two or more types may be used. One type of repeating unit represented by formula (4) or a combination of two or more types may be used.

When the polymer compound is used for a hole injection layer or a hole transport layer, EP1 is preferred, and EP2 is more preferred.

When the polymer compound is used for a light-emitting layer, EP2 is preferred, EP3 is more preferred, and EP4 is particularly preferred.

TABLE a

| Compound | formula (2) | formula (4) | additional |
|---|---|---|---|
| EP1 | 0.1-100 | 0-99.9 | 0-50 |
| EP2 | 0.1-50 | 50-99.9 | 0-49.9 |
| EP3 | 0.5-30 | 50-99.5 | 0-49.5 |
| EP4 | 0.5-30 | 70-99.5 | 0 |

Each of the compounds listed in Table b is a polymer compound that is composed of the repeating unit represented by formula (3), the repeating unit represented by formula (4), and an additional repeating unit, and comprises the respective repeating units in amounts in percent by mole shown in the table (the total amount of all the repeating units is 100 percent by mole). The "additional repeating unit" means one atomic group that links a plurality of repeating units represented by formulae (3) and/or (4). However, the terminal groups of the polymer compound are not included in the repeating units. One type of repeating unit represented by formula (3) or a combination of two or more types may be used. One type of repeating unit represented by formula (4) or a combination of two or more types may be used.

TABLE b

| Compound | formula (3) | formula (4) | additional |
|---|---|---|---|
| EP5 | 0.1-100 | 0-99.9 | 0-50 |
| EP6 | 0.1-50 | 50-99.9 | 0-49.9 |
| EP7 | 0.5-30 | 50-99.5 | 0-49.5 |
| EP8 | 0.5-30 | 70-99.5 | 0 |

Each of the compounds listed in Table c is a polymer compound that is composed of the repeating unit represented by formula (3), the repeating unit represented by formula (5), and an additional repeating unit, and comprises the respective repeating units in amounts in percent by mole shown in the table (the total amount of all the repeating units is 100 percent by mole). The "additional repeating unit" means one atomic group that links a plurality of repeating units represented by formulae (3) and/or (5). However, the terminal groups of the polymer compound are not included in the repeating units. One type of repeating unit represented by formula (3) or a combination of two or more types may be used. One type of repeating unit represented by formula (5) or a combination of two or more types may be used.

TABLE c

| Compound | formula (3) | formula (5) | additional |
|---|---|---|---|
| EP9 | 0.1-100 | 0-99.9 | 0-50 |
| EP10 | 0.1-50 | 50-99.9 | 0-49.9 |
| EP11 | 0.5-30 | 50-99.5 | 0-49.5 |
| EP12 | 0.5-30 | 70-99.5 | 0 |

Each of the compounds listed in Table d is a polymer compound that is composed of the repeating unit represented by formula (3), the repeating unit represented by formula (6), and an additional repeating unit, and comprises the respective repeating units in amounts in percent by mole shown in the table (the total amount of all the repeating units is 100 percent by mole). The "additional repeating unit" means one atomic group that links a plurality of repeating units represented by formulae (3) and/or (6). However, the terminal groups of the polymer compound are not included in the repeating units. One type of repeating unit represented by formula (3) or a combination of two or more types may be used. One type of repeating unit represented by formula (6) or a combination of two or more types may be used.

TABLE d

| Compound | formula (3) | formula (6) | additional |
|---|---|---|---|
| EP13 | 0.1-100 | 0-99.9 | 0-50 |
| EP14 | 0.1-50 | 50-99.9 | 0-49.9 |
| EP15 | 0.5-30 | 50-99.5 | 0-49.5 |
| EP16 | 0.5-30 | 70-99.5 | 0 |

Preferred examples of the polymer compounds EP13, EP14, EP15, and EP16 in Table d are shown below. The number shown on the right side of each structural formula represents the ratio (molar ratio) of the repeating unit.

[Chemical formula 65]

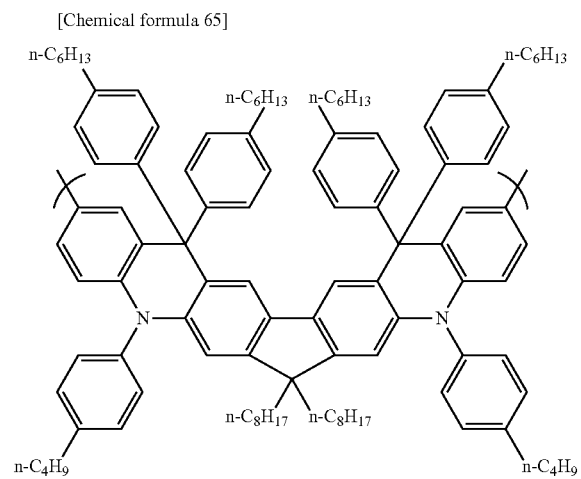

= 100 percent by mol

-continued
[Chemical formula 66]
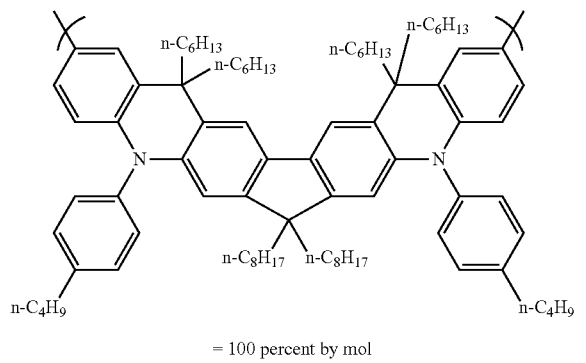
= 100 percent by mol
[Chemical formula 67]
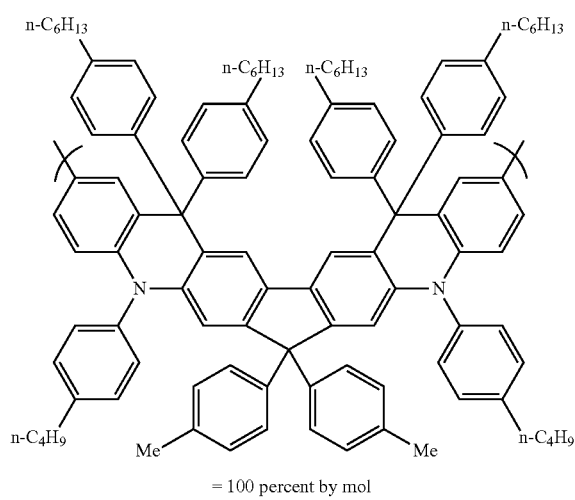
= 100 percent by mol
[Chemical formula 68]
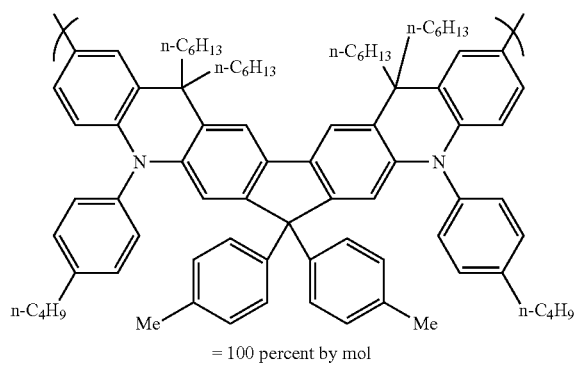
= 100 percent by mol
-continued
[Chemical formula 69]
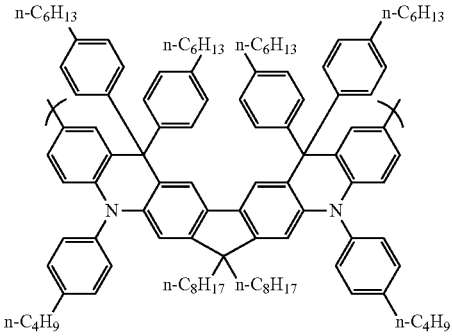 
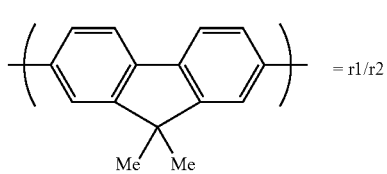 = r1/r2
(wherein r1 is 0.1 to 100 percent by mole, r2 is 0 to 99.9 percent by mole, and r1+r2=100 percent by mole.)
[Chemical formula 70]
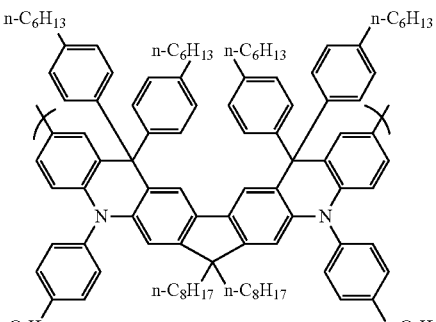 
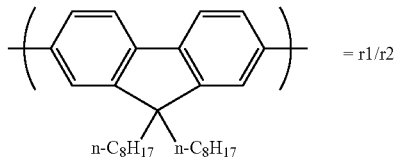 = r1/r2
(wherein r1 is 0.1 to 100 percent by mole, r2 is 0 to 99.9 percent by mole, and r1+r2=100 percent by mole.)

[Chemical formula 71]
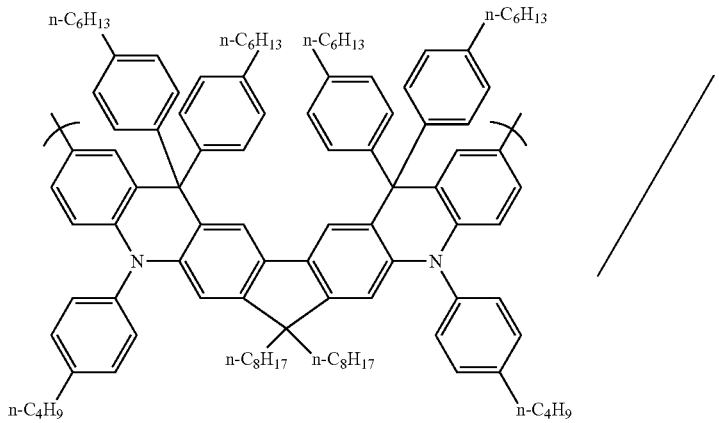
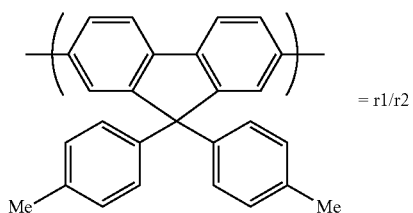
= r1/r2
(wherein r1 is 0.1 to 100 percent by mole, r2 is 0 to 99.9 percent by mole, and r1+r2=100 percent by mole.)
[Chemical formula 72]
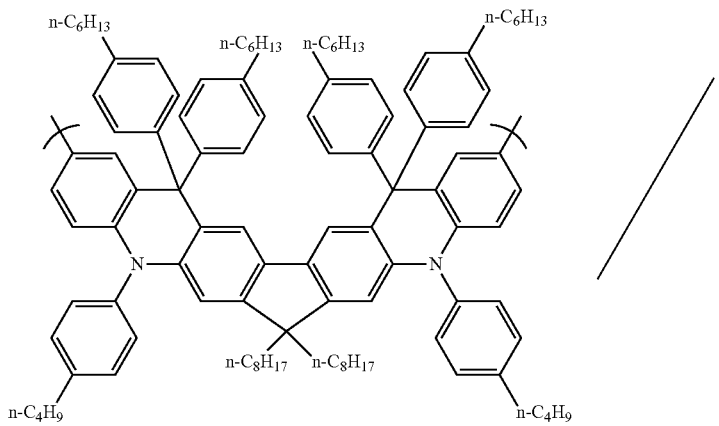
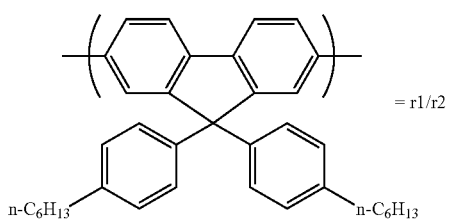
= r1/r2
(wherein r1 is 0.1 to 100 percent by mole, r2 is 0 to 99.9 percent by mole, and r1+r2=100 percent by mole.)

[Chemical formula 73]
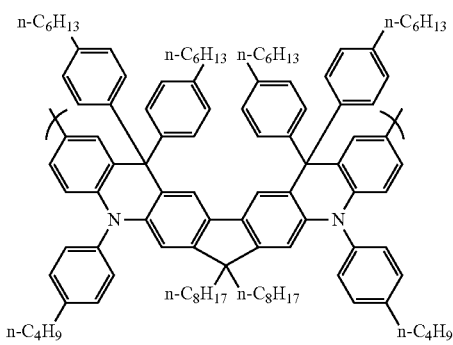
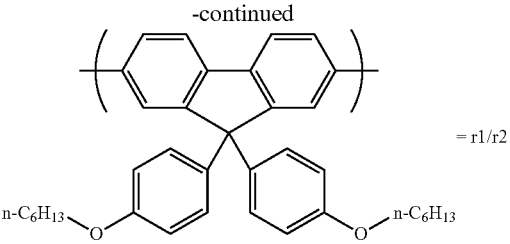
= r1/r2
(wherein r1 is 0.1 to 100 percent by mole, r2 is 0 to 99.9 percent by mole, and r1+r2=100 percent by mole.)
[Chemical formula 74]
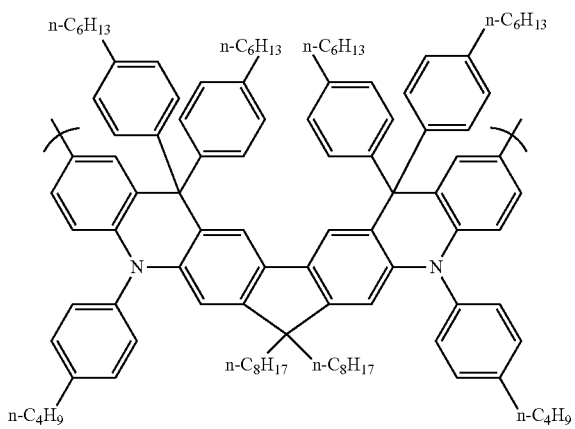
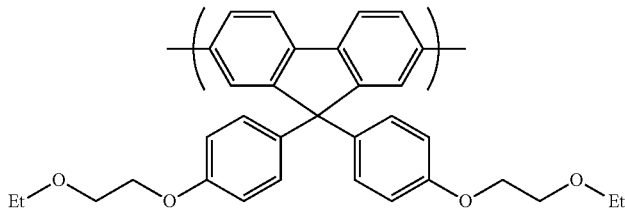
= r1/r2
(wherein r1 is 0.1 to 100 percent by mole, r2 is 0 to 99.9 percent by mole, and r1+r2=100 percent by mole.)
[Chemical formula 75]
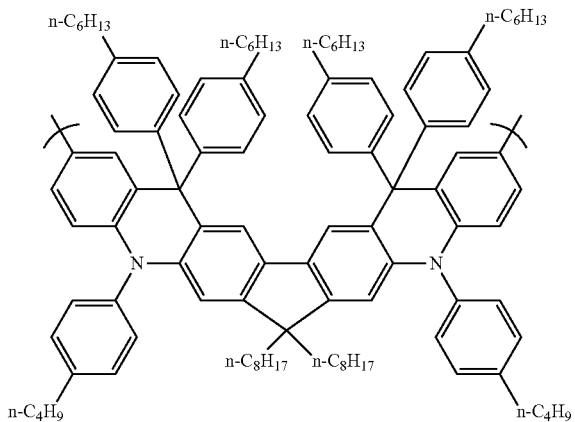

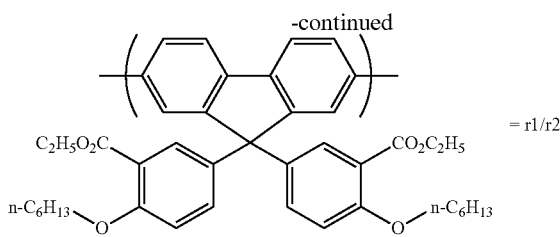
= r1/r2
(wherein r1 is 0.1 to 100 percent by mole, r2 is 0 to 99.9 percent by mole, and r1+r2=100 percent by mole.)
[Chemical formula 76]
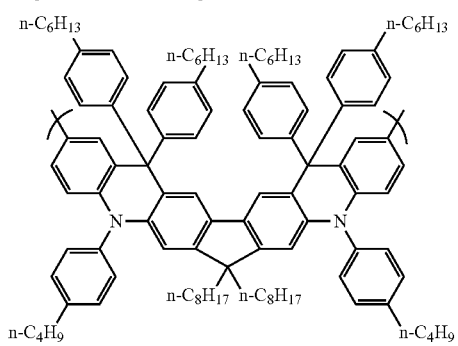
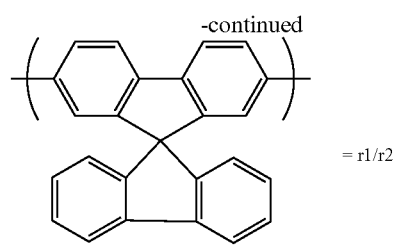
= r1/r2
(wherein r1 is 0.1 to 100 percent by mole, r2 is 0 to 99.9 percent by mole, and r1+r2=100 percent by mole.)
[Chemical formula 77]
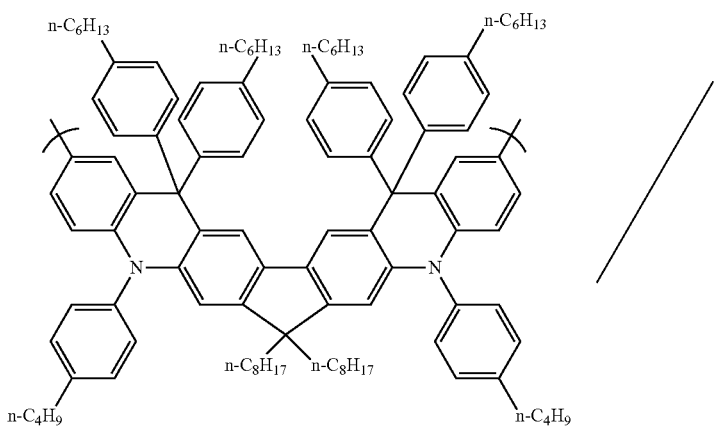
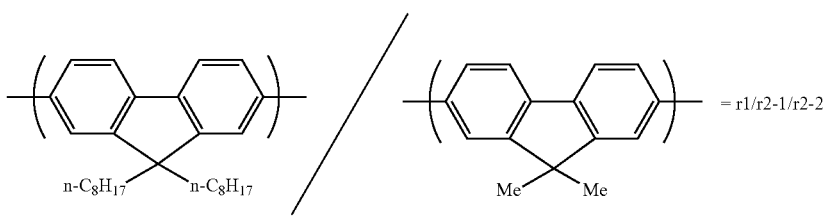
= r1/r2-1/r2-2
(wherein r1 is 0.1 to 100 percent by mole, r2-1 and r2-2 are each independently 0 to 99.9 percent by mole, and r1+(r2-1)+(r2-2)=100 percent by mole.)

[Chemical formula 78]
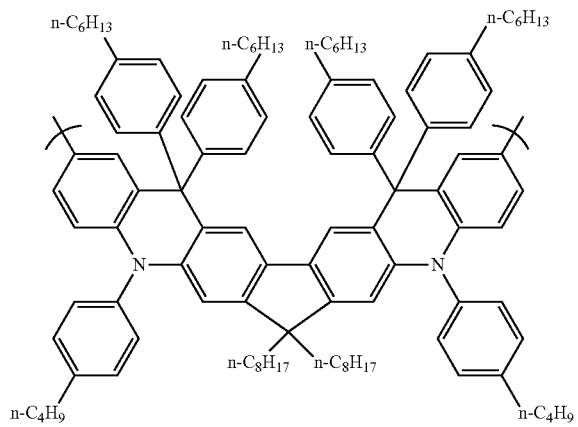
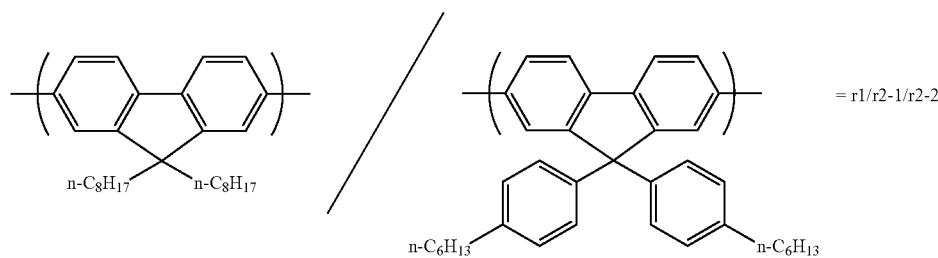
= r1/r2-1/r2-2
(wherein r1 is 0.1 to 100 percent by mole, r2-1 and r2-2 are each independently 0 to 99.9 percent by mole, and r1+(r2-1)+(r2-2)=100 percent by mole.)
[Chemical formula 79]
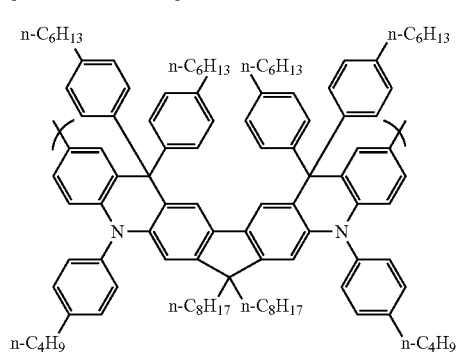
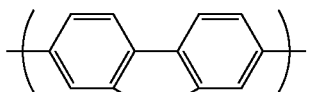
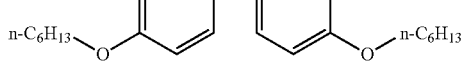
= r1/r2-1/r2-2
-continued
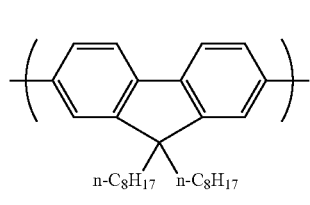
(wherein r1 is 0.1 to 100 percent by mole, r2-1 and r2-2 are each independently 0 to 99.9 percent by mole, and r1+(r2-1)+(r2-2)=100 percent by mole.)

[Chemical formula 80]
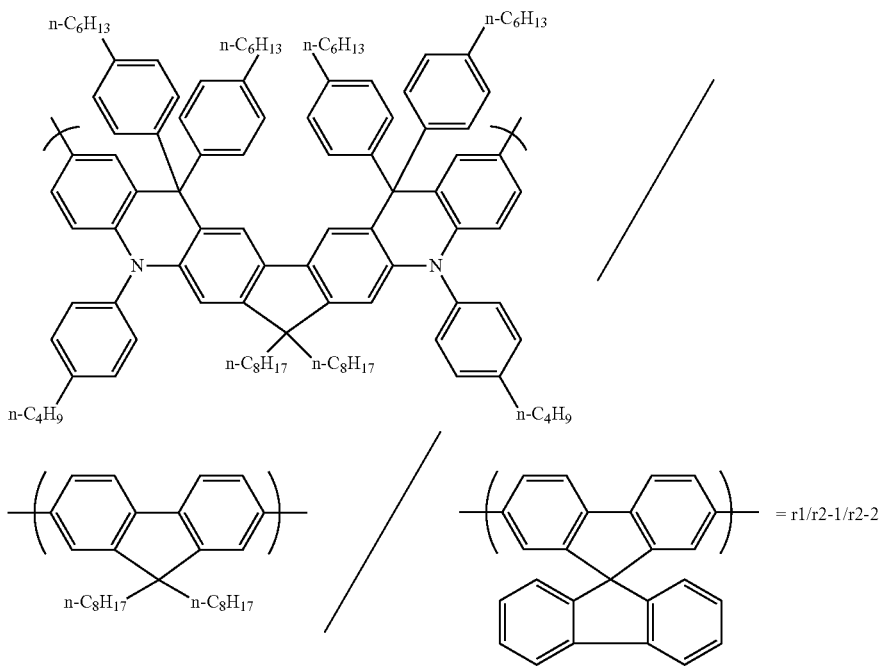
(wherein r1 is 0.1 to 100 percent by mole, r2-1 and r2-2 are each independently 0 to 99.9 percent by mole, and r1+(r2-1)+(r2-2)=100 percent by mole.)
[Chemical formula 81]
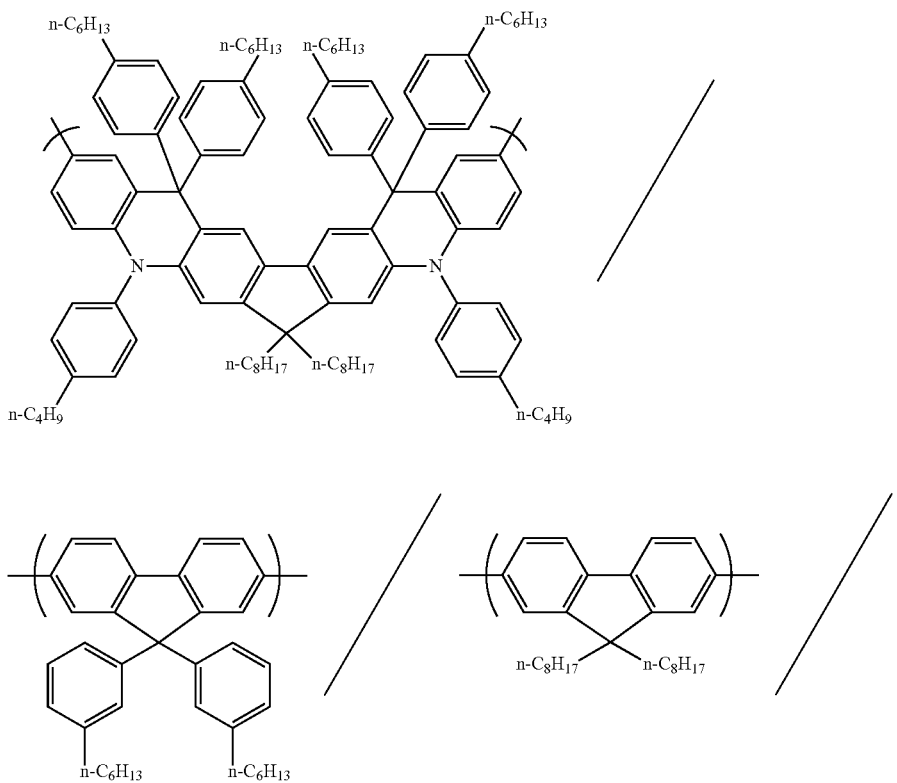

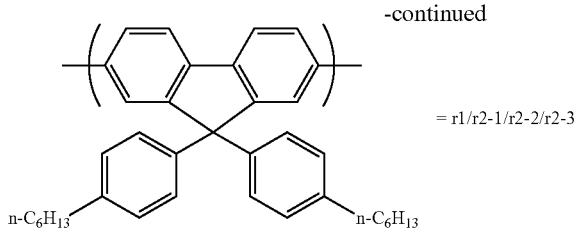
= r1/r2-1/r2-2/r2-3
(wherein r1 is 0.1 to 100 percent by mole, r2-1, r2-2, and r2-3 are each independently 0 to 99.9 percent by mole, and r1+(r2-1)+(r2-2)+(r2-3)=100 percent by mole.)
[Chemical formula 82]
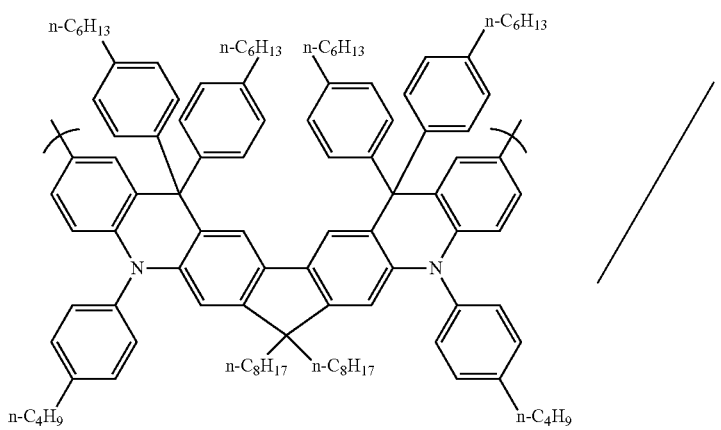
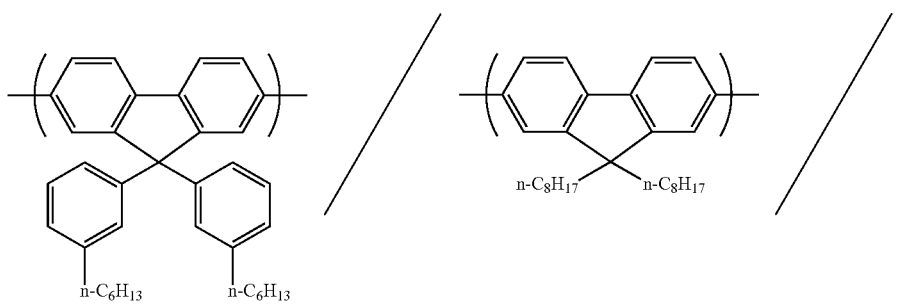
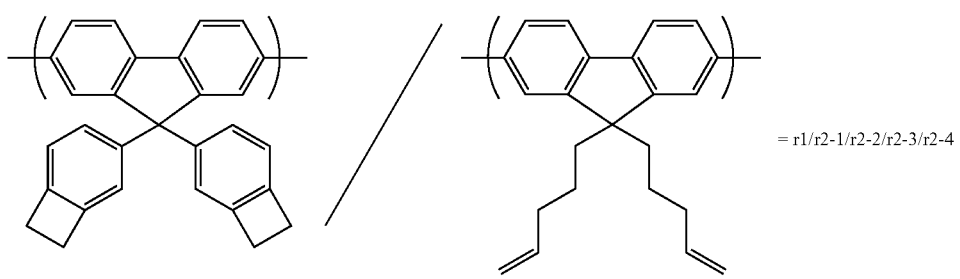
= r1/r2-1/r2-2/r2-3/r2-4
(wherein r1 is 0.1 to 100 percent by mole, r2-1, r2-2, r2-3, and r2-4 are each independently 0 to 99.9 percent by mole, and r1+(r2-1)+(r2-2)+(r2-3)+(r2-4)=100 percent by mole.)

[Chemical formula 83]
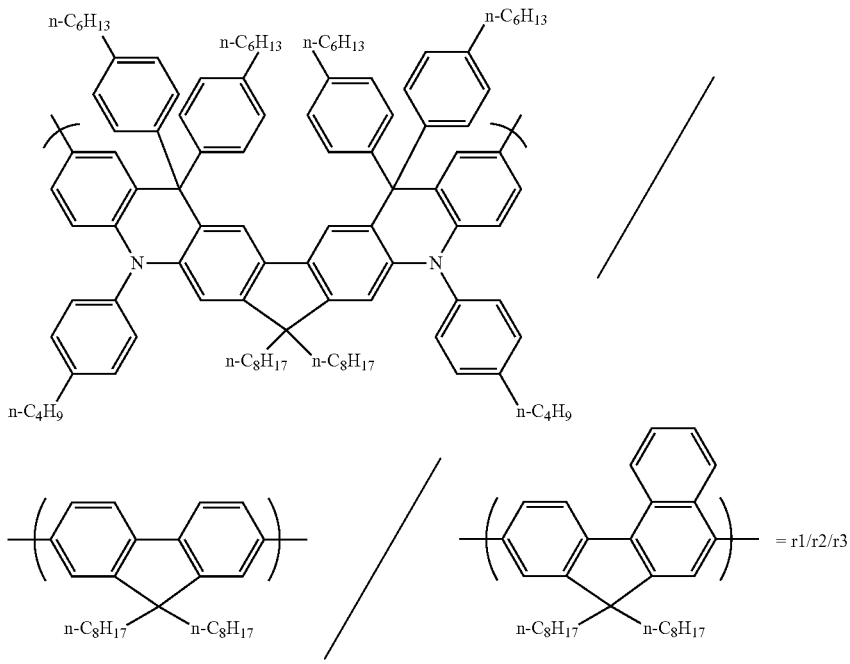
= r1/r2/r3
(wherein r1 is 0.1 to 100 percent by mole, r2 is 0 to 99.9 percent by mole, r3 is 0 to 50 percent by mole, and r1+r2+r3=100 percent by mole.)
[Chemical formula 84]
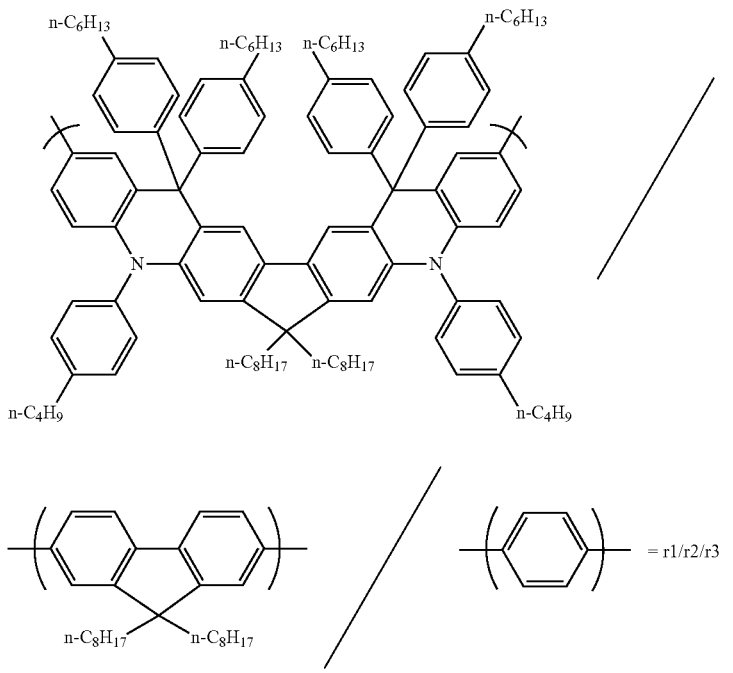
= r1/r2/r3
(wherein r1 is 0.1 to 100 percent by mole, r2 is 0 to 99.9 percent by mole, r3 is 0 to 50 percent by mole, and r1+r2+r3=100 percent by mole.)

[Chemical formula 85]
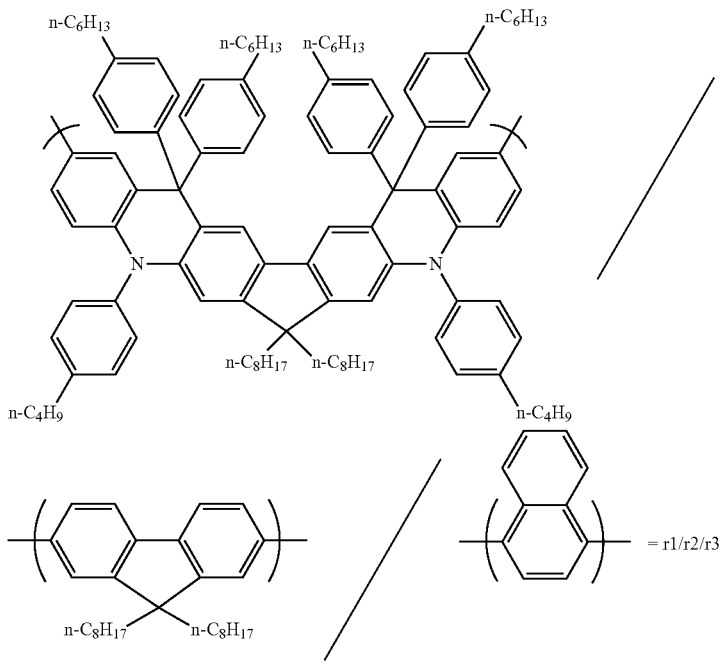
(wherein r1 is 0.1 to 100 percent by mole, r2 is 0 to 99.9 percent by mole, r3 is 0 to 50 percent by mole, and r1+r2+r3=100 percent by mole.)
[Chemical formula 86]
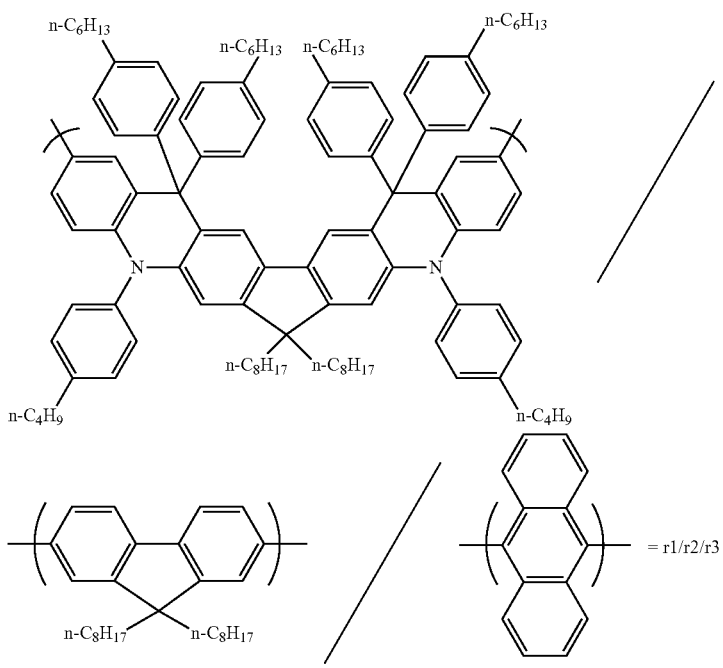
(wherein r1 is 0.1 to 100 percent by mole, r2 is 0 to 99.9 percent by mole, r3 is 0 to 50 percent by mole, and r1+r2+r3=100 percent by mole.)

[Chemical formula 87]

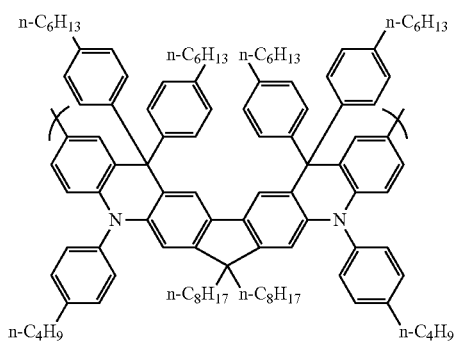
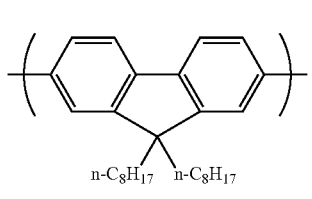

= r1/r2/r3

(wherein r1 is 0.1 to 100 percent by mole, r2 is 0 to 99.9 percent by mole, r3 is 0 to 50 percent by mole, and r1+r2+r3=100 percent by mole.)

[Chemical formula 88]

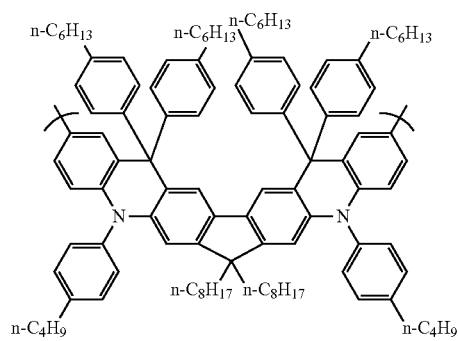
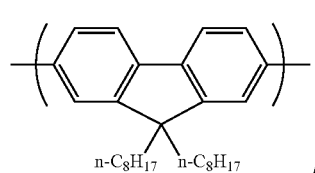

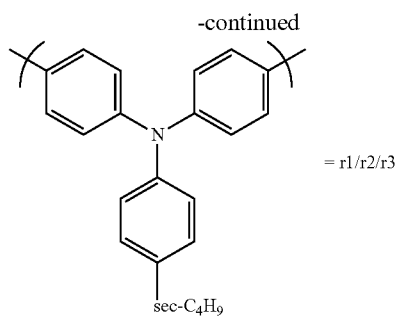

= r1/r2/r3

(wherein r1 is 0.1 to 100 percent by mole, r2 is 0 to 99.9 percent by mole, r3 is 0 to 50 percent by mole, and r1+r2+r3=100 percent by mole.)

[Chemical formula 89]

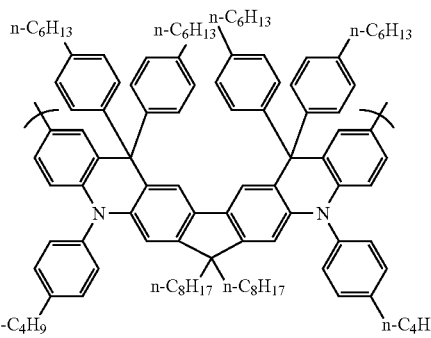
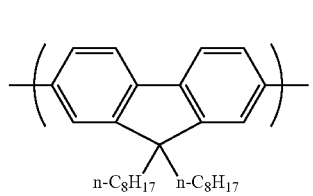
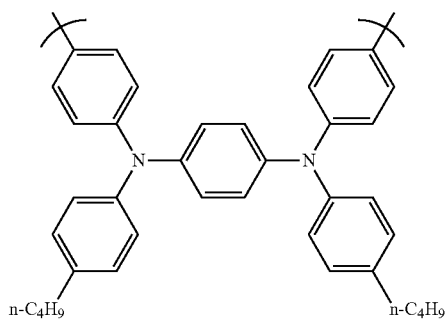

= r1/r2/r3

(wherein r1 is 0.1 to 100 percent by mole, r2 is 0 to 99.9 percent by mole, r3 is 0 to 50 percent by mole, and r1+r2+r3=100 percent by mole.)

[Chemical formula 90]

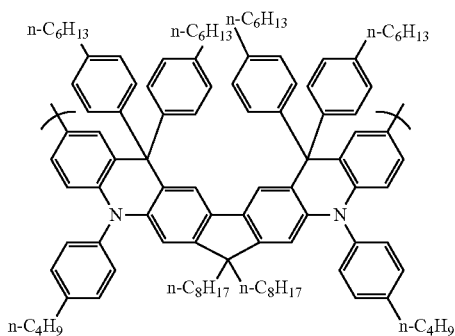

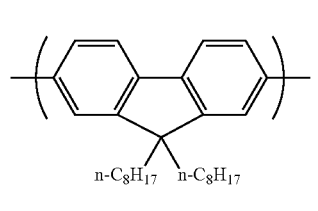

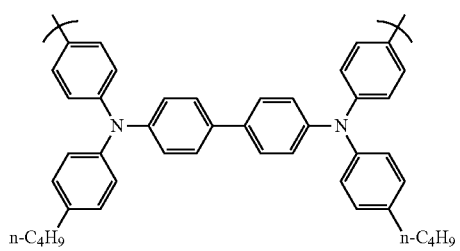

= r1/r2/r3

(wherein r1 is 0.1 to 100 percent by mole, r2 is 0 to 99.9 percent by mole, r3 is 0 to 50 percent by mole, and r1+r2+r3=100 percent by mole.)

[Chemical formula 91]

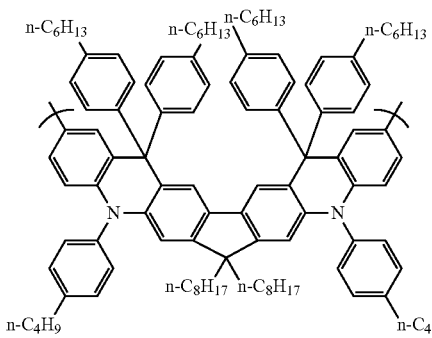

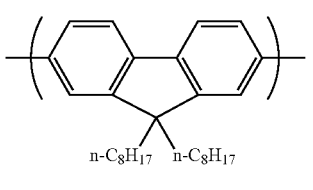

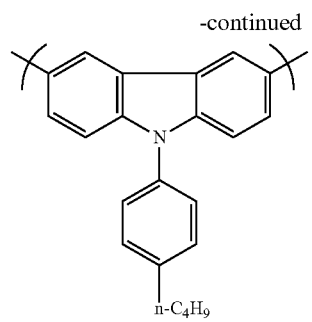

= r1/r2/r3

(wherein r1 is 0.1 to 100 percent by mole, r2 is 0 to 99.9 percent by mole, r3 is 0 to 50 percent by mole, and r1+r2+r3=100 percent by mole.)

[Chemical formula 92]

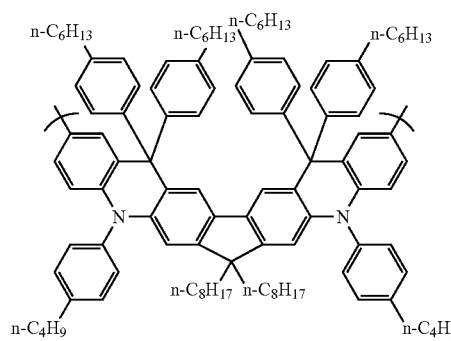

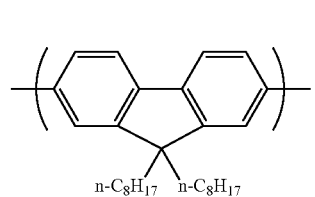

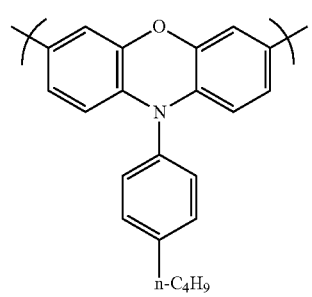

= r1/r2/r3

(wherein r1 is 0.1 to 100 percent by mole, r2 is 0 to 99.9 percent by mole, r3 is 0 to 50 percent by mole, and r1+r2+r3=100 percent by mole.)

[Chemical formula 93]

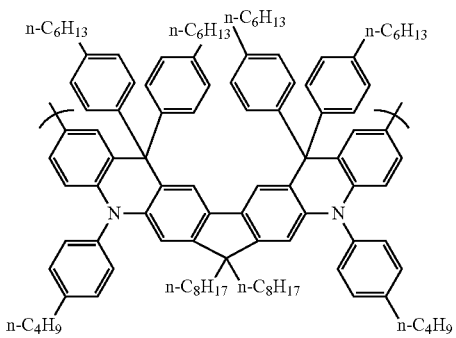

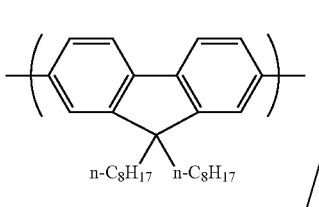

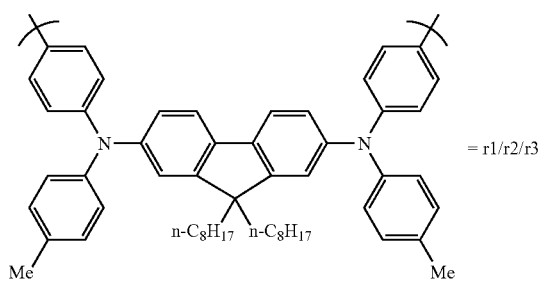

= r1/r2/r3

(wherein r1 is 0.1 to 100 percent by mole, r2 is 0 to 99.9 percent by mole, r3 is 0 to 50 percent by mole, and r1+r2+r3=100 percent by mole.)

<Method of Producing Polymer Compound>

The polymer compound of the present invention may be produced by any method. Examples of the method of producing the polymer compound of the present invention may include a method of producing a polymer compound comprising the above-described repeating unit represented by formula (3), the method including polymerizing a compound represented by the following formula (7) to obtain the polymer compound comprising the repeating unit represented by formula (3). When polymerization is used for the production of the polymer compound of the present invention, the polymerization may be performed in the presence of a transition metal catalyst.

To eliminate the influence of polymerizable functional groups, treatment with a terminal treating agent may be performed.

[Chemical formula 94]

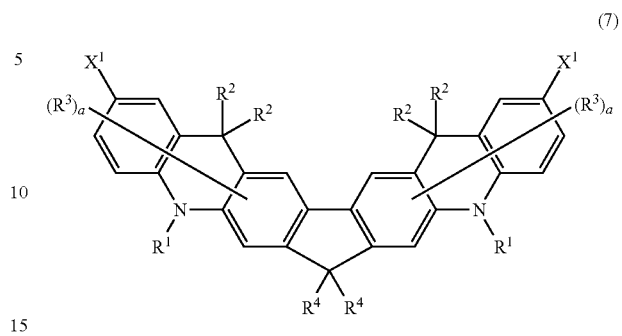

(7)

wherein
each $R^1$ represents a hydrogen atom, an alkyl group, an aryl group, an arylalkyl group, an acyl group, or a monovalent heterocyclic group, each of these groups optionally having a substituent;
the $R^1$s may be the same or different;
each $R^2$ represents a hydrogen atom, an alkyl group, an alkoxy group, an aryl group, an aryloxy group, an arylalkyl group, an arylalkoxy group, an alkenyl group, an arylalkenyl group, an acyl group, an acyloxy group, a monovalent heterocyclic group, or a heterocyclyloxy group, each of these groups optionally having a substituent;
the $R^2$s may be the same or different;
two $R^2$ bonded to the same carbon atom may be connected to form a ring;
each $R^3$ represents an alkyl group, an alkoxy group, an aryl group, an aryloxy group, an arylalkyl group, an arylalkoxy group, an alkenyl group, an arylalkenyl group, an alkynyl group, an arylalkynyl group, an amino group, a silyl group, a halogen atom, an acyl group, an acyloxy group, a carbamoyl group, a monovalent heterocyclic group, a heterocyclyloxy group, a carboxyl group, a nitro group, or a cyano group, each of these groups optionally having a substituent;
where there are a plurality of $R^3$, they may be the same or different;
each $R^4$ represents a hydrogen atom, an alkyl group, an aryl group, an arylalkyl group, or a monovalent heterocyclic group, each of these groups optionally having a substituent;
the $R^4$s may be the same or different;
the two $R^4$s may be connected to form a ring;
each $X^1$ represents a group capable of participating in polymerization;
the $X^1$s may be the same or different;
each a represents an integer of from 0 to 5; and
the a's may be the same or different.

The groups represented by $R^1$, $R^2$, $R^3$, and $R^4$ are the same as those described and exemplified for $R^1$, $R^2$, $R^3$, and $R^4$ in the above-described formulae (1) and (2).

The group capable of participating in polymerization which is represented by $X^1$ is a group that a part of or all of the group leaves during a condensation reaction. Examples of such a group may include a formyl group, a halogen atom, —B(OH)$_2$, a borate ester residue, a monohalogenated magnesium, a stannyl group, an alkylsulfonyloxy group, an arylsulfonyloxy group, an arylalkylsulfonyloxy group, a sulfonium methyl group, a phosphonium methyl group, a phosphonate methyl group, and a monohalogenated methyl group.

Examples of the halogen atom serving as the group capable of participating in polymerization may include a fluorine atom, a chlorine atom, a bromine atom, and an iodine atom.

From the viewpoint of ease of controlling the reaction, a chlorine atom, a bromine atom, and an iodine atom are preferred, and a bromine atom is more preferred.

Examples of the borate ester residue serving as the group capable of participating in polymerization may include a dialkyl ester residue, a diaryl ester residue, a diarylalkyl ester residue, and groups represented by the following formulae.

[Chemical formula 95]

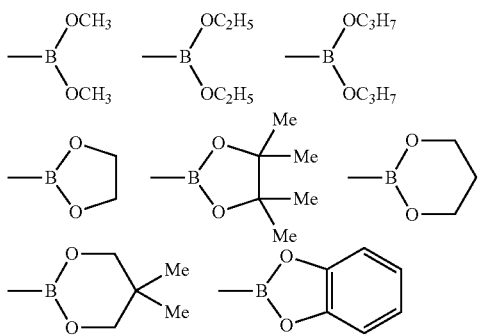

Examples of the monohalogenated magnesium serving as the group capable of participating in polymerization may include monochloro magnesium, monobromo magnesium, and monoiode magnesium.

Examples of the stannyl group serving as the group capable of participating in polymerization may include a stannyl group, a trichlorostannyl group, a trimethylstannyl group, a triethylstannyl group, and a tri-n-butylstannyl group.

Examples of the alkylsulfonyloxy group serving as the group capable of participating in polymerization may include a methanesulfonyloxy group, an ethanesulfonyloxy group, and a trifluoromethanesulfonyloxy group.

Examples of the arylsulfonyloxy group serving as the group capable of participating in polymerization may include a benzenesulfonyloxy group and a p-toluenesulfonyloxy group.

Examples of the arylalkylsulfonyloxy group serving as the group capable of participating in polymerization may include a benzylsulfonyloxy group.

Examples of the sulfonium methyl group may include groups represented by the following formulae.

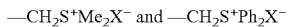

wherein each X represents a halogen atom, and the same applies hereinafter.

Examples of the phosphonium methyl group may include a group represented by the following formula.

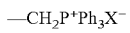

Examples of the phosphonate methyl group may include a group represented by the following formula.

wherein R" represents an alkyl group, an aryl group, or an arylalkyl group.

Examples of the monohalogenated methyl group may include a monofluorinated methyl group, a monochloromethyl group, a monobrominated methyl group, and a monoiodinated methyl group.

Next, a method of producing a polymer compound comprising the repeating unit represented by formula (3) will be described as a representative example. When the polymer compound of the present invention comprises a repeating unit other than the above-described repeating unit represented by formula (2) or (3), a monomer corresponding to the repeating unit other than the repeating unit represented by formula (2) or (3) is added to the reaction system such that the monomer is allowed to coexist therein.

Examples of the polymerization method used for polymerization in the presence of a transition metal may include [3], [4], [11], [12], [13], [14], and [15] described later.

The amount used of the transition metal catalyst depends on the polymerization method used but is generally in the range of 0.0001 moles to 10 moles based on 1 mole of the total amount of monomers used for the polymerization.

Examples of the transition metal catalyst may include nickel catalysts and palladium catalysts.

Examples of the nickel catalysts may include tetrakis(triphenylphosphine)nickel(0), bis(cyclooctadienyl)nickel(0), dichloro bis(triphenylphosphine)nickel(II), [1,3-bis(diphenylphosphine)propane]dichloro nickel(II), and [1,1'-bis(diphenylphosphino)ferrocene]dichloro nickel(II).

Examples of the palladium catalysts may include palladium acetate, palladium[tetrakis(triphenylphosphine)], bis(tricyclohexylphosphine)palladium, dichloro bis(triphenylphosphine)palladium, and [1,1'-bis(diphenylphosphino)ferrocene]dichloro palladium(II).

When the polymer compound of the present invention has a vinylene group on its main chain, any of the following reactions [1] to [11] can be used to produce the polymer compound.

[1] Polymerization of a compound having a formyl group and a compound having a phosphonium methyl group by the Wittig reaction

[2] Polymerization of a compound having a formyl group and a phosphonium methyl group by the Wittig reaction

[3] Polymerization of a compound having a vinyl group and a compound having a halogen atom by the Heck reaction

[4] Polymerization of a compound having a vinyl group and a halogen atom by the Heck reaction

[5] Polymerization of a compound having a formyl group and a compound having a phosphonate methyl group by the Horner-Wadsworth-Emmons method

[6] Polymerization of a compound having a formyl group and a phosphonate methyl group by the Horner-Wadsworth-Emmons method

[7] Polycondensation of a compound having at least two monohalogenated methyl groups by the dehydrohalogenation method

[8] Polycondensation of a compound having at least two sulfonium salt groups by the sulfonium salt decomposition method

[9] Polymerization of a compound having a formyl group and a compound having a cyanomethyl group by the Knoevenagel reaction

[10] Polymerization of a compound having a formyl group and a cyanomethyl group by the Knoevenagel reaction

[11] Polymerization of a compound having at least two formyl groups by the McMurry reaction These [1] to [11] are represented by the following formulae.

[Chemical formula 96]

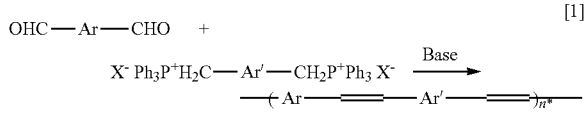

-continued

[Chemical formula 97]

$$\text{OHC}—\text{Ar}—\text{CH}_2\text{P}^+\text{Ph}_3\ \text{X}^- \xrightarrow{\text{Base}} \text{—(Ar}\mathrm{=\!=\!=}\text{)}_{n^*}\text{—} \quad [2]$$

[Chemical formula 98]

$$\mathrm{=\!=\!=}\text{—Ar—}\mathrm{=\!=\!=}\ +\ \text{Br—Ar}'\text{—Br} \xrightarrow[\text{Pd Cat.}]{\text{Base}} \text{—(Ar}\mathrm{=\!=\!=}\text{Ar}'\mathrm{=\!=\!=}\text{)}_{n^*}\text{—} \quad [3]$$

[Chemical formula 99]

$$\text{Br—Ar—}\mathrm{=\!=\!=} \xrightarrow[\text{Pd Cat.}]{\text{Base}} \text{—(Ar}\mathrm{=\!=\!=}\text{)}_{n^*}\text{—} \quad [4]$$

[Chemical formula 100]

$$\text{OHC—Ar—CHO}\ +\ (\text{RO})_2(\text{O})\text{PH}_2\text{C—Ar}'\text{—CH}_2\text{P(O)(OR)}_2 \xrightarrow{\text{Base}} \text{—(Ar}\mathrm{=\!=\!=}\text{Ar}'\mathrm{=\!=\!=}\text{)}_{n^*}\text{—} \quad [5]$$

[Chemical formula 101]

$$\text{OHC—Ar—CH}_2\text{P(O)(OR)}_2 \xrightarrow{\text{Base}} \text{—(Ar}\mathrm{=\!=\!=}\text{)}_{n^*}\text{—} \quad [6]$$

[Chemical formula 102]

$$\text{XH}_2\text{C—Ar—CH}_2\text{X} \xrightarrow{\text{Base}} \text{—(Ar}\mathrm{=\!=\!=}\text{)}_{n^*}\text{—} \quad [7]$$

[Chemical formula 103]

$$\text{—(Ar}\overset{+\text{S}\,(\text{tetrahydrothiophenium})}{\underset{\text{X}^-}{\big|}}\text{)}_n\text{—} \xrightarrow{\text{pyrolysis}} \text{—(Ar}\mathrm{=\!=\!=}\text{)}_{n^*}\text{—} \quad [8]$$

[Chemical formula 104]

$$\text{OHC—Ar—CHO}\ +\ \text{NCCH}_2\text{—Ar}'\text{—CH}_2\text{CN} \xrightarrow{\text{Base}} \text{—(Ar}\mathrm{=\!=\!\overset{\text{CN}}{\underset{}{}}\!=}\text{Ar}'\mathrm{=\!\overset{}{\underset{\text{CN}}{}}\!=}\text{)}_{n^*}\text{—} \quad [9]$$

[Chemical formula 105]

$$\text{OHC—Ar—CH}_2\text{CN} \xrightarrow{\text{Base}} \text{—(Ar}\mathrm{=\!\!\underset{\text{CN}}{=}\!\!}\text{)}_{n^*}\text{—} \quad [10]$$

[Chemical formula 106]

$$\text{OHC—Ar—CHO} \xrightarrow{\text{TiCl}_3\text{—Zn}} \text{—(Ar}\mathrm{=\!=\!=}\text{)}_{n^*}\text{—} \quad [11]$$

When the polymer compound of the present invention has no vinylene group on its main chain, reactions [12] to [17] below can be used to produce the polymer compound.

[12] Polymerization by the Suzuki coupling reaction
[13] Polymerization by the Grignard reaction
[14] Polymerization by the Stifle coupling reaction
[15] Polymerization using a Ni(0) catalyst
[16] Polymerization using an oxidant such as FeCl$_3$, or electrochemical oxidation polymerization
[17] A method by decomposition of an intermediate macromolecule having a suitable leaving group These [12] to [17] are represented by the following formulae.

[Chemical formula 107]

$$\text{Br—Ar—Br}\ +\ (\text{R}'\text{O})_2\text{B—Ar}'\text{—B(OR}')_2 \xrightarrow[\text{Base}]{\text{Pd Cat.}} \text{—(Ar—Ar}')_{n^*}\text{—} \quad [12]$$

$$\text{Br—Ar—B(OR}')_2 \xrightarrow[\text{Base}]{\text{Pd Cat.}} \text{—(Ar)}_{n^*}\text{—}$$

R' = H, alkyl, aryl

[Chemical formula 108]

$$\text{Br—Ar—Br}\ +\ \text{X}'\text{Mg—Ar}'\text{—MgX}' \xrightarrow{\text{Ni Cat.}} \text{—(Ar—Ar}')_{n^*}\text{—} \quad [13]$$

$$\text{Br—Ar}'\text{—MgX}' \xrightarrow{\text{Ni Cat.}} \text{—(Ar)}_{n^*}\text{—}$$

X' = Cl, Br, I

[Chemical formula 109]

$$\text{Br—Ar—Br}\ +\ \text{R}''_3\text{Sn—Ar}'\text{—SnR}''_3 \xrightarrow{\text{Pd Cat.}} \text{—(Ar—Ar}')_{n^*}\text{—} \quad [14]$$

$$\text{Br—Ar—SnR}''_3 \xrightarrow{\text{Pd Cat.}} \text{—(Ar)}_{n^*}\text{—}$$

R' = Alkyl

[Chemical formula 110]

$$\text{X}'\text{—Ar—X}' \xrightarrow{\text{Ni(O).}} \text{—(Ar)}_{n^*}\text{—} \quad [15]$$

X' = Cl, Br, I

[Chemical formula 111]

$$\text{H—Ar—H} \xrightarrow[\text{FeCl}_3,\ \text{electrochemically}]{\text{Oxidative polymerization}} \text{—(Ar)}_{n^*}\text{—} \quad [16]$$

[Chemical formula 112]

(ROCO, OCOR substituted cyclohexene polymer) $\xrightarrow{\text{pyrolysis}}$ (R-substituted phenylene polymer) [17]

Of these, polymerization by the Wittig reaction, polymerization by the Heck reaction, polymerization by the Horner-Wadsworth-Emmons method, polymerization by the Knoevenagel reaction, polymerization by the Suzuki coupling reaction, the polymerization method by the Grignard reaction, the method using the Stille coupling, and polymerization using a Ni(0) catalyst are preferred from the viewpoint of structure control. Polymerization by the Suzuki coupling reaction, polymerization by the Grignard reaction, and polymerization using a Ni(0) catalyst are preferred from the viewpoints of availability of raw materials and controllability of the polymerization reaction.

If necessary, the monomer is dissolved in an organic solvent. Then a reaction is performed using, for example, an alkali or a suitable catalyst at a temperature equal to or higher than the melting point of the organic solvent and equal to or lower than its boiling point. For more details, see, for example, the description in "Organic Reactions," Vol. 14, pp. 270-490, John Wiley & Sons, Inc., 1965; "Organic Reactions," Vol. 27, pp. 345-390, John Wiley & Sons, Inc., 1982; "Organic Syntheses," Collective Volume VI, pp. 407-411, John Wiley & Sons, Inc., 1988; Chem. Rev., Vol. 95, p. 2457 (1995); J. Organomet. Chem., Vol. 576, p. 147 (1999); J. Prakt. Chem., Vol. 336, p. 247 (1994); and Makromol. Chem., Macromol. Symp., Vol 12, p. 229 (1987).

Preferably, the organic solvent is subjected to sufficient deoxidation and dehydration to suppress a side reaction. Preferably, the reaction system is under an inert atmosphere, but this is not the case for a reaction in a two-phase system including the organic solvent and water, for example, for the Suzuki coupling reaction.

Preferably, the alkali and catalyst described above can sufficiently dissolve in the solvent used for the reaction. Examples of the method of adding the alkali and/or catalyst may include a method in which a solution of the alkali and/or catalyst is slowly added to the reaction solution while it is stirred under an inert atmosphere such as an argon or nitrogen atmosphere; and a method in which the reaction solution is slowly added to the solution of the alkali and/or catalyst.

The purity of the polymer compound of the present invention has an influence on light-emitting characteristics. Therefore, it is preferred that the monomer before polymerization is purified by a method such as distillation, sublimation purification, or recrystallization and then the purified monomer is polymerized. After synthesis, purification treatment such as purification by reprecipitation or fractionation by chromatography is preferably performed.

In the production of the polymer compound of the present invention, when a plurality of monomers are used as raw materials, these may be mixed and reacted at once or may be mixed and reacted separately.

The reaction conditions will be descried in more detail. When the Wittig reaction, Horner reaction, or Knoevenagel reaction is used, the reaction is performed using an alkali in an amount of one equivalent or more with respect to the functional groups of the monomer and preferably 1 to 3 equivalents.

Examples of the alkali may include metal alcoholates such as potassium tert-butoxide, sodium tert-butoxide, sodium ethylate, and lithium methylate; hydride reagents such as sodium hydride; and amides such as sodium amide.

Examples of the solvent may include N,N-dimethylformamide, tetrahydrofuran, dioxane, and toluene.

The temperature of the reaction is generally room temperature to 150° C.

The reaction time is set so that reaction proceeds sufficiently and is generally 5 minutes to 40 hours.

The concentration in the reaction is generally 0.1 to 20 percent by weight.

When the Heck reaction is used, the monomer is allowed to react using a palladium catalyst in the presence of a base such as triethylamine. For example, a solvent having a relatively high boiling point, such as N,N-dimethylformamide or N-methylpyrrolidone is used. The reaction temperature is 80 to 160° C., and the reaction time is 1 to 100 hours.

When the Suzuki coupling reaction is used, a palladium catalyst such as palladium[tetrakis(triphenylphosphine)] or palladium acetate is used as a catalyst, and an inorganic base such as potassium carbonate, sodium carbonate, or barium hydroxide, an organic base such as triethylamine or tetraethylammonium hydroxide, or an inorganic salt such as cesium fluoride is added in an amount of one equivalent or more with respect to the monomer and preferably 1 to 10 equivalents, and the mixture is allowed to react. An aqueous solution of the inorganic salt may be used, and the reaction may be performed in a two-phase system.

Examples of the solvent may include N,N-dimethylformamide, toluene, dimethoxyethane, and tetrahydrofuran.

The reaction temperature is preferably 50 to 160° C. The temperature may be increased to the vicinity of the boiling point of the solvent to reflux the solvent.

The reaction time is 1 to 200 hours.

When the Grignard reaction is used, the following method may be used. A halide and metal magnesium are reacted in an ether-based solvent such as tetrahydrofuran, diethyl ether, or dimethoxyethane to obtain a Grignard reagent solution. The Grignard reagent solution is mixed with a monomer solution prepared separately, and a nickel catalyst or a palladium catalyst is added to the mixture while care is taken to prevent the reaction from proceeding excessively. Then temperature is increased, and the reaction is allowed to proceed under reflux. The Grignard reagent is used in an amount of one equivalent or more with respect to the monomer and preferably 1 to 1.5 equivalents.

When the reaction is performed in the presence of a nickel catalyst, the above-described method in which polymerization is performed using Ni(0) catalyst may be used.

<Method of Producing Monomer>

A compound that can be used as the raw material of the polymer compound of the present invention may be produced by any method. For example, a compound represented by the following formula (7-1) is used. A low molecular compound having the above-described structure represented by formula (1) can be synthesized by, for example, any of various coupling reactions such as Suzuki coupling of the compound represented by formula (7-1) with boric acid or a borate ester compound, Kumada coupling with a Grignard reagent, and Negishi coupling with a zinc reagent.

Next, a method of producing the compound represented by the following formula (7-1) will be described as a representative example.

[Chemical formula 113]

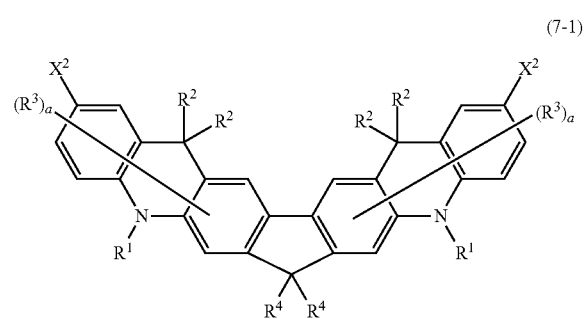

(7-1)

wherein $R^1$, $R^2$, $R^3$, $R^4$ and a are the same as in the above-described formula (8);

each $X^2$ represents a halogen atom; and the $X^2$s may be the same or different.

In the above-described formula (7-1), the halogen atoms represented by $X^2$ are the same as those described and exemplified for the above-described $X^1$. Preferably, from the viewpoint of ease of synthesis, the two $X^2$ are the same.

The compound represented by formula (7-1) can be produced by, for example, the following reactions (1) to (4).

Reaction (1): Synthesis of a compound represented by formula (10) using a compound represented by formula (12) and a compound represented by formula (13)

Reaction (2): Synthesis of a compound represented by formula (9) using the compound represented by formula (10)

Reaction (3): Synthesis of a compound represented by formula (8) using the compound represented by formula (9)

Reaction (4): Synthesis of the compound represented by formula (7-1) using the compound represented by formula (8)

More specifically, the reaction (1) is the reaction of the compound represented by the following formula (12) with the compound represented by the following formula (13) in the presence of a transition metal catalyst and a base to synthesize the compound represented by the following formula (10).

[Chemical formula 114]

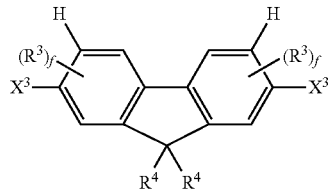

(12)

wherein each $R^3$ represents an alkyl group, an alkoxy group, an aryl group, an aryloxy group, an arylalkyl group, an arylalkoxy group, an alkenyl group, an arylalkenyl group, an alkynyl group, an arylalkynyl group, an amino group, a silyl group, a halogen atom, an acyl group, an acyloxy group, a carbamoyl group, a monovalent heterocyclic group, a heterocyclyloxy group, a carboxyl group, a nitro group, or a cyano group, each of these groups optionally having a substituent;

where there are a plurality of $R^3$, they may be the same or different;

each $R^4$ represents a hydrogen atom, an alkyl group, an aryl group, an arylalkyl group, or a monovalent heterocyclic group, each of these groups optionally having a substituent;

the $R^4$s may be the same or different;

the two $R^4$s may be connected to form a ring;

each $X^3$ represents a chlorine atom, a bromine atom, or an iodine atom;

the $X^3$s may be the same or different;

each f represents an integer of from 0 to 2; and the f's may be the same or different.

[Chemical formula 115]

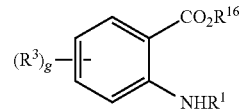

(13)

wherein $R^3$ is the same as in the above-described formula (12);

$R^1$ represents a hydrogen atom, an alkyl group, an aryl group, an arylalkyl group, an acyl group, or a monovalent heterocyclic group, each of these groups optionally having a substituent;

$R^{16}$ represents an alkyl group, an aryl group, an arylalkyl group, or a monovalent heterocyclic group, each of these groups optionally having a substituent; and g represents an integer of from 0 to 4.

[Chemical formula 116]

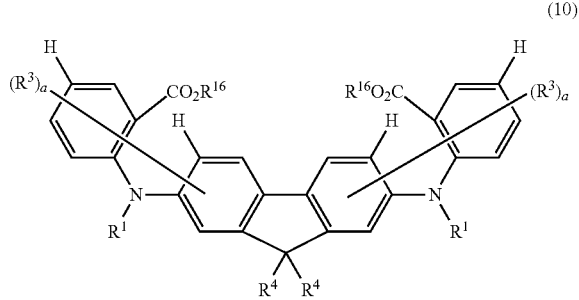

(10)

wherein each $R^1$ represents a hydrogen atom, an alkyl group, an aryl group, an arylalkyl group, an acyl group, or a monovalent heterocyclic group, each of these groups optionally having a substituent;

the $R^1$s may be the same or different;

each $R^3$ represents an alkyl group, an alkoxy group, an aryl group, an aryloxy group, an arylalkyl group, an arylalkoxy group, an alkenyl group, an arylalkenyl group, an alkynyl group, an arylalkynyl group, an amino group, a silyl group, a halogen atom, an acyl group, an acyloxy group, a carbamoyl group, a monovalent heterocyclic group, a heterocyclyloxy group, a carboxyl group, a nitro group, or a cyano group, each of these groups optionally having a substituent;

where there are a plurality of $R^3$, they may be the same or different;

each $R^4$ represents a hydrogen atom, an alkyl group, an aryl group, an arylalkyl group, or a monovalent heterocyclic group, each of these groups optionally having a substituent;

the $R^4$s may be the same or different;

the two $R^4$s may be connected to form a ring;

each $R^{16}$ represents an alkyl group, an aryl group, an arylalkyl group, or a monovalent heterocyclic group, each of these groups optionally having a substituent;

the $R^{16}$s may be the same or different;

each a represents an integer of from 0 to 5; and the a's may be the same or different.

In formulae (10), (12), and (13), the groups represented by $R^1$, $R^3$, $R^4$, and $R^{16}$ and the integer represented by a are the same as those described and exemplified for the above-described formula (1) or (2).

In formula (12), each f is an integer of from 0 to 2 and preferably 0.

In formula (13), g is an integer of from 0 to 4 and preferably 0.

Examples of the transition metal catalyst used in the reaction (1) may include palladium catalysts, nickel catalysts, and copper catalysts.

For example, the reaction (1) can be performed under the Ullmann coupling conditions in the presence of a copper catalyst and a base. The reaction (1) can be also performed under amination reaction conditions described in Angewandte Chemie, International Edition in English, (1995), 34(12), 1348. The temperature of the reaction (1) is 0 to 200° C. and preferably from room temperature to the boiling point of the solvent.

When the Ullmann coupling is used, examples of the base used in the reaction (1) may include inorganic strong bases such as sodium hydroxide, potassium hydroxide, potassium carbonate, and sodium carbonate.

Preferably, the solvent used in the reaction (1) is an aprotic solvent having a high boiling point. Examples of such a solvent may include pyridine, collidine, N,N-dimethylformamide, N-methyl-2-pyrrolidone, dimethyl sulfoxide, nitrobenzene, and dioxane. These solvents may be used alone or in combination of two or more.

A phase transfer catalyst or a crown ether may be added to facilitate the reaction.

The reaction (2) is the reaction of the above-described compound represented by formula (10) with the compound represented by the following formula (11) or a reducing agent to synthesize the compound represented by formula (9).

[Chemical formula 117]

$$R^{17}\text{-M} \qquad (11)$$

wherein $R^{17}$ represents an alkyl group, an alkoxy group, an aryl group, an aryloxy group, an arylalkyl group, an arylalkoxy group, an alkenyl group, an arylalkenyl group, an acyl group, an acyloxy group, a monovalent heterocyclic group, or a heterocyclyloxy group; and M represents a lithium atom or a monohalogenated magnesium.

[Chemical formula 118]

wherein each $R^1$ represents a hydrogen atom, an alkyl group, an aryl group, an arylalkyl group, an acyl group, or a monovalent heterocyclic group, each of these groups optionally having a substituent;

the $R^1$s may be the same or different;

each $R^2$ represents a hydrogen atom, an alkyl group, an alkoxy group, an aryl group, an aryloxy group, an arylalkyl group, an arylalkoxy group, an alkenyl group, an arylalkenyl group, an acyl group, an acyloxy group, a monovalent heterocyclic group, or a heterocyclyloxy group, each of these groups optionally having a substituent;

the $R^2$s may be the same or different;

two $R^2$ bonded to the same carbon atom may be connected to form a ring;

each $R^3$ represents an alkyl group, an alkoxy group, an aryl group, an aryloxy group, an arylalkyl group, an arylalkoxy group, an alkenyl group, an arylalkenyl group, an alkynyl group, an arylalkynyl group, an amino group, a silyl group, a halogen atom, an acyl group, an acyloxy group, a carbamoyl group, a monovalent heterocyclic group, a heterocyclyloxy group, a carboxyl group, a nitro group, or a cyano group, each of these groups optionally having a substituent;

where there are a plurality of $R^3$, they may be the same or different;

each $R^4$ represents a hydrogen atom, an alkyl group, an aryl group, an arylalkyl group, or a monovalent heterocyclic group, each of these groups optionally having a substituent;

the $R^4$s may be the same or different;

the two $R^4$s may be connected to form a ring;

each a represents an integer of from 0 to 5; and the a's may be the same or different.

In formula (11), the alkyl group, the alkoxy group, the aryl group, the aryloxy group, the arylalkyl group, the arylalkoxy group, the alkenyl group, the arylalkenyl group, the acyl group, the acyloxy group, the monovalent heterocyclic group, and the heterocyclyloxy group represented by $R^{17}$ are the same as those described and exemplified for $R^1$ in the above-described formula (1). Of these, the alkyl group, the aryl group, the arylalkyl group, and the monovalent heterocyclic group are preferred.

In formula (11), M represents a lithium atom or a monohalogenated magnesium. The monohalogenated magnesium represented by M is the same as that described and exemplified for the group capable of participating in polymerization which is represented by $X^1$ in formula (7).

Examples of the reducing agent may include lithium aluminum hydride and diisobutyl aluminum hydride.

When both $R^1$ in the above-described compound represented by formula (10) are a hydrogen atom, the equivalents of the above-described compound represented by formula (11) or the reducing agent is preferably 4 equivalents or more. When one of the $R^1$ in the above-described compound represented by formula (10) is a hydrogen atom, the equivalents of the above-described compound represented by formula (11) or the reducing agent is preferably 3 equivalents or more. When both $R^1$ in the above-described compound represented by formula (10) are not a hydrogen atom, the equivalents of the above-described compound represented by formula (11) or the reducing agent is preferably 2 equivalents or more.

Each $R^2$ in formula (9) is preferably a hydrogen atom, an alkyl group, an aryl group, an arylalkyl group, or a monovalent heterocyclic group and more preferably an alkyl group, an aryl group, an arylalkyl group, or a monovalent heterocyclic group.

Preferably, the reaction (2) is performed under an atmosphere of an inert gas such as an argon or nitrogen.

Examples of the solvent used in the reaction (2) may include saturated hydrocarbons such as pentane, hexane, heptane, octane, and cyclohexane; aromatic hydrocarbons such as benzene, toluene, ethyl benzene, and xylene; and ethers such as dimethyl ether, diethyl ether, methyl-tert-butyl ether, tetrahydrofuran, tetrahydropyran, and dioxane. These solvents may be used alone or in combination of two or more.

The temperature of the reaction (2) is −100° C. to the boiling point of the solvent and preferably −80° C. to room temperature.

The reaction (3) is the reaction of the above-described compound represented by formula (9) in the presence of an acid to synthesize the compound represented by the following formula (8).

[Chemical formula 119]

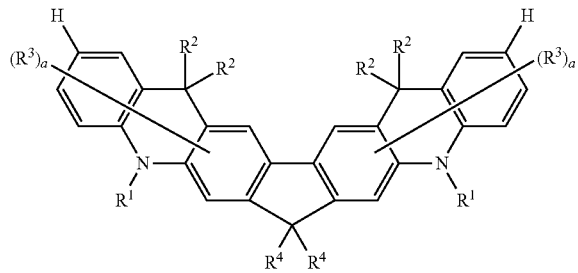

(8)

wherein each $R^1$ represents a hydrogen atom, an alkyl group, an aryl group, an arylalkyl group, an acyl group, or a monovalent heterocyclic group, each of these groups optionally having a substituent;

the $R^1$s may be the same or different;

each $R^2$ represents a hydrogen atom, an alkyl group, an alkoxy group, an aryl group, an aryloxy group, an arylalkyl group, an arylalkoxy group, an alkenyl group, an arylalkenyl group, an acyl group, an acyloxy group, a monovalent heterocyclic group, or a heterocyclyloxy group, each of these groups optionally having a substituent;

the $R^2$s may be the same or different;

two $R^2$ bonded to the same carbon atom may be connected to form a ring;

each $R^3$ represents an alkyl group, an alkoxy group, an aryl group, an aryloxy group, an arylalkyl group, an arylalkoxy group, an alkenyl group, an arylalkenyl group, an alkynyl group, an arylalkynyl group, an amino group, a silyl group, a halogen atom, an acyl group, an acyloxy group, a carbamoyl group, a monovalent heterocyclic group, a heterocyclyloxy group, a carboxyl group, a nitro group, or a cyano group, each of these groups optionally having a substituent;

where there are a plurality of $R^3$, they may be the same or different;

each $R^4$ represents a hydrogen atom, an alkyl group, an aryl group, an arylalkyl group, or a monovalent heterocyclic group, each of these groups optionally having a substituent;

the $R^4$s may be the same or different;

the two $R^4$s may be connected to form a ring;

each a represents an integer of from 0 to 5; and the a's may be the same or different.

The compound represented by formula (9) which is used as the raw material of the reaction (3) is more preferably a compound represented by the following formula (9-1).

[Chemical formula 120]

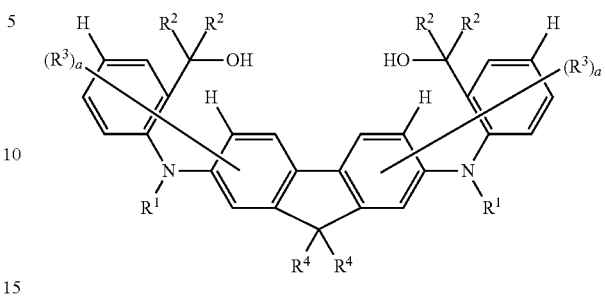

(9-1)

wherein $R^1$, $R^2$, $R^3$, $R^4$, and a are the same as in formula (9).

The acid used in the reaction (3) may be a protonic acid or a Lewis acid.

Examples of the protonic acid may include sulfonic acids such as methanesulfonic acid, trifluoromethanesulfonic acid, and p-toluenesulfonic acid; carboxylic acids such as formic acid, acetic acid, trifluoroacetic acid, and propionic acid; and inorganic acids such as sulfuric acid, hydrochloric acid, nitric acid, and phosphoric acid. Of these protonic acids, inorganic strong acids such as hydrochloric acid, sulfuric acid, and nitric acid are preferred.

Examples of the Lewis acid may include halogenated borides such as boron tribromide, boron trichloride, and a boron trifluoride ether complex; and halogenated metals such as aluminum chloride, titanium trichloride, titanium tetrachloride, manganese chloride, iron chloride(II), iron chloride (III), cobalt chloride, copper chloride(I), copper chloride(II), zinc chloride, aluminum bromide, titanium tribromide, titanium tetrabromide, manganese bromide, iron bromide(II), iron bromide(III), cobalt bromide, copper bromide(I), copper bromide(II), and zinc bromide.

These protonic acids and Lewis acids may be used alone or in combination of two or more.

Any of the above-described acids may be used as the solvent used in the reaction (3), but another solvent may be used. Examples of the solvent used may include saturated hydrocarbons such as pentane, hexane, heptane, octane, and cyclohexane; aromatic hydrocarbons such as benzene, toluene, xylene, and mesitylene; halogenated saturated hydrocarbons such as carbon tetrachloride, chloroform, dichloromethane, chlorobutane, bromobutane, chloropentane, bromopentane, chlorohexane, bromohexane, chlorocyclohexane, and bromocyclohexane; halogenated aromatic hydrocarbons such as chlorobenzene, dichlorobenzene, and trichlorobenzene; and nitro compounds such as nitromethane and nitrobenzene. These solvents may be used alone or in combination of two or more.

The temperature of the reaction (3) is −100° C. to the boiling point of the solvent and preferably 0 to 100° C.

The reaction (4) is the reaction of the above-described compound represented by formula (8) with a halogenation agent to synthesize the above-described compound represented by formula (7-1).

Preferably, the reaction (4) is performed under an atmosphere of an inert gas such as an argon or nitrogen.

Examples of the halogenation agent used in the reaction (4) may include N-halogeno compounds such as N-chlorosuccinimide, N-chlorophthalic imide, N-bromosuccinimide, N-bromophthalic imide, 4,4,5,5,-tetramethyl, 1,3-dibromo-5,5-dimethyl hydantoin, N-iodosuccinimide, and N-iodophthalic imide; halogen atoms such as chlorine and bromine;

and benzyltrimethylammonium tribromide. Of these, N-halogeno compounds are preferred.

Examples of the solvent used in the reaction (4) may include saturated hydrocarbons such as pentane, hexane, heptane, octane, and cyclohexane; aromatic hydrocarbons such as benzene, toluene, ethyl benzene, and xylene; halogenated saturated hydrocarbons such as carbon tetrachloride, chloroform, dichloromethane, chlorobutane, bromobutane, chloropentane, bromopentane, chlorohexane, bromohexane, chlorocyclohexane, and bromocyclohexane; halogenated aromatic hydrocarbons such as chlorobenzene, dichlorobenzene, and trichlorobenzene; alcohols such as methanol, ethanol, propanol, isopropanol, butanol, and tert-butyl alcohol; carboxylic acids such as formic acid, acetic acid, and propionic acid; ethers such as dimethyl ether, diethyl ether, methyl-tert-butyl ether, tetrahydrofuran, tetrahydropyran, and dioxane; amines such as trimethylamine, triethylamine, N,N,N',N'-tetramethylethylenediamine, and pyridine; and amides such as N,N-dimethylformamide, N,N-dimethylacetamide, N,N-diethylacetamide, N-methylmorpholine oxide, and N-methyl-2-pyrrolidone. These solvents may be used alone or in combination of two or more.

The temperature of the reaction (4) is −100° C. to the boiling temperature of the solvent and preferably −20 to 50° C.

<Composition>

A composition of the present invention is a composition comprising (a) the compound of the present invention and (b) at least one material selected from the group consisting of a hole transport material, an electron transport material, and a light-emitting material. The composition of the present invention may comprise a solvent (the composition of the present invention comprising a solvent is hereinafter referred to as a "liquid composition." Generally, such a composition may be referred to as an ink or an ink composition). In the composition of the present invention, the number of types of each of the compound of the present invention, the hole transport material, the electron transport material, the light-emitting material, and the solvent may be one, or a combination of two of more types may be used.

In the composition of the present invention, the ratio of the total amount of the hole transport material, the electron transport material, and the light-emitting material to the amount of the compound of the present invention is generally 1 to 10,000 parts by weight based on 100 parts by weight of the compound of the present invention, preferably 10 to 1,000 parts by weight, and more preferably 20 to 500 parts by weight.

Next, the liquid composition of the present invention will be described.

The ratio of the solvent in the liquid composition is generally 1 to 99.9 percent by weight based on the total weight of the liquid composition and preferably 80 to 99.9 percent by weight. A preferred viscosity of the liquid composition varies depending on the printing method used. However, for example, in an inkjet printing method or the like in which the liquid composition flows through an ejection device, the viscosity of the liquid composition at 25° C. is preferably 1 to 20 mPa·s so that clogging during ejection and flying deviation are prevented.

The liquid composition may further comprise an additive for adjusting viscosity and/or surface tension. Examples of such an additive may include a high-molecular weight compound for increasing viscosity (hereinafter referred to as a "thickener"), a poor solvent, a low-molecular weight compound for reducing viscosity, and a surfactant for reducing surface tension.

Any thickener can be used so long as it is soluble in the solvent used for the compound of the present invention and does not impede light emission and charge transport. Examples of such a solvent may include high-molecular weight polystyrene and polymethylmethacrylate. A poor solvent may be used as a thickener. More specifically, by adding a small amount of a poor solvent with respect to the solids in the liquid composition, viscosity can be increased.

The liquid composition of the present invention may comprise an anti-oxidant to improve storage stability. Examples of the anti-oxidant may include compounds that are soluble in the solvent used for the compound of the present invention and do not impede light emission and charge transport. A phenol-based anti-oxidant and a phosphorus-based anti-oxidant are preferred.

Examples of the solvent included in the liquid composition may include chlorine-based solvents such as chloroform, methylene chloride, 1,2-dichloroethane, 1,1,2-trichloroethane, chlorobenzene, and o-dichlorobenzene; ether-based solvents such as tetrahydrofuran, dioxane, and anisole; aromatic hydrocarbon-based solvents such as toluene and xylene; aliphatic hydrocarbon-based solvents such as cyclohexane, methyl cyclohexane, n-pentane, n-hexane, n-heptane, n-octane, n-nonane, and n-decane; ketone-based solvents such as acetone, methyl ethyl ketone, cyclohexanone, benzophenone, and acetophenone; ester-based solvents such as ethyl acetate, butyl acetate, ethyl cellosolve acetate, methyl benzoate, and phenyl acetate; polyalcohols such as ethylene glycol, ethylene glycol monobutyl ether, ethylene glycol monoethyl ether, ethylene glycol monomethyl ether, dimethoxyethane, propylene glycol, diethoxymethane, triethylene glycol monoethyl ether, glycerin, 1,2-hexanediol, and derivatives thereof; alcohol-based solvents such as methanol, ethanol, propanol, isopropanol, and cyclohexanol; sulfoxide-based solvents such as dimethyl sulfoxide; and amide-based solvents such as N-methyl-2-pyrrolidone and N,N-dimethylformamide. These solvents may be used alone or in combination of two or more. From the viewpoint of film forming properties and device characteristics, the number of types of solvents used is preferably two or more, more preferably 2 and 3, and particularly preferably 2.

When a combination of two types of solvents is used, one of them may be in a solid state at 25° C. In the combination of two solvents, one of them is preferably a solvent having a boiling point of 180° C. or higher and more preferably a solvent having a boiling point of 200° C. or higher, from the viewpoint of film forming properties. It is preferable, from the viewpoint of viscosity, that both the two solvents be solvents that can dissolve the compound of the present invention at a concentration of 1 percent by weight or higher at 60° C. and that at least one of the solvents be a solvent that can dissolve the compound of the present invention at a concentration of 1 percent by weight or higher at 25° C.

When a combination of three or more solvents is used, the amount of one of the three or more solvents that has the highest boiling point is preferably 40 to 90 percent by weight based on the total amount of the solvents and more preferably 50 to 90 percent by weight, from the viewpoint of viscosity and film forming properties.

The liquid composition may comprise water, a metal, and a salt thereof in an amount of 1 to 1,000 ppm (by weight). Examples of the metal may include lithium, sodium, calcium, potassium, iron, copper, nickel, aluminum, zinc, chromium, manganese, cobalt, platinum, and iridium. The liquid composition may comprise silicon, phosphorus, fluorine, chlorine, and bromine in an amount of 1 to 1,000 ppm (by weight).

The use of the liquid composition allows a film of the present invention to be easily produced by a coating method such as a spin coating method, a casting method, a microgravure coating method, a gravure coating method, a bar coating method, a roller coating method, a wire bar coating method, a dip coating method, a spray coating method, a screen printing method, a flexography method, an offset printing method, or an inkjet printing method.

<Film>

The film of the present invention is a film comprising the compound of the present invention, and examples of the type of the film may include a light-emitting film, a conductive film, and an organic semiconductor film.

The light-emitting film is useful for the formation of a light-emitting layer when a light-emitting device described later is produced.

The conductive film preferably has a surface resistance of 1 KΩ/square or smaller. The electric conductivity of the conductive film of the present invention can be increased by doping it with, for example, a Lewis acid or an ionic compound.

In the organic semiconductor film, a larger one of the electron mobility and hole mobility is preferably $1 \times 10^{-5}$ cm$^2$/V/sec or higher. An organic transistor can be produced by forming an organic semiconductor film on a Si substrate having formed thereon an insulating film of, for example, SiO$_2$ and a gate electrode, and forming a source electrode and a drain electrode using, for example, Au.

<Device>

A device of the present invention is a device including (a) electrodes comprising an anode and a cathode, and (b) an organic layer comprising the compound of the present invention, which is disposed between the electrodes, and one representative example of such a device is a light-emitting device (hereinafter referred to as a "light-emitting device of the present invention").

The light-emitting device of the present invention includes a pair of electrodes comprising an anode and a cathode, and a film of one layer (single layer type) or a plurality of layers (multi layer type) including a light-emitting layer, which is disposed between the electrodes. At least one of the layers in the film includes the compound of the present invention. The total amount of the compound of the present invention in the film is generally 0.1 to 100 percent by weight based on the total weight of the light-emitting layer and preferably 0.1 to 80 percent by weight. Preferably, in the light-emitting device of the present invention, the light-emitting layer includes the compound of the present invention as a light-emitting material.

When the light-emitting device of the present invention is of the single layer type, the film serves as the light-emitting layer, and the light-emitting layer comprises the compound of the present invention. When the light-emitting device of the present invention is of the multi layer type, the light-emitting device has, for example, any of the following configurations.
(a) anode/hole injection layer (hole transport layer)/light-emitting layer/cathode
(b) anode/light-emitting layer/electron injection layer (electron transport layer)/cathode
(c) anode/hole injection layer (hole transport layer)/light-emitting layer/electron injection layer (electron transport layer)/cathode Preferably, the anode of the light-emitting device of the present invention has a work function of 4.5 eV or higher. Any of metals, alloys, metal oxides, electric conductive compounds, and mixtures thereof can be used as the material of the anode. Examples of the material of the anode may include conductive metal oxides such as tin oxide, zinc oxide, indium oxide, and indium-tin oxide (ITO); metals such as gold, silver, chromium, and nickel; mixtures and stacked bodies of any of these conductive metal oxides and metals; inorganic conductive materials such as copper iodide and copper sulfide; organic conductive materials such as polyaniline, polythiophene (for example, PEDOT), and polypyrrole; and stacked bodies of ITO and any of these materials.

Any of metals, alloys, metal halides, metal oxides, electric conductive compounds, and mixtures thereof can be used as the material of the cathode of the light-emitting device of the present invention. Examples of the material of the cathode may include alkali metals (e.g., lithium, sodium, potassium, and cesium), and fluorides thereof and oxides thereof; alkaline-earth metals (e.g., magnesium, calcium, and barium), and fluorides thereof and oxides thereof; gold, silver, lead, aluminum, alloys and metal mixtures (e.g., sodium-potassium alloys, sodium-potassium mixed metals, lithium-aluminum alloys, lithium-aluminum mixed metals, magnesium-silver alloys, and magnesium-silver mixed metals); rare-earth metals (e.g., ytterbium); and indium.

Any known materials can be used as the materials of the hole injection layer and hole transport layer of the light-emitting device of the present invention. Examples of such materials may include carbazole derivatives, triazole derivatives, oxazole derivatives, oxadiazole derivatives, imidazole derivatives, polyarylalkane derivatives, pyrazoline derivatives, pyrazolone derivatives, phenylenediamine derivatives, arylamine derivatives, amino-substituted chalcone derivatives, styrylanthracene derivatives, fluorenone derivatives, hydrazone derivatives, stilbene derivatives, silazane derivatives, aromatic tertiary amine compounds, styrylamine compounds, aromatic dimethylidyne-based compounds, porphyrin-based compounds, polysilane-based compounds, poly(N-vinylcarbazole) derivatives, organic silane derivatives, the compound of the present invention, polymerized products comprising the above-described materials, and conductive polymers and oligomers such as aniline-based copolymers, thiophene oligomers, and polythiophene. These materials may be used alone or in combination of a plurality of components. Each of the hole injection layer and the hole transport layer may have a single layer structure of one or two or more of the above-described materials or have a multilayer structure including a plurality of layers having the same composition or different compositions.

Examples of the materials used for the electron injection layer and the electron transport layer of the light-emitting device of the present invention may include triazole derivatives; oxazole derivatives; oxadiazole derivatives; imidazole derivatives; fluorenone derivatives; anthraquinodimethane derivatives; anthrone derivatives; diphenylquinone derivatives; thiopyrandioxide derivatives; carbodiimide derivatives; fluorenylidene methane derivatives; distyrylpyrazine derivatives; aromatic ring tetracarboxylic anhydrides such as naphthalene tetracarboxylic anhydride and perylene tetracarboxylic anhydride; various metal complexes typified by metal complexes of phthalocyanine derivatives and 8-quinolinol derivatives, metal phthalocyanine, and metal complexes with benzoxazole or benzothiazole as ligands; organic silane derivatives; and the compounds of the present invention. Each of the electron injection layer and the electron transport layer may have a single layer structure of one or two or more of the above-described materials or have a multilayer structure including a plurality of layers having the same composition or different compositions.

In the light-emitting device of the present invention, an inorganic compound for an insulator and a semiconductor may be used as the materials used for the electron injection layer and the electron transport layer. When the electron injection layer and the electron transport layer are formed of an insulator or a semiconductor, current leakage can be effectively prevented to improve electron injection property. At least one metal compound selected from the group consisting of alkali metal chalcogenides, alkaline-earth metal chalcogenides, halides of alkali metals, and halides of alkaline-earth metals can be used as such an insulator. Preferred examples of the alkaline-earth metal chalcogenides may include CaO, BaO, SrO, BeO, BaS, and CaSe. Examples of the semiconductors forming the electron injection layer and the electron transport layer may include oxides, nitrides, and oxynitrides including at least one device selected from the group consisting of Ba, Ca, Sr, Yb, Al, Ga, In, Li, Na, Cd, Mg, Si, Ta, Sb, and Zn. These oxides, nitrides, and oxynitrides may be used alone or in combination of two or more.

In the light-emitting device of the present invention, a reducing dopant may be added to the interfacial region between the cathode and the film in contact therewith. At least one compound selected from the group consisting of alkali metals, oxides of alkaline-earth metals, alkaline-earth metals, rare-earth metals, oxides of alkali metals, halides of alkali metals, oxides of alkaline-earth metals, halides of alkaline-earth metals, oxides of rare-earth metals, halides of rare-earth metals, alkali metal complexes, alkaline-earth metal complexes, and rare-earth metal complexes is preferred as the reducing dopant.

The light-emitting layer of the light-emitting device of the present invention has the function of injecting holes from the anode or the hole injection layer and injecting electrons from the cathode or the electron injection layer when voltage is applied, the function of causing the injected charges (electrons and holes) to migrate by the force of the electric field, and the function of providing sites for recombination of the electrons and holes to generate light. Preferably, the light-emitting layer of the light-emitting device of the present invention comprises the compound of the present invention and may further comprise a host material with this compound serving as a guest material. Examples of the host material may include materials having a fluorene skeleton, materials having a carbazole skeleton, materials having a diarylamine skeleton, materials having a pyridine skeleton, materials having a pyrazine skeleton, materials having a triazine skeleton, and materials having an arylsilane skeleton. Preferably, the T1 (the energy level of the lowest triplet excited state) of the host material is higher than that of the guest material. More preferably, the difference in T1 is larger than 0.2 eV. The host material may be a low molecular compound or a polymer compound. A light-emitting layer in which the host material is doped with a light-emitting material such as any of the above-described metal complexes can be formed, for example, by applying a mixture of the host material and the light-emitting material or by co-deposition of these materials.

In the light-emitting device of the present invention, examples of the method of forming each layer may include vacuum deposition methods (e.g., resistive heating deposition method and an electron beam method), sputtering method, an LB method, a molecular stacking method, and coating methods (e.g., a casting method, a spin coating method, a bar coating method, a blade coating method, a roller coating, method gravure printing, screen printing, and an inkjet printing method). Of these, coating is preferably used to form a film because the production step can be simplified. In the coating methods, a layer can be formed by dissolving the compound of the present invention in a solvent to prepare a coating solution, coating a desired layer (or electrode) with the coating solution, and drying the coating solution. The coating solution may comprise a resin serving as a host material and/or a binder. The resin may be dissolved or dispersed in the solvent. A non-conjugated macromolecule (for example, polyvinylcarbazole) or a conjugated macromolecule (for example, a polyolefin-based macromolecule) can be used as the resin. More specifically, the resin can be selected according to the purpose from, for example, polyvinyl chloride, polycarbonate, polystyrene, polymethyl methacrylate, polybutyl methacrylate, polyester, polysulfone, polyphenylene oxide, polybutadiene, poly(N-vinylcarbazole), hydrocarbon resins, ketone resins, phenoxy resins, polyamide, ethyl cellulose, vinyl acetate, ABS resins, polyurethane, melamine resins, unsaturated polyester resins, alkyd resins, epoxy resins, and silicon resins. The solution may comprise an anti-oxidant and a viscosity modifier as optional components.

The compound of the present invention can be used for production of a photoelectric cell.

The photoelectric cell may be a photovoltaic cell. Examples of the photoelectric cell may include a photoelectric cell in which a layer comprising the compound of the present invention is disposed between a pair of electrodes at least one of which is transparent or translucent; and a photoelectric cell having a comb-shaped electrode formed on a layer comprising the compound of the present invention which is deposited on a substrate. To improve characteristics, a fullerene or a carbon nanotube may be mixed.

Methods of producing a photovoltaic cell include a method described in Japanese Patent No. 3146296. Examples of the production method may include a method including forming a layer (film) comprising the compound of the present invention on a substrate having a first electrode and forming a second electrode on the formed layer; and a method including forming a layer (film) comprising the compound of the present invention on a pair of comb-shaped electrodes formed on a substrate. One of the first and second electrodes is transparent or translucent.

The light-emitting device of the present invention can be used for a surface light source, a display apparatus such as a segment display apparatus or a dot-matrix display apparatus, and a backlight of a liquid crystal display apparatus.

To obtain planar light emission using the light-emitting device of the present invention, a planar anode and a planar cathode are arranged in an overlapping manner. To obtain patterned light emission, the following methods can be used: a method in which a mask having a patterned window is disposed on the surface of the planar light-emitting device; a method in which an organic layer in non-light-emitting portions is formed to have a very large thickness so that substantially no light is emitted therefrom; and a method in which one or both of the anode and cathode are formed into a pattern shape. A segment type display device that can display a number, a letter, and a simple symbol can be obtained by forming a pattern by any of the above-described methods and arranging some electrodes so that they can be switched on/off independently. To obtain a dot-matrix display apparatus, anodes and cathodes are formed into a stripe pattern and arranged orthogonal to each other. A partial color display and a multi-color display can be achieved by a method in which a plurality of polymer compounds with different light emission colors are applied to different portions or a method in which a color filter or a fluorescence conversion filter is used. The dot-matrix display apparatus may be driven passively or driven actively by combining it with, for example, TFTs. These display apparatuses can be used as display units of computers, TV sets, portable terminals, mobile phones, car navigations, view finders of video cameras, etc.

The above-described planar light-emitting device is of the thin self light-emitting type and can be suitably used as a surface light source for a backlight of a liquid crystal display apparatus or a surface light source for illumination. When a flexible substrate is used, the light-emitting device can also be used as a curved light source and a display apparatus.

EXAMPLES

Next, the present invention will be described with reference to Examples, but the present invention is not limited thereto. NMR, LC-MS, number-average molecular weight, weight-average molecular weight, ionization potential, and fluorescence wavelength measurements were performed by the following methods.

(i) NMR 5 to 10 mg of a measurement sample was dissolved in 0.5 mL of a deuterated solvent, and measurement was performed using MERCURY300 (product name, a product of Varian, Inc).

(ii) LC-MS

A measurement sample was dissolved in chloroform or tetrahydrofuran at a concentration of about 2 mg/mL. 1 μL of the prepared solution was injected into an LC-MS (product name: 1100LCMSD, a product of Agilent Technologies), and measurement was performed using L-column 2 ODS (3 μm) (a product of Chemicals Evaluation and Research Institute, Japan, inner diameter: 2.1 mm, length: 100 mm, particle size: 3 μm).

(iii) Number-Average Molecular Weight and Weight-Average Molecular Weight

For number-average molecular weight and weight-average molecular weight, GPC (product name: LC-10Avp, a product of Shimadzu Corporation) were used to obtain the polystyrene-equivalent number-average molecular weight and polystyrene-equivalent weight-average molecular weight. A measurement sample was dissolved in tetrahydrofuran at a concentration of about 0.5 percent by weight. 50 μL of the prepared solution was injected into the GPC. Tetrahydrofuran was used as the mobile phase of the GPC and allowed to flow at a flow rate of 0.6 mL/min. Two TSKgel SuperHM-H columns (a product of TOSOH Corporation) and one TSKgel SuperH2000 column (a product of TOSOH Corporation) were connected in series, and measurement was performed using a differential refractive index detector (RID-10A, a product of Shimadzu Corporation) as a detector.

(iv) Ionization potential

A 0.8 percent by weight solution of a measurement sample in toluene was prepared, and a quartz plate was spin-coated with the prepared solution to form a film of the measurement sample. The film was subjected to measurement using Photoelectron Spectrometer in air, AC-2 (a product of RIKEN KEIKI Co., Ltd).

(v) Light Emission Wavelength

A quartz plate was spin-coated with a 0.8 percent by weight solution of a measurement sample in toluene to produce a film of the measurement sample. The film was exited at a wavelength of 350 nm to measure the light emission wavelength of the measurement sample using a spectrofluorometer (a product name: Fluorolog, product of HORIBA Ltd.).

Example 1

Synthesis of Compound (I)

[Chemical formula 121]

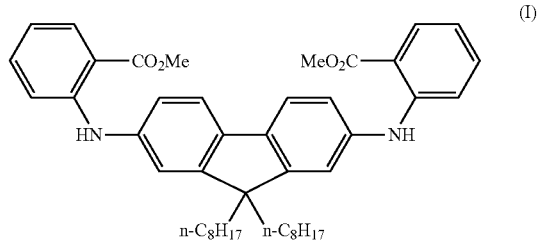

(I)

Gas in a 300 mL four-neck flask was replaced with nitrogen. Then 5.65 g of methyl anthranilate and 10.00 g of 2,7-dibromo-9,9-dioctylfluorene were dissolved in 200 mL of anhydrous toluene, and the obtained solution was bubbled with argon for 30 minutes. 8.91 g of cesium carbonate, 43 mg of tris(dibenzylideneacetone)dipalladium, and 53 mg of tri(tert-butyl)phosphine tetrafluoroborate were added to the prepared solution, and the mixture was refluxed. The mixture was refluxed for 90 hours while 26.1 g of cesium carbonate was further added. The product was filtrated through a glass filter covered with Celite and then washed with toluene. The solvent was removed by evaporation to obtain 13.07 g of a yellow liquid. The yellow liquid was dissolved in hexane and filtrated through a glass filter covered with 50 g of silica gel, and the silica gel was washed with toluene. The solvent was removed by evaporation to obtain 13.13 g of a crude product of compound (I). The product was used for the subsequent process without purification.

$^1$H-NMR (CDCl$_3$) δ (ppm)=0.71 (4H, br), 0.82 (6H, t), 1.08-1.20 (20H, m), 1.87-1.93 (4H, m), 3.93 (6H, s), 6.73 (2H, t), 7.16-7.34 (8H, m), 7.61 (2H, d), 7.98 (2H, d), 9.55 (2H, s)

$^{13}$C-NMR (CDCl$_3$) δ (ppm)=14.6, 22.9, 24.5, 29.6, 30.3, 32.1, 41.1, 52.1, 55.7, 112.0, 114.2, 117.1, 117.9, 120.1, 122.1, 132.0, 134.4, 137.1, 139.3, 149.0, 152.4, 169.5

LC-MS APCI, positive 689 ([M+H]$^+$, exact mass=688)

Example 2

Synthesis of Compound (II)

[Chemical formula 122]

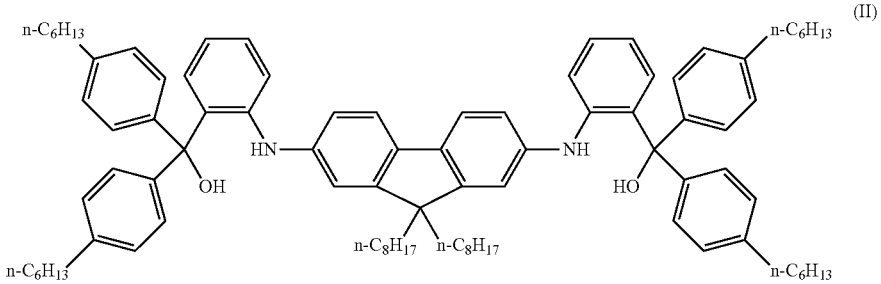

(II)

Gas in a 1 L four-neck flask was replaced with nitrogen. Then 24.50 g of 4-bromo-n-hexylbenzene was dissolved in 245 mL of anhydrous THF, and the solution was cooled to −78° C. 63.5 mL of n-butyl lithium (a 1.6M hexane solution) was added dropwise to the solution over 10 minutes, and the resultant mixture was stirred for 2 hours while the temperature was maintained. Then a solution obtained by dissolving 10.00 g of the previously synthesized compound (I) in 100 mL of anhydrous THF was added dropwise to the mixture over 30 minutes. The temperature of the mixture was gradually increased to room temperature, and the mixture was stirred for 6 hours. The resultant mixture was cooled to 0° C., and 200 mL of water was added dropwise. After the organic layer was separated from the aqueous layer, the aqueous layer was extracted a plurality of times with 200 mL of ethyl acetate, and a plurality of extracted organic layers were combined, washed with water and saturated brine, and dried over sodium sulfate. The solvent was removed by evaporation to obtain 25.51 g of a crude product of compound (II). The product was used for the subsequent process without purification.

$^1$H-NMR (CDCl$_3$) δ (ppm)=0.65 (4H, br), 0.84-0.95 (18H, m), 1.08-1.39 (44H, m), 1.56-1.65 (8H, m), 1.74-1.79 (4H, m), 2.52-2.62 (8H, m), 4.88 (2H, s), 5.80 (2H, s), 6.55 (2H, d), 6.63 (2H, m), 6.77-6.82 (4H, m), 7.03-7.40 (22H, m)

$^{13}$C-NMR (300 MHz, CDCl$_3$) δ (ppm)=14.3, 14.3, 22.7, 22.9, 29.3, 29.4, 30.4, 31.6, 31.7, 31.8, 31.9, 32.0, 32.1, 34.0, 35.5, 35.9, 36.3, 82.8, 125.8, 127.9, 128.4, 128.5, 128.7, 130.5, 131.5, 142.4, 143.4

LC-MS API-ES, positive 1312 ([M+K]$^+$, exact mass=1273) API-ES, negative 1308 ([M+Cl]$^-$, exact mass=1273)

Example 3

Synthesis of Compound (III)

[Chemical formula 123]

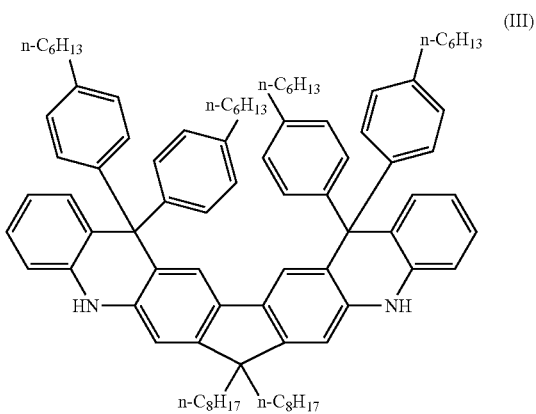

(III)

22.00 g of the compound (II) obtained above was dissolved in 220 mL of acetic acid. 5.8 mL of hydrochloric acid was added dropwise to the prepared solution, and the mixture was stirred at room temperature for 1 hour and stirred at 110° C. for 9 hours. After allowed to cool, the mixture was poured into 700 mL of water, and the resultant solution was subjected to suction filtration. The obtained residue was dissolved in 200 mL of toluene. 100 mL of water was added thereto, and the organic layer was separated from the aqueous layer. The aqueous layer was extracted a plurality of times with 200 mL of toluene. A plurality of extracted organic layers were combined, washed with water and saturated brine, and dried over magnesium sulfate. The solvent was removed by evaporation to obtain 16.64 g of a crude product of compound (III). 160 mL of hexane and 6 mL of ethyl acetate were added to the crude product, and the mixture was refluxed to dissolve the crude product. The resultant solution was allowed to slowly cool to room temperature, and the crystals were filtered to obtain 6.49 g of compound (III).

$^1$H-NMR (CDCl$_3$) δ (ppm)=0.80-0.94 (18H, m), 1.08-1.43 (48H, m), 1.54-1.63 (12H, m), 2.52-2.63 (8H, m), 6.80 (4H, br), 7.08 (2H, s), 7.17 (2H, d), 7.26 (2H, d), 6.90-7.40 (20H, m)

$^{13}$C-NMR (CDCl$_3$) δ (ppm)=14.4, 22.9, 29.5, 29.6, 29.8, 31.6, 31.7, 31.8, 31.9, 32.0, 32.1, 36.0, 36.1, 36.3, 40.2, 51.2, 126.0, 128.5, 128.7

LC-MS APCI, positive 1237 ([M+H]$^+$, exact mass=1236)

Example 4

Synthesis of Compound (IV)

[Chemical formula 124]

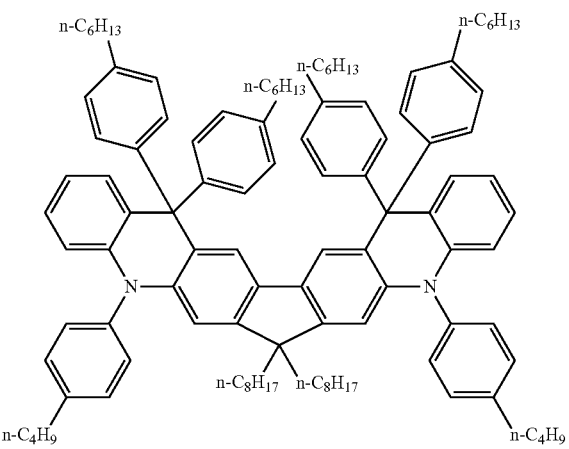

(IV)

Gas in a 100 mL two-neck flask was replaced with nitrogen. Then 0.90 g of compound (III) synthesized above and 0.35 g of 1-bromo-4-n-butylbenzene were placed in the flask and dissolved in 15 mL of toluene. The obtained solution was bubbled with argon for 30 minutes. Then 3.5 mg of tris(dibenzylideneacetone)bispalladium, 2.2 mg of tri(tert-butyl)phosphinetetrafluoroborate, and 0.15 g of sodium tert-butoxide were added, and the resultant mixture was stirred at 110° C. for 2 hours. After the mixture was allowed to cool, 10 mL of water was added, and the organic layer was separated from the aqueous layer. The aqueous layer was extracted a plurality of times with toluene, and a plurality of extracted organic layers were combined and washed with water and saturated brine. After the product was filtrated through a glass filter covered with 10 g of silica gel, the solvent was removed by evaporation to obtain 1.12 g of a crude product of compound (IV).

$^1$H-NMR (CDCl$_3$) δ (ppm)=0.52 (4H, br), 0.83-0.98 (28H, m), 1.09-1.50 (48H, m), 1.56-1.72 (12H, m), 2.57 (8H, t), 2.70 (4H, t), 6.23 (2H, s), 6.39 (2H, d), 6.67 (2H, s), 6.83-6.91 (14H, m), 6.99 (12H, d), 7.27 (4H, d)

LC-MS APCI, positive 1502 ([M+H]$^+$, exact mass=1501)

Example 5

Synthesis of Compound (V)

[Chemical formula 125]

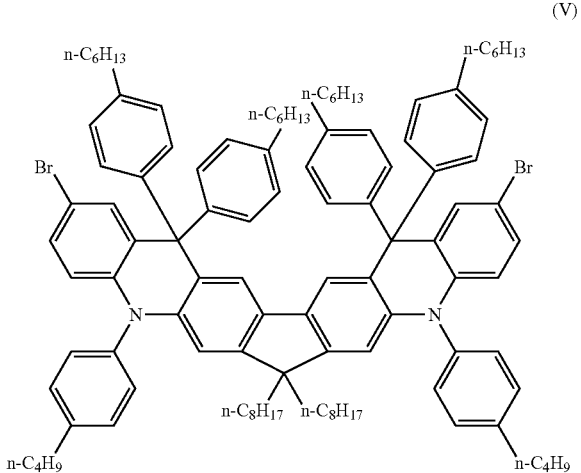

(V)

Gas in a 500 mL jacketed separable flask was replaced with nitrogen. The flask was charged with 6.00 g of compound (IV) and 60 mL of dichloromethane, and the mixture was stirred. After the mixture was cooled to −19° C., 1.466 g of N-bromosuccinimide (NBS) in a solid form was added. The resultant mixture was stirred at −20° C. for 29 hours. Then an aqueous solution of sodium thiosulfate was added dropwise, and the temperature was increased to 0° C. After the organic layer was separated from the aqueous layer, the aqueous layer was extracted a plurality of times with 50 mL of chloroform, and a plurality of extracted organic layers were combined and filtrated through a glass filter covered with 20 g of silica gel. The solvent was removed by evaporation to obtain 7.67 g of a crude product of compound (V). The crude product was purified by silica gel column chromatography (silica gel: 70 g, hexane:toluene=100:1 (volume ratio)) to obtain a light yellow viscous liquid. 100 mL of methanol was added to the obtained liquid, refluxed, and cooled, and a white solid was thereby obtained. The white solid was collected by filtration and recrystallized from 30 mL of acetone to obtain 5.67 g of compound (V).

$^1$H-NMR (THF-d$_8$) δ (ppm)=0.64 (4H, br), 0.90-1.78 (88H, m), 2.68 (8H, t), 2.77 (4H, t), 6.34 (2H, d), 6.39 (2H, s), 6.66 (2H, s), 6.87 (8H, d), 6.97 (4H, d), 7.09 (8H, d), 7.14-7.16 (4H, m), 7.40 (4H, d)

$^{13}$C-NMR (THF-d$_8$) δ (ppm)=15.5, 15.7, 24.4, 25.0, 31.3, 31.4, 31.8, 33.6, 33.9, 34.1, 35.6, 37.3, 37.6, 41.9, 56.3, 58.6, 110.7, 114.0, 117.9, 121.9, 129.5, 130.2, 131.2, 132.2, 132.4, 132.5, 132.6, 133.5, 134.7, 136.5, 140.6, 142.9, 143.3, 143.7, 145.1, 145.2, 151.3

LC-MS APCI, positive 1658 ([M+H]$^+$, exact mass=1657)

Example 6

Synthesis of Polymer Compound 1

0.533 g of 2,7-bis(1,3,2-dioxaborolane-2-yl)-9,9-di-n-octylfluorene, 1.660 g of compound (V), 0.7 mg of dichlorobis(triphenylphosphine)palladium, 0.129 g of trioctylmethylammonium chloride (product name: Aliquat336, a product of Aldrich), and 20 mL of toluene were mixed under a nitrogen atmosphere, and the mixture was heated to 90° C. 5.4 mL of a 17.5 percent by weight aqueous solution of sodium carbonate was added dropwise to the obtained mixed solution, and the resultant mixture was refluxed for 6 hours. Then 0.01 g of phenylboronic acid was added, and the resultant mixture was further refluxed for 4 hours. 6 mL of a 10 percent by weight aqueous solution of sodium diethyldithiocarbamate was added to the mixture, and the resultant mixture was stirred at 85° C. for 2 hours. After cooling, the mixture was washed twice with 13 mL of water, twice with 13 mL of a 3 percent by weight aqueous solution of acetic acid, and twice with 13 mL water. The obtained solution was added dropwise to 150 mL of methanol, and the precipitate was collected by filtration. The obtained precipitate was dissolved in 30 mL of toluene and followed by purification by passing through a column in which silica gel was covered with active alumina to purify the precipitate. The obtained toluene solution was added dropwise to 150 mL of methanol, and the mixture was stirred. The obtained precipitate was collected by filtration and dried to obtain 1.24 g of polymer compound 1 represented by the following formula. The number-average molecular weight of polymer compound 1 in terms of polystyrene was 4.6×10$^4$, and its weight-average molecular weight in terms of polystyrene was 1.0×10$^5$.

[Chemical formula 126]
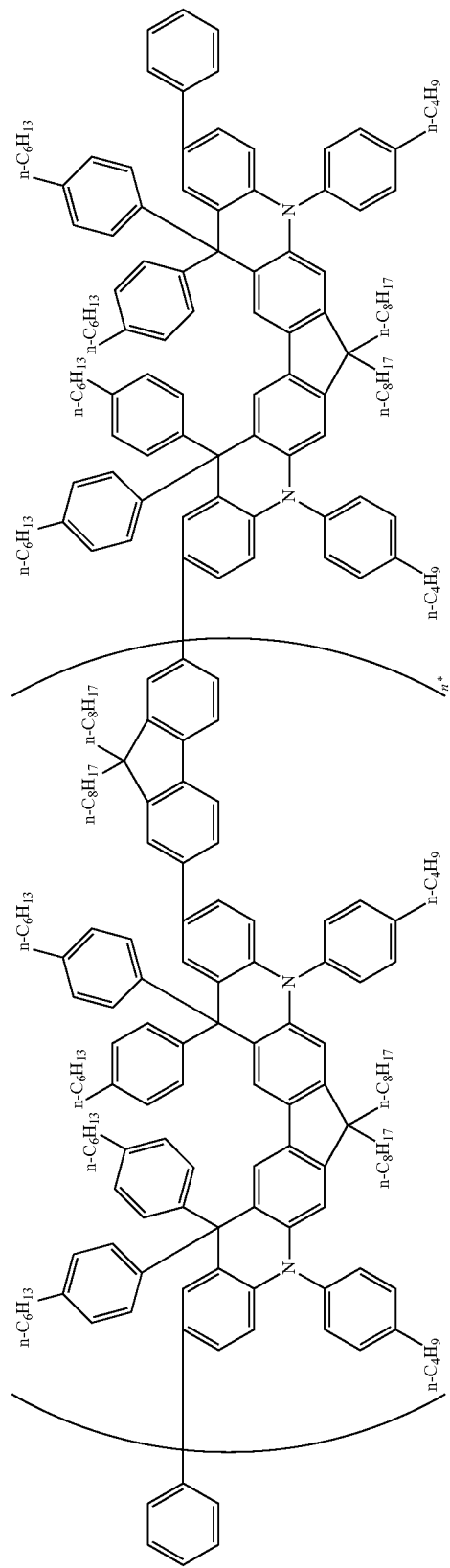

wherein n* represents the number of repeating units.

Synthesis Example 1

Synthesis of Polymer Compound 2

2.101 g of 2,7-bis(1,3,2-dioxaborolane-2-yl)-9,9-di-n-octylfluorene, 3.644 g of 2,7-bis{(4-bromophenyl)(4-methylphenyl)amino}-9,9-di(n-octyl)fluorene, 2.7 mg of palladium acetate, 29.6 mg of tris(o-tolyl)phosphine, 0.517 g of trioctylmethylammonium chloride (product name: Aliquat336, a product of Aldrich), and 40 mL of toluene were mixed under a nitrogen atmosphere, and the mixture was heated to 90° C.

10.9 mL of a 17.5 percent by weight aqueous solution of sodium carbonate was added dropwise to the obtained mixed solution, and the mixture was refluxed for 6 hours. Then 0.1 g of phenylboronic acid was added, and the resultant mixture was further refluxed for 2 hours. Then 24 mL of a 10 percent by weight aqueous solution of sodium diethyldithiocarbamate was added to the mixture, and the resultant mixture was stirred at 85° C. for 1 hour. After cooling, the mixture was washed twice with 52 mL of water, twice with 52 mL of a 3 percent by weight aqueous solution of acetic acid, and then twice with 52 mL of water. The obtained solution was added dropwise to 620 mL of methanol, and the precipitate was collected by filtration. The obtained precipitate was dissolved in 120 mL of toluene and followed by purification by passing through a column in which silica gel was covered with active alumina to purify the precipitate. The obtained toluene solution was added dropwise to 620 mL of methanol, and the mixture was stirred. The obtained precipitate was collected by filtration and dried to obtain 2.80 g of polymer compound 2 represented by the following formula. The number-average molecular weight of polymer compound 2 in terms of polystyrene was $6.6 \times 10^4$, and its weight-average molecular weight in terms of polystyrene was $2.2 \times 10^5$.

[Chemical formula 127]

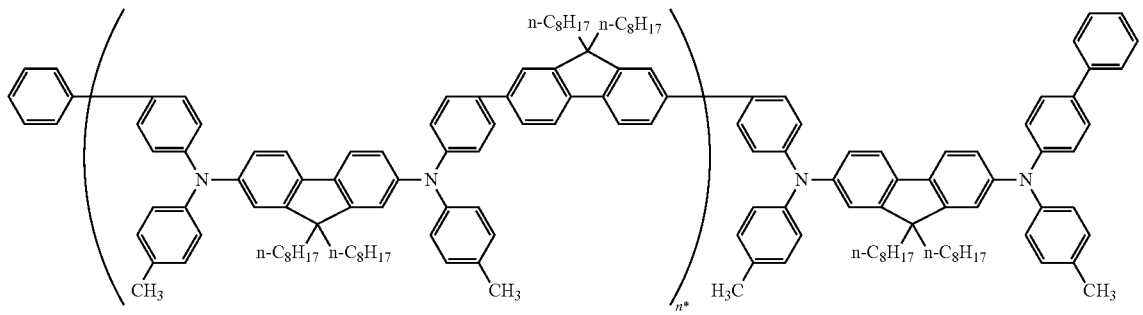

wherein n* represents the number of repeating units.

Synthesis Example 2

Synthesis of Compound (VI)

[Chemical formula 128]

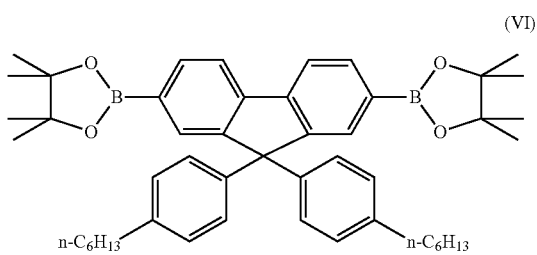

(VI)

A flask purged with nitrogen was charged with 61 g of 2,7-dibromo-9,9-bis(4-n-hexylphenyl)fluorene (synthesized according to a method described in WO2009-131255), and the compound was dissolved in 1 L of anhydrous tetrahydrofuran. The solution was cooled to −78° C. in a dry ice/acetone bath, and 95 mL of n-butyl lithium (a 2.5M hexane solution) was added dropwise while the rate of dropwise addition was controlled so that the temperature was maintained at −70° C. or lower. After completion of dropwise addition, the mixture was stirred at −78° C. for 6 hours, and 52.3 g of 2-isopropoxy-4,4,5,5-tetramethyl-1,3,2-dioxaborolane was added dropwise while the rate of dropwise addition was controlled so that the temperature was maintained at −70° C. or lower. The temperature was increased to room temperature, and the mixture was stirred overnight. Then the mixture was cooled to −30° C., and 143 mL of a hydrochloric acid/diethyl ether solution was added dropwise. After completion of dropwise addition, the temperature was increased to room temperature, and the reaction mixture was concentrated. 1 L of toluene was added, and the suspension was filtrated through a glass filter covered with silica gel and then washed with toluene. The filtrate and washings were concentrated, and recrystallization from 80 mL of toluene and 1.5 L of acetonitrile was performed. The recrystallization was further repeated 5 times. The obtained crystals were dried under reduced pressure in a vacuum dryer to obtain 45 g of compound (VI).

$^1$H-NMR (CDCl$_3$) δ (ppm)=0.86 (6H, t), 1.25 (24H, s), 1.25-1.36 (12H, m), 1.53-1.61 (4H, m), 2.51 (4H, t), 7.00 (4H, d), 7.11 (4H, d), 7.76 (2H, d), 7.80 (2H, s), 7.81 (2H, d)

$^{13}$C-NMR (CDCl$_3$) δ (ppm)=14.4, 22.7, 25.2, 29.4, 31.6, 32.0, 35.8, 65.3, 83.9, 120.0, 128.4, 128.6, 132.7, 134.4, 141.2, 143.1, 143.2, 151.9

LC-MS ESI, positive 777 ([M+K]$^+$, exact mass=738)

Example 7

Synthesis of Polymer Compound 3

1.26 g of 2,7-bis(4,4,5,5-tetramethyl-1,3,2-dioxaborolane-2-yl)-9,9-bis(3-n-hexylphenyl)fluorene (synthesized according to a method described in WO2010-013723), 0.19 g of 2,7-dibromo-9,9-di(n-octyl)fluorene, 0.078 g of 2,7-dibromo-9,9-di(4-pentene-1-yl)fluorene (synthesized according to a method described in WO2010-013723), 0.090 g of 2,7-dibromo-9,9-bis(bicyclo[4,2,0]octa-1,3,5-triene-3-yl)fluorene (synthesized according to a method described in WO2008-38747), 1.69 g of compound (V), 0.4 mg of palladium acetate, 2.4 mg of tris(o-methoxyphenyl)phosphine, and 38 mL of toluene were mixed under a nitrogen flow, and the mixture was heated to 105° C. 6 mL of a 20 percent by weight aqueous solution of tetraethylammonium hydroxide was added dropwise to the obtained reaction mixture, and the resultant mixture was refluxed for 3 hours. Then 200 mg of phenylboronic acid was added, and the resultant mixture was further refluxed for 17 hours. Then 20 mL of a 1.8M aqueous solution of sodium diethyldithiocarbamate was added, and the resultant mixture was stirred at 80° C. for 4 hours. The mixture was cooled to room temperature, and the organic layer was separated. The organic layer was washed three times with 22 mL of water, three times with 22 mL of a 3 percent by weight aqueous solution of acetic acid, and then three times with 22 ml of water and was purified through a column in which silica gel was covered with active alumina. The obtained toluene solution was added dropwise to 250 mL of methanol, and the mixture was stirred for 1 hour. The obtained solid was collected by filtration and dried to obtain 1.8 g of polymer compound 3 represented by the following formula. The number-average molecular weight of polymer compound 3 in terms of polystyrene was $7.4 \times 10^5$, and its weight-average molecular weight in terms of polystyrene was $2.3 \times 10^6$.

bromo-9,9-di(n-octyl)fluorene, 0.09 g of 2,7-dibromo-9,9-di(4-pentene-1-yl)fluorene, 0.11 g of 2,7-dibromo-9,9-bis(bicyclo[4,2,0]octa-1,3,5-triene-3-yl)fluorene, 1.09 g of 2,7-bis{(4-bromophenyl)(4-methylphenyl)amino}-9,9-di(n-octyl)fluorene, 0.4 mg of palladium acetate, 2.8 mg of tris(o-methoxyphenyl)phosphine, and 44 mL of toluene were mixed under a nitrogen flow, and the mixture was heated to 105° C. 7 mL of a 20 percent by weight aqueous solution of tetraethylammonium hydroxide was added dropwise to the obtained reaction mixture, and the resultant mixture was refluxed for 4 hours. Then 244 mg of phenylboronic acid was added, and the mixture was further refluxed for 20 hours. Then 20 mL of a 1.8M aqueous solution of sodium diethyldithiocarbamate was added, and the resultant mixture was stirred at 80° C. for 4 hours. The mixture was cooled to room temperature, and the organic layer was separated. The organic layer was washed three times with 30 mL of water, three times with 30 mL of a 3 percent by weight aqueous solution of acetic acid, and then three times with 30 nil of water and was purified through a column in which silica gel was covered with active alumina.

[Chemical formula 129]

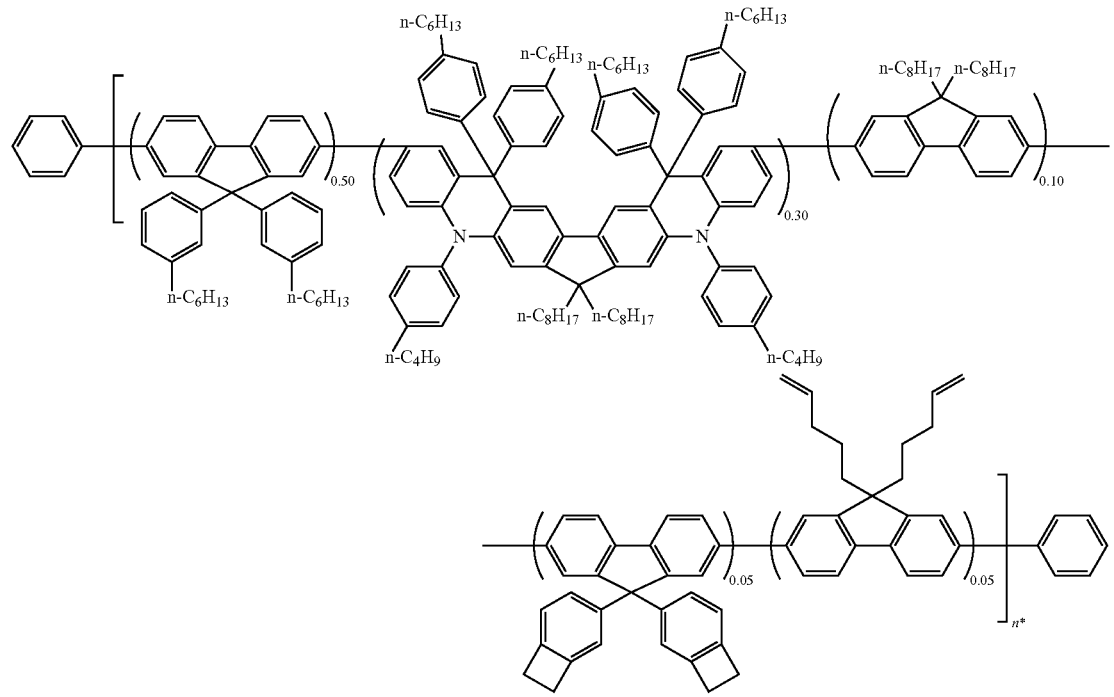

wherein each numerical subscript on the right of parentheses ( ) represents the copolymerization ratio of each repeating unit, and n* represents the number of repeating units.

Synthesis Example 3

Synthesis of Polymer Compound 4

1.48 g of 2,7-bis(4,4,5,5-tetramethyl-1,3,2-dioxaborolane-2-yl)-9,9-bis(3-n-hexylphenyl)fluorene, 0.22 g of 2,7-di- The obtained toluene solution was added dropwise to 300 mL of methanol, and the mixture was stirred for 1 hour. The obtained solid was collected by filtration and dried to obtain 1.7 g of polymer compound 4 represented by the following formula. The number-average molecular weight of polymer compound 4 in terms of polystyrene was $5.4 \times 10^5$, and its weight-average molecular weight in terms of polystyrene was $1.1 \times 10^6$.

[Chemical formula 130]

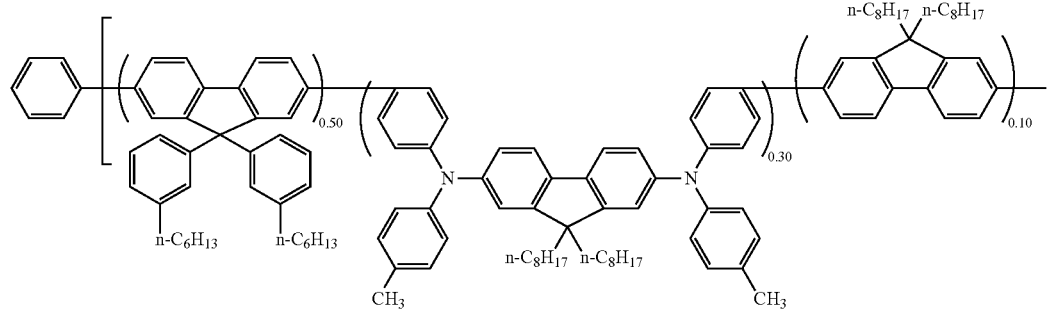

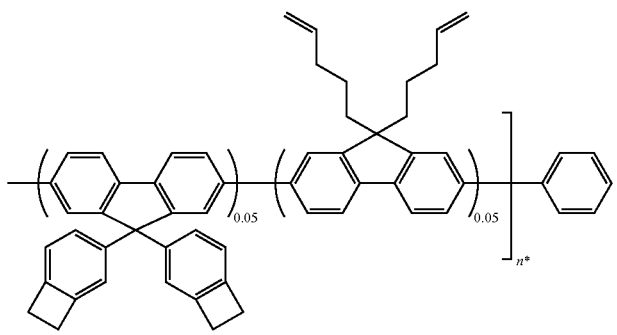

wherein each numerical subscript on the right of parentheses ( ) represents the copolymerization ratio of each repeating unit, and n* represents the number of repeating units.

Example 8

Synthesis of Polymer Compound 5

The reaction was performed in a glove box purged with nitrogen. A 100 mL reaction vessel was charged with 1.00 g of compound (V) and 0.45 g of 2,2'-bipyridyl, and the mixture was dissolved in 45 mL of anhydrous tetrahydrofuran. After the temperature was increased to 60° C., 0.45 g of bis(1,5-cyclooctadiene)nickel(0) was added, and the resultant mixture was stirred for 4 hours. 43 mL of water, 43 mL of methanol, and 2 mL of 25 percent by weight ammonia water were placed in a 500 mL beaker, and the reaction mass was poured into the prepared solution under stirring. After stirred for 30 minutes, the mixture was subjected to suction filtration to obtain 0.96 g of a crude product. 18 mL of toluene was added to the obtained crude product, and the mixture was subjected to suction filtration using a Kiriyama-rohto (Kiriyama-funnel) covered with Radiolite™. The resultant product was washed three times with 5 mL of toluene, and the filtrate and washings were filtrated through alumina and washed twice with 2 mL of toluene. 40 mL of 5 percent by weight hydrochloric acid was added to the obtained filtrate and washings. The resultant mixture was stirred at room temperature for 2 hours, and the organic layer was separated. 36 mL of 4 percent by weight ammonia water was added to the organic layer. The mixture was stirred at room temperature for 3 hours, and the resultant organic layer was separated. 36 mL of water was added to the organic layer. The resultant mixture was stirred at room temperature for 2.5 hours, and the resultant organic layer was separated. The organic layer was filtrated through filter paper and added dropwise to 100 mL of methanol, and the resultant mixture was stirred for 1 hour. The precipitated solid was filtrated and dried overnight in a vacuum dryer to obtain 0.63 g of polymer compound 5 represented by the following formula. The number-average molecular weight of polymer compound 5 in terms of polystyrene was $1.4 \times 10^4$, and its weight-average molecular weight in terms of polystyrene was $1.2 \times 10^5$.

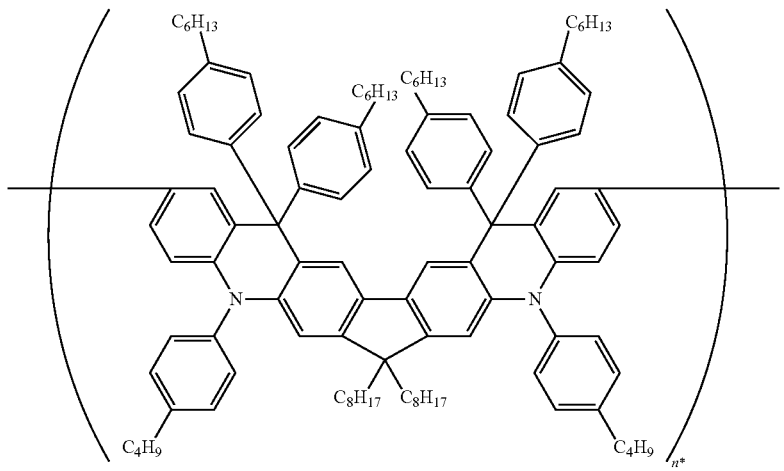

wherein n* represents the number of repeating units.

Example 9

Synthesis of Polymer Compound 6

2.393 g of compound (VI), 0.668 g of 2,7-bis(1,3,2-dioxaborolane-2-yl)-9,9-di-n-octylfluorene, 2.552 g of 2,7-dibromo-9,9-bis(3-n-hexylphenyl)fluorene (synthesized according to a method described in WO2010-13723), 0.897 g of compound (V), and 50 mL of toluene were mixed under a nitrogen atmosphere. After 3.2 mg of dichlorobis(triphenylphosphine)palladium (II) was added, 15 mL of tetraethylammonium hydroxide (a 20 percent by weight aqueous solution) was added dropwise over 5 minutes. Then the temperature of a bath was increased to 105° C., and the mixture was stirred for 20 hours. After the bath was removed, 0.96 g of (4,4,5,5-tetramethyl-1,3,2-dioxaborolane-2-yl)benzene and 3.2 mg of dichlorobis(triphenylphosphine)palladium (II) were added, and the resultant mixture was stirred at 105° C. for 4 hours. Then 0.96 g of bromobenzene was added, and the mixture was allowed to further react at 105° C. for 4 hours. After the bath temperature was lowered to 65° C., 50 mL of a 5 percent by weight aqueous solution of sodium diethyldithiocarbamate was added, and the mixture was further stirred for 4 hours. The organic layer was separated and poured into 500 mL of methanol, and the mixture was stirred at room temperature for 30 minutes. The obtained solid was filtrated and dried. The obtained crude product was dissolved in 150 mL of toluene and purified through a column in which silica gel was covered with active alumina. The obtained toluene solution was poured into 1 L of methanol, and the mixture was stirred at room temperature for 30 minutes. Then the obtained solid was filtrated and dried in a vacuum to obtain 3.68 g of polymer compound 6 represented by the following formula. The number-average molecular weight of polymer compound 6 in terms of polystyrene was $1.3 \times 10^5$, and its weight-average molecular weight in terms of polystyrene was $2.9 \times 10^5$.

[Chemical formula 132]

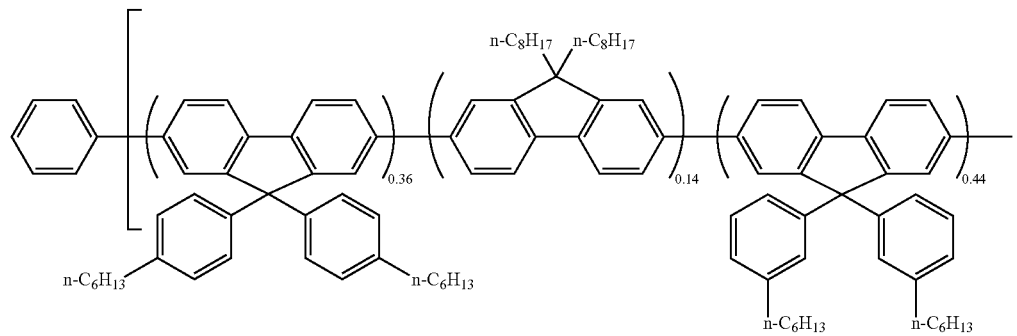

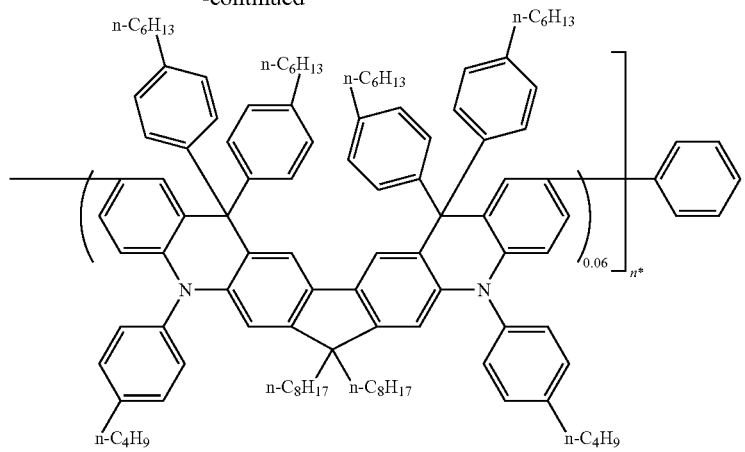

wherein each numerical subscript on the right of parentheses ( ) represents the copolymerization ratio of each repeating unit, and n represents the number of repeating units.

Synthesis Example 4

Synthesis of Polymer Compound 7

The same synthesis procedure as in that for polymer compound 6 was repeated except that 0.492 g of 2,7-bis{(4-bromophenyl)(4-methylphenyl)amino}-9,9-di-n-octylfluorene was used instead of compound (V). As a result, 3.86 g of polymer compound 7 represented by the following formula was obtained. The number-average molecular weight of polymer compound 7 in terms of polystyrene was $1.6 \times 10^5$, and its weight-average molecular weight in terms of polystyrene was $4.9 \times 10^5$.

[Chemical formula 133]

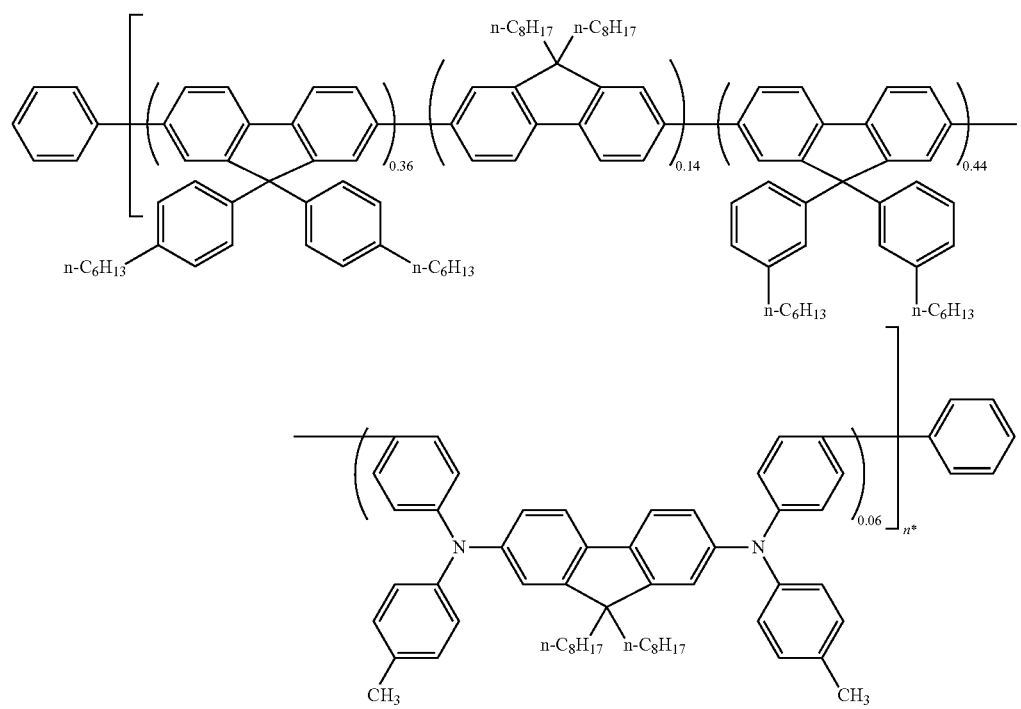

wherein each numerical subscript on the right of parentheses ( ) represents the copolymerization ratio of each repeating unit, and n* represents the number of repeating units.

Test Example 1

Evaluation of Hole Injection Property and Measurement of Light Emission Wavelength Evaluation of a hole injection property was performed using ionization potential as an indicator.

The ionization potential was measured according to (iv) described above.

The light emission wavelength was measured according to (v) described above, and the wavelength of the peak of light emission (λem) was determined.

The results showed that the absolute value of the measured value of ionization potential of the polymer compound 1 was smaller than that of the polymer compound 2. Therefore, the polymer compound 1 exhibits better hole injection property than the polymer compound 2.

The wavelength of the peak of light emission (λem) from the polymer compound 1 was shorter than that from the polymer compound 2. Therefore, it can be evaluated that the polymer compound 1 develops a blue color with a tone better than that of the polymer compound 2.

TABLE e

Results of measurements of ionization potential and light emission wavelength

| Polymer compound | Ionization potential (eV) | λem (nm) |
| --- | --- | --- |
| Polymer compound 1 | −5.11 | 434 |
| Polymer compound 2 | −5.26 | 440 |
| Polymer compound 3 | −5.12 | 444 |
| Polymer compound 4 | −5.27 | 448 |
| Polymer compound 5 | −5.02 | 420 |
| Polymer compound 6 | −5.22 | 446 |
| Polymer compound 7 | −5.29 | 448 |
| Compound (V) | −5.11 | 395 |

<Evaluation 1 of Hole Transport Property>

Hole-only devices that are devices allowing only holes to flow therethrough were produced to evaluate the hole transport property of the compounds of the present invention.

Device Example 1

HOD1-1

(1-1: Formation of Hole Injection Layer)

A glass substrate having an ITO anode formed thereon was subjected to UV ozone cleaning and then spin-coated with a composition for forming a hole injection layer to obtain a coating with a thickness of 60 nm.

The substrate having the coating formed thereon was heated at 200° C. for 10 minutes to insolubilize the coating and then naturally cooled to room temperature, and a hole injection layer was thereby deposited. An aqueous PEDOT:PSS solution (poly(3,4-ethylenedioxythiophene) polystyrene sulfonate, product name: Baytron) available from Starck-V Tech Ltd. was used as the composition for forming the hole injection layer.

(1-2: Formation of Hole Transport Layer)

The polymer compound 3 used as a hole transport material and xylene were mixed such that the ratio of the hole transport material was 1.75 percent by weight, and a composition for forming a hole transport layer was thereby obtained.

The hole injection layer obtained in (1-1) described above was spin-coated with the composition for forming a hole transport layer to obtain a coating having a thickness of 80 nm. The substrate having the coating formed thereon was heated at 180° C. for 60 minutes to insolubilize the coating and then naturally cooled to room temperature to form a hole transport layer.

(1-3: Formation of Cathode)

Gold was deposited to a thickness of 80 nm by vacuum deposition on the hole transport layer in the substrate having the anode, the hole injection layer, and the hole transport layer, which had been obtained in (1-2) described above, whereby a cathode was formed.

(1-4: Sealing)

The substrate having the stack which had been obtained in (1-3) described above was removed from the vacuum deposition apparatus, and sealed with sealing glass and a two-component epoxy resin under a nitrogen atmosphere to obtain a hole-only device (HOD1-1).

(Evaluation)

A voltage from −1 V to +20 V was applied to the hole-only device (HOD1-1) using a DC voltage/current generator, and current density [mA/cm$^2$] flowing into the device when the electric field intensity was 7×10$^5$ [V/cm$^2$] was measured. The results are shown in Table f.

In this evaluation, when an electric field with an intensity of 7×10$^5$ [V/cm$^2$] was applied to the device, no light emission caused by current excitation was observed. Therefore, the electron current flowing through the device was found to be much smaller than the hole current.

Device Example 2

HOD1-2

A hole-only device (HOD1-2) was produced and evaluated by the same procedure as in Device Example 1 except that, instead of the polymer compound 3, a mixture of the polymer compound 3 and the polymer compound 4 in a weight ratio of 1:1 was used as the hole transport material.

In this evaluation, when an electric field with an intensity of 7×10$^5$ [V/cm$^2$] was applied to the device, no light emission caused by current excitation was observed. Therefore, the electron current flowing through the device was found to be much smaller than the hole current.

Device Example 3

HOD1-3

A hole-only device (HOD1-3) was produced and evaluated by the same procedure as in Device Example 1 except that, instead of the polymer compound 3, a mixture of the polymer compound 5 and the polymer compound 4 in a weight ratio of 1:4 was used as the hole transport material.

In this evaluation, when an electric field with an intensity of 7×10$^5$ [V/cm$^2$] was applied to the device, no light emission caused by current excitation was observed. Therefore, the electron current flowing through the device was found to be much smaller than the hole current.

Device Comparative Example 1

HOD1-4

A hole-only device (HOD1-4) was produced and evaluated by the same procedure as in Device Example 1 except that, instead of the polymer compound 3, the polymer compound 4 was used as the hole transport material.

In this evaluation, when an electric field with an intensity of $7\times10^5$ [V/cm$^2$] was applied to the device, no light emission caused by current excitation was observed. Therefore, the electron current flowing through the device was found to be much smaller than the hole current.

TABLE f

| | Hole transport material | Electric current density [mA/cm$^2$] at electric field intensity of $7 \times 10^5$ [V/cm$^2$] |
|---|---|---|
| Device Example 1 HOD1-1 | Polymer compound 3 | 120.9 |
| Device Example 2 HOD1-2 | Polymer compound 3: Polymer compound 4 = 1:1 (weight ratio) | 60.2 |
| Device Example 3 HOD1-3 | Polymer compound 5: Polymer compound 4 = 1:4 (weight ratio) | 37.7 |
| Device Comparative Example 1 HOD1-4 | Polymer compound 4 | 25.9 |

As is clear from Table f, in Device Examples 1 to 3 in which compounds of the present invention were used, the current was larger than that in Device Comparative Example 1. This indicates high hole transport property of the compounds of the present invention.

<Evaluation 2 of Hole Transport Property>

Hole-only devices that are devices allowing only holes to flow therethrough were produced to evaluate the hole transport property of the compounds of the present invention.

Device Example 4

HOD2-1

(2-1: Formation of Hole Injection Layer)

A glass substrate having an ITO anode formed thereon was subjected to UV ozone cleaning and then spin-coated with a composition for forming a hole injection layer to obtain a coating with a thickness of 60 nm.

The substrate having the coating formed thereon was heated at 200° C. for 10 minutes to insolubilize the coating and then naturally cooled to room temperature to form a hole injection layer. An aqueous PEDOT:PSS solution (poly(3,4-ethylenedioxythiophene)polystyrene sulfonate, product name: Baytron) available from Starck-V Tech Ltd. was used as the composition for forming the hole injection layer.

(2-2: Formation of Hole Transport Layer)

The polymer compound 3 used as a hole transport material and xylene were mixed such that the ratio of the hole transport material was 0.8 percent by weight, and a composition for forming a hole transport layer was thereby obtained.

The hole injection layer obtained in (2-1) described above was applied by spin-coating method with the composition for forming a hole transport layer to obtain a coating having a thickness of 20 nm. The substrate having the coating formed thereon was heated at 180° C. for 60 minutes to insolubilize the coating and then naturally cooled to room temperature to obtain a hole transport layer.

(2-3: Formation of Light-Emitting Layer)

The polymer compound 6 used as a light-emitting material and xylene were mixed such that the ratio of the light-emitting polymer material was 1.4 percent by weight, and a composition for forming a light-emitting layer was thereby obtained.

The hole transport layer on the substrate having the anode, the hole injection layer, and the hole transport layer, which had been obtained in (2-2) described above, was spin-coated with the composition for forming a light-emitting layer to obtain a coating having a thickness of 80 nm. The substrate having the coating formed thereon was heated at 130° C. for 20 minutes to dry off the solvent and then naturally cooled to room temperature to form a light-emitting layer.

(2-4: Formation of Cathode)

Gold was deposited to a thickness of 80 nm by vacuum deposition on the light-emitting layer in the substrate obtained in (2-3) described above and having the anode, the hole injection layer, the hole transport layer, and the light-emitting layer, whereby a cathode was formed.

(2-5: Sealing)

The substrate having the stack, which had been obtained in (2-4) described above, was removed from the vacuum deposition apparatus and sealed with sealing glass and a two-component epoxy resin under a nitrogen atmosphere to obtain a hole-only device (HOD2-1).

(Evaluation)

A voltage from −1 V to +20 V was applied to the hole-only device (HOD2-1) using a DC voltage/current generator, and current density [mA/cm$^2$] flowing into the device when the electric field intensity was $7\times10^5$ [V/cm$^2$] was measured. The results are shown in Table g.

In this evaluation, when an electric field with an intensity of $7\times10^5$ [V/cm$^2$] was applied to the device, no light emission caused by current excitation was observed. Therefore, the electron current flowing through the device was found to be much smaller than the hole current. Although no light emission from the light-emitting layer was found in the hole-only device, light emission from the light-emitting layer described above was found in a bipolar device. Therefore, the term "light-emitting layer" was used.

Device Example 5

HOD2-2

A hole-only device (HOD2-2) was produced and evaluated by the same procedure as in Device Example 4 except that, instead of the polymer compound 3, the polymer compound 4 was used as the hole transport material.

In this evaluation, when an electric field with an intensity of $7\times10^5$ [V/cm$^2$] was applied to the device, no light emission caused by current excitation was observed. Therefore, the electron current flowing through the device was found to be much smaller than the hole current.

Device Comparative Example 2

HOD2-3

A hole-only device (HOD2-3) was produced and evaluated by the same procedure as in Device Example 5 except that, instead of the polymer compound 6, the polymer compound 7 was used as the light-emitting material.

In this evaluation, when an electric field with an intensity of $7\times10^5$ [V/cm$^2$] was applied to the device, no light emission caused by current excitation was observed. Therefore, the electron current flowing through the device was found to be much smaller than the hole current.

TABLE g

| | Hole transport material | Light-emitting material | Electric current density [mA/cm$^2$] at electric field intensity of $7 \times 10^5$ [V/cm$^2$] |
|---|---|---|---|
| Device Example 4 HOD2-1 | Polymer compound 3 | Polymer compound 6 | 10.3 |
| Device Example 5 HOD2-2 | Polymer compound 4 | Polymer compound 6 | 6.2 |
| Device Comparative Example 2 HOD2-3 | Polymer compound 4 | Polymer compound 7 | 2.6 |

As is clear from Table g, the results showed that, when compounds of the present invention were used for the hole transport layer or the light-emitting layer, high hole transport property was achieved.

<Evaluation 1 of Light-Emitting Devices (Bipolar Devices)>

Device Example 6

BPD1-1

(3-1: Formation of Hole Injection Layer)

A glass substrate having an ITO anode formed thereon was subjected to UV ozone cleaning and then spin-coated with a composition for forming a hole injection layer to obtain a coating with a thickness of 60 nm.

The substrate having the coating formed thereon was heated at 200° C. for 10 minutes to insolubilize the coating and then naturally cooled to room temperature to obtain a hole injection layer. An aqueous PEDOT:PSS solution (poly(3,4-ethylenedioxythiophene)polystyrene sulfonate, product name: Baytron) available from Starck-V Tech Ltd. was used as the composition for forming the hole injection layer.

(3-2: Formation of Hole Transport Layer)

The polymer compound 3 used as a hole transport material and xylene were mixed such that the ratio of the hole transport material was 0.8 percent by weight, and a composition for forming a hole transport layer was thereby obtained.

The hole injection layer obtained in (3-1) described above was applied by spin-coating method with the composition for forming a hole transport layer to obtain a coating having a thickness of 20 nm. The substrate having the coating formed thereon was heated at 180° C. for 60 minutes to insolubilize the coating and then naturally cooled to room temperature to form a hole transport layer.

(3-3: Formation of Light-Emitting Layer)

The polymer compound 7 used as a light-emitting polymer material and xylene were mixed such that the ratio of the light-emitting material was 1.4 percent by weight, and a composition for forming a light-emitting layer was thereby deposited.

The hole transport layer in the substrate having the anode, the hole injection layer, and the hole transport layer, which had been obtained in (3-2) described above, was spin-coated with the composition for forming a light-emitting layer to obtain a coating having a thickness of 80 nm. The substrate having the coating formed thereon was heated at 130° C. for 20 minutes to dry off the solvent and then naturally cooled to room temperature to form a light-emitting layer.

(3-4: Formation of Cathode)

A sodium fluoride layer having a thickness of 3 nm and then an aluminum layer having a thickness of 80 nm were continuously deposited by vacuum deposition on the light-emitting layer in the substrate having the anode, the hole injection layer, the hole transport layer, and the light-emitting layer, which had been obtained in (1-3) described above and, to form a cathode.

(3-5: Sealing)

The substrate having the stack, which had been obtained in (3-4) described above, was removed from the vacuum deposition apparatus, and sealed with sealing glass and a two-component epoxy resin under a nitrogen atmosphere to obtain a light-emitting device (BPD1-1).

(Evaluation)

A voltage of 3 V was applied to the light-emitting device (BPD1-1) using a DC voltage/current generator, and the current density flowing through the device and light emission intensity [cd/m$^2$] were measured. The results are shown in Table h.

Device Example 7

BPD1-2

A light-emitting device (BPD1-2) was produced and evaluated by the same procedure as in Device Example 6 except that, instead of the polymer compound 3, a mixture of the polymer compound 3 and the polymer compound 4 in a weight ratio of 1:1 was used as the hole transport material.

Device Example 8

BPD1-3

A light-emitting device (BPD1-3) was produced and evaluated by the same procedure as in Device Example 6 except that, instead of the polymer compound 3, a mixture of the polymer compound 5 and the polymer compound 4 in a weight ratio of 1:4 was used as the hole transport material.

Device Comparative Example 3

BPD1-4

A light-emitting device (BPD1-4) was produced and evaluated by the same procedure as in Example 6 except that, instead of the polymer compound 3, the polymer compound 4 was used as the hole transport material.

TABLE h

| | Hole transport material | Light-emitting material | Brightness [cd/m$^2$] | Electric current density [mA/cm$^2$] |
|---|---|---|---|---|
| Device Example 6 BPD1-1 | Polymer compound 3 | Polymer compound 7 | 112 | 2.87 |
| Device Example 7 BPD1-2 | Polymer compound 3: Polymer compound 4 = 1:1 (weight ratio) | Polymer compound 7 | 70 | 2.86 |
| Device Example 8 BPD1-3 | Polymer compound 5: Polymer compound 4 = 1:4 (weight ratio) | Polymer compound 7 | 64 | 1.97 |
| Device Comparative Example 3 BPD1-4 | Polymer compound 4 | Polymer compound 7 | 27 | 1.27 |

As is clear from Table h, in Device Examples 6 to 8 in which compounds of the present invention were used, the current was larger than the current in Device Comparative Example 3, and the light-emitting intensity was higher.
<Evaluation 2 of Light-Emitting Devices (Bipolar Devices)>

Device Example 9

BPD2-1

A light-emitting device (BPD2-1) was produced by the same procedure as in Device Example 6 except that, instead of the polymer compound 3, the polymer compound 4 was used as the hole transport material and that, instead of the polymer compound 7, the polymer compound 6 was used as the light-emitting material.
(Evaluation)

A voltage from −1 V to +20 V was applied to the light-emitting device (BPD2-1) using a DC voltage/current generator, and light emission intensity [cd/m²] and a light emission spectrum were measured. Chromaticity in the CIE colorimetric system was evaluated using the light emission spectrum when the light emission intensity was 1,000 [cd/m²]. The results are shown in Table i.

Device Example 10

BPD2-2

A light-emitting device (BPD2-2) was produced and evaluated by the same procedure as in Device Example 9 except that, instead of the polymer compound 6, a mixture of the polymer compound 5 and the polymer compound 7 in a weight ratio of 7:93 was used as the light-emitting material.

Device Example 11

BPD2-3

A light-emitting device (BPD2-3) was produced and evaluated by the same procedure as in Device Example 9 except that, instead of the polymer compound 6, a mixture of compound (IV) and the polymer compound 7 in a weight ratio of 7:93 was used as the light-emitting material.

Device Example 12

BPD2-4

A light-emitting device (BPD2-4) was produced and evaluated by the same procedure as in Device Example 9 except that, instead of the polymer compound 4, the polymer compound 3 was used as the hole transport material.

TABLE i

| | Hole transport material | Light-emitting material | Color coordinates | |
|---|---|---|---|---|
| | | | CIE-x | CIE-y |
| Device Example 9 BPD2-1 | Polymer compound 4 | Polymer compound 6 | 0.153 | 0.186 |
| Device Example 10 BPD2-2 | Polymer compound 4 | Polymer compound 5: Polymer compound 7 = 7:93 (weight ratio) | 0.171 | 0.200 |

TABLE i-continued

| | Hole transport material | Light-emitting material | Color coordinates | |
|---|---|---|---|---|
| | | | CIE-x | CIE-y |
| Device Example 11 BPD2-3 | Polymer compound 4 | Compound (IV): Polymer compound 7 = 7:93 (weight ratio) | 0.169 | 0.256 |
| Device Example 12 BPD2-4 | Polymer compound 3 | Polymer compound 6 | 0.151 | 0.182 |
| Device Comparative Example 3 BPD1-4 | Polymer compound 4 | Polymer compound 7 | 0.170 | 0.266 |

As is clear from Table i, in Device Examples 9 to 12 in which compounds of the present invention were used, the CIE-y value in the color coordinates in the CIE colorimetric system was smaller than that in Device Comparative Example 3, and the purity of blue color was higher.

INDUSTRIAL APPLICABILITY

The compound of the present invention is useful as a material for a light-emitting device such as an organic electroluminescent device and a materials for a photoelectric cell such as a solar cell. The compound of the present invention is also useful for, for example, a composition and a liquid composition for the above-described material, a film (e.g., a light-emitting film, a conductive film, and a semiconductor film), and a display apparatus including a light-emitting device.

The invention claimed is:
1. A compound comprising a residue obtained by removing at least one hydrogen atom from a structure represented by the following formula (1):

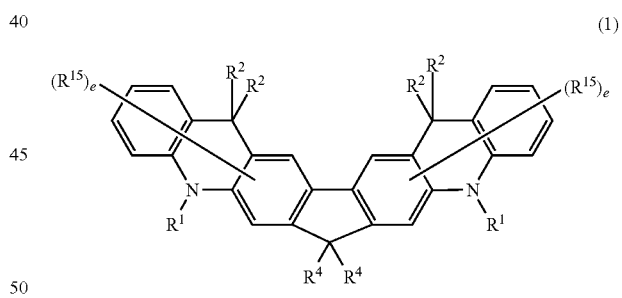

wherein
each $R^1$ represents a hydrogen atom, an alkyl group, an aryl group, an arylalkyl group, an acyl group, or a monovalent heterocyclic group, each of these groups optionally having a substituent;
the $R^1$s may be the same or different;
each $R^2$ represents a hydrogen atom, an alkyl group, an alkoxy group, an aryl group, an aryloxy group, an arylalkyl group, an arylalkoxy group, an alkenyl group, an arylalkenyl group, an acyl group, an acyloxy group, a monovalent heterocyclic group, or a heterocyclyloxy group, each of these groups optionally having a substituent;
the $R^2$s may be the same or different;
two $R^2$s bonded to the same carbon atom may be connected to form a ring;

each $R^4$ represents a hydrogen atom, an alkyl group, an aryl group, an arylalkyl group, or a monovalent heterocyclic group, each of these groups optionally having a substituent;

the $R^4$s may be the same or different;

the two $R^4$s may be connected to form a ring;

each $R^{15}$ represents an alkyl group, an alkoxy group, an aryl group, an aryloxy group, an arylalkyl group, an arylalkoxy group, an alkenyl group, an arylalkenyl group, an alkynyl group, an arylalkynyl group, an amino group, a silyl group, a halogen atom, an acyl group, an acyloxy group, a carbamoyl group, a monovalent heterocyclic group, a heterocyclyloxy group, a carboxyl group, a nitro group, or a cyano group, each of these groups optionally having a substituent;

where there are a plurality of $R^{15}$, they may be the same or different;

each e represents an integer of from 0 to 6; and the plurality of e's may be the same or different.

2. The compound according to claim 1 that is a polymer compound comprising a repeating unit represented by the following formula (2):

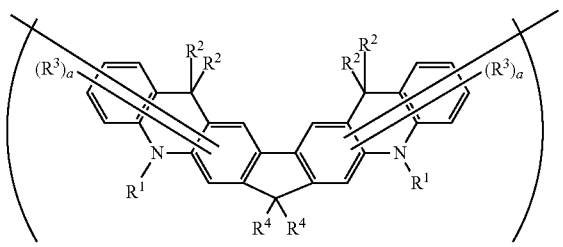

(2)

wherein each $R^1$ represents a hydrogen atom, an alkyl group, an aryl group, an arylalkyl group, an acyl group, or a monovalent heterocyclic group, each of these groups optionally having a substituent;

the $R^1$s may be the same or different;

each $R^2$ represents a hydrogen atom, an alkyl group, an alkoxy group, an aryl group, an aryloxy group, an arylalkyl group, an arylalkoxy group, an alkenyl group, an arylalkenyl group, an acyl group, an acyloxy group, a monovalent heterocyclic group, or a heterocyclyloxy group, each of these groups optionally having a substituent;

the $R^2$s may be the same or different;

two $R^2$s bonded to the same carbon atom may be connected to form a ring;

each $R^3$ represents an alkyl group, an alkoxy group, an aryl group, an aryloxy group, an arylalkyl group, an arylalkoxy group, an alkenyl group, an arylalkenyl group, an alkynyl group, an arylalkynyl group, an amino group, a silyl group, a halogen atom, an acyl group, an acyloxy group, a carbamoyl group, a monovalent heterocyclic group, a heterocyclyloxy group, a carboxyl group, a nitro group, or a cyano group, each of these groups optionally having a substituent;

where there are a plurality of $R^3$, they may be the same or different;

each $R^4$ represents a hydrogen atom, an alkyl group, an aryl group, an arylalkyl group, or a monovalent heterocyclic group, each of these groups optionally having a substituent;

the $R^4$s may be the same or different;

the two $R^4$s may be connected to form a ring;

each a represents an integer of from 0 to 5; and the a's may be the same or different.

3. The compound according to claim 2, wherein said repeating unit represented by formula (2) is a repeating unit represented by the following formula (3):

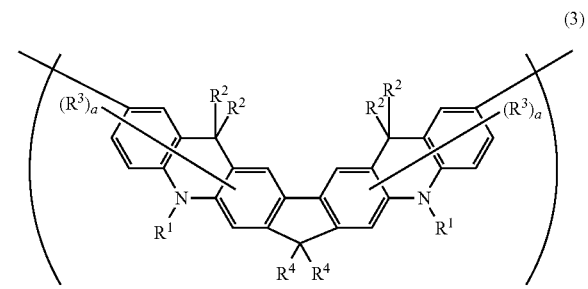

(3)

wherein $R^1$, $R^2$, $R^3$, $R^4$, and a are the same as defined for formula (2).

4. The compound according to claim 2 further comprising a repeating unit represented by the following formula (4):

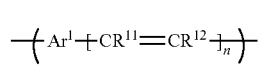

(4)

wherein $Ar^1$ represents an arylene group or a divalent heterocyclic group, each of these groups optionally having a substituent;

$R^{11}$ and $R^{12}$ each independently represent a hydrogen atom, an alkyl group, an aryl group, a monovalent heterocyclic group, or a cyano group, each of these groups optionally having a substituent; and n represents 0 or 1.

5. The compound according to claim 4, wherein said repeating unit represented by formula (4) is a repeating unit represented by the following formula (5):

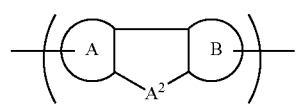

(5)

wherein a ring A and a ring B each independently represent an aromatic hydrocarbon ring or an aromatic heterocyclic ring, each of these rings optionally having a substituent; and $A^2$ represents a linking group.

6. The compound according to claim 5, wherein said repeating unit represented by formula (5) is a repeating unit represented by the following formula (6):

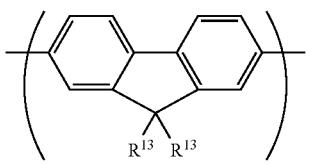

wherein
each $R^{13}$ represents a hydrogen atom, an alkyl group, an aryl group, an arylalkyl group, or a monovalent heterocyclic group, each of these groups optionally having a substituent;
the $R^{13}$s may be the same or different; and
the two $R^{13}$s may be connected to form a ring.

7. A method of producing a compound comprising a repeating unit represented by the following formula (3):

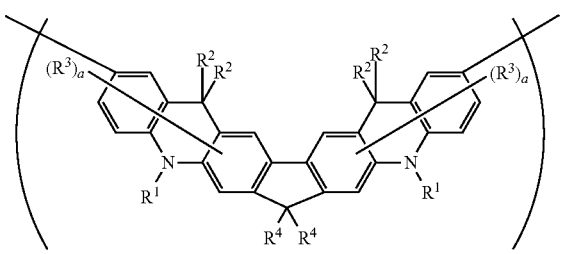

wherein
each $R^1$ represents a hydrogen atom, an alkyl group, an aryl group, an arylalkyl group, an acyl group, or a monovalent heterocyclic group, each of these groups optionally having a substituent;
the $R^1$s may be the same or different;
each $R^2$ represents a hydrogen atom, an alkyl group, an alkoxy group, an aryl group, an aryloxy group, an arylalkyl group, an arylalkoxy group, an alkenyl group, an arylalkenyl group, an acyl group, an acyloxy group, a monovalent heterocyclic group, or a heterocyclyloxy group, each of these groups optionally having a substituent;
the $R^2$s may be the same or different;
two $R^2$s bonded to the same carbon atom may be connected to form a ring;
each $R^3$ represents an alkyl group, an alkoxy group, an aryl group, an aryloxy group, an arylalkyl group, an arylalkoxy group, an alkenyl group, an arylalkenyl group, an alkynyl group, an arylalkynyl group, an amino group, a silyl group, a halogen atom, an acyl group, an acyloxy group, a carbamoyl group, a monovalent heterocyclic group, a heterocyclyloxy group, a carboxyl group, a nitro group, or a cyano group, each of these groups optionally having a substituent;
where there are a plurality of $R^3$, they may be the same or different;
each $R^4$ represents a hydrogen atom, an alkyl group, an aryl group, an arylalkyl group, or a monovalent heterocyclic group, each of these groups optionally having a substituent;

the $R^4$s may be the same or different;
the two $R^4$s may be connected to form a ring;
each a represents an integer of from 0 to 5; and
the a's may be the same or different;
the method comprising polymerizing a compound represented by the following formula (7):

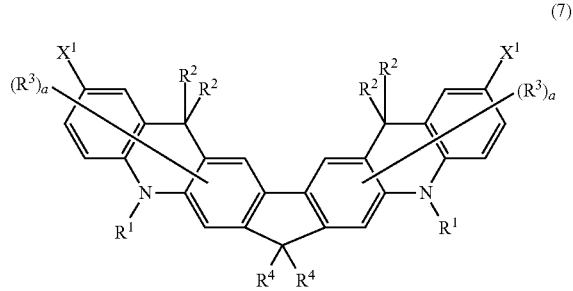

wherein
$R^1$, $R^2$, $R^3$, $R^4$, and a are the same as in formula (3);
each $X^1$ represents a group capable of participating in polymerization; and
the $X^1$s may be the same or different;
to obtain the compound comprising the repeating unit represented by formula (3).

8. A compound represented by the following formula (7):

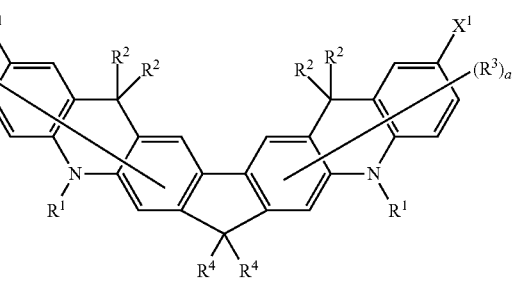

wherein
each $R^1$ represents a hydrogen atom, an alkyl group, an aryl group, an arylalkyl group, an acyl group, or a monovalent heterocyclic group, each of these groups optionally having a substituent;
the $R^1$s may be the same or different;
each $R^2$ represents a hydrogen atom, an alkyl group, an alkoxy group, an aryl group, an aryloxy group, an arylalkyl group, an arylalkoxy group, an alkenyl group, an arylalkenyl group, an acyl group, an acyloxy group, a monovalent heterocyclic group, or a heterocyclyloxy group, each of these groups optionally having a substituent;
the $R^2$s may be the same or different;
two $R^2$s bonded to the same carbon atom may be connected to form a ring;
each $R^3$ represents an alkyl group, an alkoxy group, an aryl group, an aryloxy group, an arylalkyl group, an arylalkoxy group, an alkenyl group, an arylalkenyl group, an alkynyl group, an arylalkynyl group, an amino group, a silyl group, a halogen atom, an acyl group, an acyloxy group, a carbamoyl group, a monovalent heterocyclic group, a heterocyclyloxy group, a carboxyl group, a nitro group, or a cyano group, each of these groups optionally having a substituent;

where there are a plurality of $R^3$, they may be the same or different;

each $R^4$ represents a hydrogen atom, an alkyl group, an aryl group, an arylalkyl group, or a monovalent heterocyclic group, each of these groups optionally having a substituent;

the $R^4$s may be the same or different;

the two $R^4$s may be connected to form a ring;

each $X^1$ represents a group capable of participating in polymerization;

the $X^1$s may be the same or different;

each a represents an integer of from 0 to 5; and the a's may be the same or different.

9. A method of producing a compound represented by the following formula (7-1):

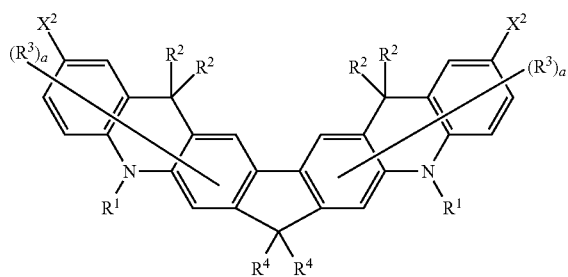

(7-1)

wherein
each $R^1$ represents a hydrogen atom, an alkyl group, an aryl group, an arylalkyl group, an acyl group, or a monovalent heterocyclic group, each of these groups optionally having a substituent;
the $R^1$s may be the same or different;
each $R^2$ represents a hydrogen atom, an alkyl group, an alkoxy group, an aryl group, an aryloxy group, an arylalkyl group, an arylalkoxy group, an alkenyl group, an arylalkenyl group, an acyl group, an acyloxy group, a monovalent heterocyclic group, or a heterocyclyloxy group, each of these groups optionally having a substituent;
the $R^2$s may be the same or different;
two $R^2$s bonded to the same carbon atom may be connected to form a ring;
each $R^3$ represents an alkyl group, an alkoxy group, an aryl group, an aryloxy group, an arylalkyl group, an arylalkoxy group, an alkenyl group, an arylalkenyl group, an alkynyl group, an arylalkynyl group, an amino group, a silyl group, a halogen atom, an acyl group, an acyloxy group, a carbamoyl group, a monovalent heterocyclic group, a heterocyclyloxy group, a carboxyl group, a nitro group, or a cyano group, each of these groups optionally having a substituent;
where there are a plurality of $R^3$, they may be the same or different;
each $R^4$ represents a hydrogen atom, an alkyl group, an aryl group, an arylalkyl group, or a monovalent heterocyclic group, each of these groups optionally having a substituent;
the $R^4$s may be the same or different;
the two $R^4$s may be connected to form a ring;

each a represents an integer of from 0 to 5;
the a's may be the same or different;
each $X^2$ represents a halogen atom; and
the $X^2$s may be the same or different;
the method comprising reacting a compound represented by the following formula (8):

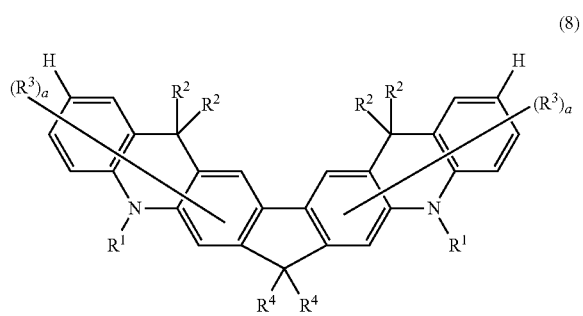

(8)

wherein
$R^1$, $R^2$, $R^3$, $R^4$, and a are the same as in formula (7-1); with a halogenation agent to obtain the compound represented by formula (7-1).

10. A compound represented by the following formula (8):

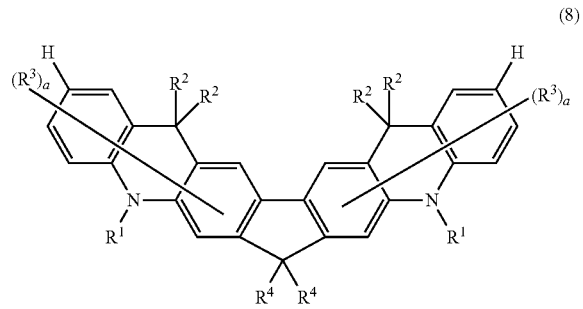

(8)

wherein
each $R^1$ represents a hydrogen atom, an alkyl group, an aryl group, an arylalkyl group, an acyl group, or a monovalent heterocyclic group, each of these groups optionally having a substituent;
the $R^1$s may be the same or different;
each $R^2$ represents a hydrogen atom, an alkyl group, an alkoxy group, an aryl group, an aryloxy group, an arylalkyl group, an arylalkoxy group, an alkenyl group, an arylalkenyl group, an acyl group, an acyloxy group, a monovalent heterocyclic group, or a heterocyclyloxy group, each of these groups optionally having a substituent;
the $R^2$s may be the same or different;
two $R^2$s bonded to the same carbon atom may be connected to form a ring;
each $R^3$ represents an alkyl group, an alkoxy group, an aryl group, an aryloxy group, an arylalkyl group, an arylalkoxy group, an alkenyl group, an arylalkenyl group, an alkynyl group, an arylalkynyl group, an amino group, a silyl group, a halogen atom, an acyl group, an acyloxy group, a carbamoyl group, a monovalent heterocyclic group, a heterocyclyloxy group, a carboxyl group, a nitro group, or a cyano group, each of these groups optionally having a substituent;

where there are a plurality of $R^3$, they may be the same or different;

each $R^4$ represents a hydrogen atom, an alkyl group, an aryl group, an arylalkyl group, or a monovalent heterocyclic group, each of these groups optionally having a substituent;

the $R^4$s may be the same or different;

the two $R^4$s may be connected to form a ring;

each a represents an integer of from 0 to 5; and the a's may be the same or different.

11. A method of producing a compound represented by the following formula (8):

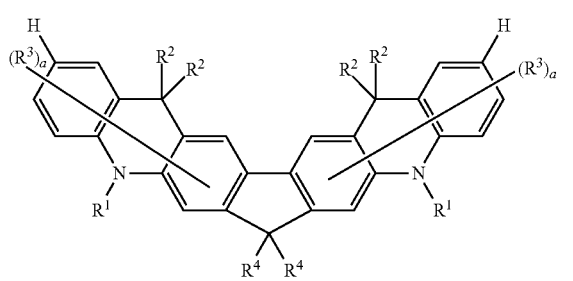

(8)

wherein each $R^1$ represents a hydrogen atom, an alkyl group, an aryl group, an arylalkyl group, an acyl group, or a monovalent heterocyclic group, each of these groups optionally having a substituent;

the $R^1$s may be the same or different;

each $R^2$ represents a hydrogen atom, an alkyl group, an alkoxy group, an aryl group, an aryloxy group, an arylalkyl group, an arylalkoxy group, an alkenyl group, an arylalkenyl group, an acyl group, an acyloxy group, a monovalent heterocyclic group, or a heterocyclyloxy group, each of these groups optionally having a substituent;

the $R^2$s may be the same or different;

two $R^2$s bonded to the same carbon atom may be connected to form a ring;

each $R^3$ represents an alkyl group, an alkoxy group, an aryl group, an aryloxy group, an arylalkyl group, an arylalkoxy group, an alkenyl group, an arylalkenyl group, an alkynyl group, an arylalkynyl group, an amino group, a silyl group, a halogen atom, an acyl group, an acyloxy group, a carbamoyl group, a monovalent heterocyclic group, a heterocyclyloxy group, a carboxyl group, a nitro group, or a cyano group, each of these groups optionally having a substituent;

where there are a plurality of $R^3$, they may be the same or different;

each $R^4$ represents a hydrogen atom, an alkyl group, an aryl group, an arylalkyl group, or a monovalent heterocyclic group, each of these groups optionally having a substituent;

the $R^4$s may be the same or different;

the two $R^4$s may be connected to form a ring;

each a represents an integer of from 0 to 5; and the a's may be the same or different;

the method comprising reacting a compound represented by the following formula (9):

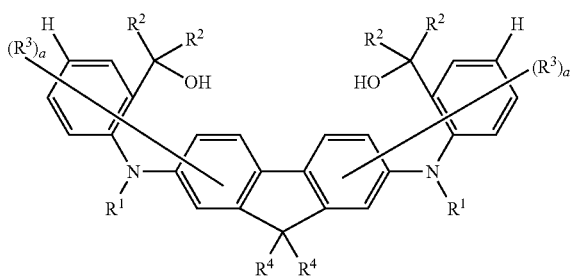

(9)

wherein each $R^1$ represents a hydrogen atom, an alkyl group, an aryl group, an arylalkyl group, an acyl group, or a monovalent heterocyclic group, each of these groups optionally having a substituent;

the $R^1$s may be the same or different;

each $R^2$ represents a hydrogen atom, an alkyl group, an alkoxy group, an aryl group, an aryloxy group, an arylalkyl group, an arylalkoxy group, an alkenyl group, an arylalkenyl group, an acyl group, an acyloxy group, a monovalent heterocyclic group, or a heterocyclyloxy group, each of these groups optionally having a substituent;

the $R^2$s may be the same or different;

two $R^2$s bonded to the same carbon atom may be connected to form a ring;

each $R^3$ represents an alkyl group, an alkoxy group, an aryl group, an aryloxy group, an arylalkyl group, an arylalkoxy group, an alkenyl group, an arylalkenyl group, an alkynyl group, an arylalkynyl group, an amino group, a silyl group, a halogen atom, an acyl group, an acyloxy group, a carbamoyl group, a monovalent heterocyclic group, a heterocyclyloxy group, a carboxyl group, a nitro group, or a cyano group, each of these groups optionally having a substituent;

where there are a plurality of $R^3$, they may be the same or different;

each $R^4$ represents a hydrogen atom, an alkyl group, an aryl group, an arylalkyl group, or a monovalent heterocyclic group, each of these groups optionally having a substituent;

the $R^4$s may be the same or different;

the two $R^4$s may be connected to form a ring;

each a represents an integer of from 0 to 5; and the a's may be the same or different;

in the presence of an acid to obtain the compound represented by formula (8).

12. A composition comprising:
   (a) the compound according to claim 1; and
   (b) at least one material selected from the group consisting of a hole transport material, an electron transport material, and a light-emitting material.

13. A liquid composition comprising the compound according to claim 1.

14. A film comprising the compound according to claim 1.

15. A device including:
   (a) electrodes comprising an anode and a cathode; and
   (b) an organic layer comprising the compound according to claim 1, which is disposed between the electrodes.

16. A display apparatus including the device according to claim 15.

* * * * *